US007674823B2

(12) United States Patent
Martin et al.

(10) Patent No.: US 7,674,823 B2
(45) Date of Patent: *Mar. 9, 2010

(54) DNA-PK INHIBITORS

(75) Inventors: Niall Morrison Barr Martin, Cambridge (GB); Graeme Cameron Murray Smith, Cambridge (GB); Roger John Griffin, Newcastle Upon Tyne (GB); Bernard Thomas Golding, Newcastle Upon Tyne (GB); Ian Robert Hardcastle, Newcastle Upon Tyne (GB); David Richard Newell, Newcastle Upon Tyne (GB); Hilary Alan Calvert, Newcastle Upon Tyne (GB); Nicola Jane Curtin, Newcastle Upon Tyne (GB); Laurent Jean Martin Rigoreau, Sussex (GB); Xiao-ling Fan Cockcroft, Sussex (GB); Vincent Junior Ming-lai Loh, Sussex (GB); Paul Workman, Surrey (GB); Florence Irene Raynaud, Surrey (GB); Bernard Paul Nutley, Surrey (GB)

(73) Assignee: Cancer Research Technology Limited, London (GB)

( * ) Notice: Subject to any disclaimer, the term of this patent is extended or adjusted under 35 U.S.C. 154(b) by 203 days.

This patent is subject to a terminal disclaimer.

(21) Appl. No.: 11/758,332

(22) Filed: Jun. 5, 2007

(65) Prior Publication Data
US 2007/0238729 A1 Oct. 11, 2007

Related U.S. Application Data

(62) Division of application No. 10/486,816, filed as application No. PCT/GB02/03781 on Aug. 14, 2002, now Pat. No. 7,226,918.

(30) Foreign Application Priority Data

Aug. 14, 2001 (GB) .................. 0119865.4

(51) Int. Cl.
*A61K 31/351* (2006.01)
(52) U.S. Cl. .................. 514/459
(58) Field of Classification Search .................. 514/472, 514/459
See application file for complete search history.

(56) References Cited

U.S. PATENT DOCUMENTS

| 4,954,518 | A | 9/1990 | Takano et al. |
|---|---|---|---|
| 5,252,735 | A | 10/1993 | Morris |
| 5,284,856 | A | 2/1994 | Naik et al. |
| 5,302,613 | A | 4/1994 | Morris |
| 5,703,075 | A | 12/1997 | Gammill et al. |
| 5,733,920 | A | 3/1998 | Mansuri et al. |
| 5,922,755 | A | 7/1999 | Tanaka et al. |
| 6,348,311 | B1 | 2/2002 | Kastan et al. |
| 6,387,640 | B1 | 5/2002 | Kastan et al. |
| 7,049,313 | B2 | 5/2006 | Smith et al. |
| 7,056,942 | B2 | 6/2006 | Hildesheim et al. |
| 7,105,518 | B2 | 9/2006 | Martin et al. |
| 2004/0023968 | A1 | 2/2004 | Martin et al. |
| 2005/0054657 | A1 | 3/2005 | Smith et al. |
| 2006/0106025 | A1 | 5/2006 | Smith et al. |
| 2006/0178361 | A1 | 8/2006 | Hummersone et al. |
| 2006/0264427 | A1 | 11/2006 | Smith et al. |
| 2006/0264623 | A1 | 11/2006 | Smith et al. |
| 2007/0238731 | A1 | 10/2007 | Smith et al. |
| 2008/0242664 | A1 | 10/2008 | Smith et al. |
| 2009/0042865 | A1 | 2/2009 | Frigerio |
| 2009/0043091 | A1 | 2/2009 | Smith et al. |

FOREIGN PATENT DOCUMENTS

| EP | 0 610 519 A1 | 8/1994 |
|---|---|---|
| EP | 0 635 268 A1 | 1/1995 |
| EP | 0 640 339 A1 | 3/1995 |

(Continued)

OTHER PUBLICATIONS

United States Patent Office Action for U.S. Appl. No. 11/351,052 dated Feb. 23, 2009 (10 pages).
United States Patent Office Action for U.S. Appl. No. 11/351,052 dated Aug. 15, 2008 (8 pages).
United States Patent Office Action for U.S. Appl. No. 11/351,052 dated Nov. 26, 2007 (8 pages).
United States Patent Office Action for U.S. Appl. No. 11/351,052 dated Jun. 13, 2007 (11 pages).
United States Patent Office Action for U.S. Appl. No. 10/373,114 dated Aug. 31, 2004 (15 pages).
United States Patent Office Action for U.S. Appl. No. 10/373,114 dated Mar. 30, 2005 (5 pages).
United States Patent Office Action for U.S. Appl. No. 10/918,180 dated Jun. 6, 2007 (12 pages).

(Continued)

*Primary Examiner*—Taofiq A Solola
(74) *Attorney, Agent, or Firm*—Michael Best & Freidrich LLP

(57) ABSTRACT

The invention relates to the use of compounds of formula (I) and isomers, salts, solvates, chemically protected forms, and prodrugs thereof, in the preparation of a medicament for inhibiting the activity of DNA-PK, wherein $R^1$ and $R^2$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms; X and Y are selected from $CR^4$ and O, O and $CR'^4$ and $NR'''^4$ and N, where the unsaturation is in the appropriate place in the ring, and where one of $R^3$ and $R^4$ or $R'^4$ is an optionally substituted $C_{3-20}$ heteroaryl or $C_{5-20}$ aryl group, and the other of $R^3$ and $R^4$ or $R'^4$ is H, or $R^3$ and $R^4$ or $R'''^4$ together are —A—B—, which collectively represent a fused optionally substituted aromatic ring. The compounds also selectively inhibit the activity of DNA-PK compared to PI 3-kinase and/or ATM.

7 Claims, 5 Drawing Sheets

FOREIGN PATENT DOCUMENTS

| | | |
|---|---|---|
| EP | 0 641 566 A1 | 3/1995 |
| EP | 0 648 492 A2 | 4/1995 |
| EP | 0 658 343 A1 | 6/1995 |
| GB | 1303724 | 1/1973 |
| GB | 2 302 021 A | 1/1997 |
| JP | 03215-423 | 1/1990 |
| WO | WO 90/06921 | 6/1990 |
| WO | WO 91/19707 | 12/1991 |
| WO | WO 92/00290 | 1/1992 |
| WO | WO 95/29673 | 11/1995 |
| WO | WO 96/01108 | 1/1996 |
| WO | WO 97/15658 | 5/1997 |
| WO | WO 97/18323 | 5/1997 |
| WO | WO 98/55602 | 12/1998 |
| WO | WO 98/56391 | 12/1998 |
| WO | WO 99/47494 | 9/1999 |
| WO | WO 01/53266 A1 | 7/2001 |
| WO | WO 02/20500 A2 | 3/2002 |
| WO | WO 02/056912 A2 | 7/2002 |
| WO | WO 03/024949 A1 | 3/2003 |
| WO | WO 03/093261 | 4/2003 |
| WO | WO 03/034997 A2 | 5/2003 |
| WO | WO 03/035618 A2 | 5/2003 |
| WO | WO 03/070726 | 8/2003 |
| WO | WO 2006/032869 | 3/2006 |

OTHER PUBLICATIONS

United States Patent Office Action for U.S. Appl. No. 10/918,180 dated Dec. 5, 2007 (6 pages).
United States Patent Office Action for U.S. Appl. No. 10/486,811 dated Sep. 19, 2005 (4 pages).
United States Patent Office Action for U.S. Appl. No. 10/486,811 dated Jan. 5, 2006 (4 pages).
United States Patent Office Action for U.S. Appl. No. 11/231,041 dated Jul. 19, 2007 (13 pages).
Abraham, Robert T., "Cell cycle checkpoint signaling through the ATM and ATR kinases," *Genes & Dev.*, 15: 2177-2196 (2001).
Archer, S. et al., "Ring-Hydroxylated Analogues of Lucanthone as Antitumore Agents," *J. Med Chem.*, 25, 220-227 (1982).
Banin, S., et al., "Enhanced phosphorylation of p53 by ATM in response to DNA damage," *Science*, 281:1674-1677 (1998).
Bantick, J.R., et al., "Synthesis of 2-aminochromones," *J. Heterocyclic Chem.*, 1981, vol. 18, pp. 679-684.
Berge, Stephen M., et al., "Review article," *J. Pharm. Sci.*, 66:1, pp. 1-19 (1977).
Bettoni, et al., "Synthesis and absolute configuration of substituted morpholines," *Tetrahedron*, 1980, vol. 36, pp. 409-415.
Boyd, J., et al., "The chemistry of the 'insoluble red' woods," *J. Chem. Soc.*, 1948, pp. 174-176.
Brown, P.O., "Integration of retroviral DNA," *Curr Top Microbiol Immunol.*, 157:19-48 (1990).
Buon, C., et al., "Synthesis of 3-substituted and 2,3-disubstituted-4H-1,4- Benzoxazines," *Tetrahedron*, 2000, vol. 56, pp. 604-614.
Chiosis, G, et al. "LY294002-geldanamycin heterodiamers as selective inhibitors of the PI3K and PI3k-related family", *Bioorganic & Medicinal Chemistry Letters*, vol. 11, No. 7, Apr. 9, 2001 pp. 909-913, XP004232522.
Daniel, R., et al., "A role for DNA-PK in retroviral DNA integration," *Science*, 1999, vol. 284, pp. 644-647.
Daniel, Rene, et al., "Wortmannin potentiates integrase-mediated killing of lymphocytes and reduces the efficiency of stable transduction by retroviruses," *Mol. Cell Biol*, 21:4, 1164-1172 (2001).
Datta, A., et al., "Reformatsky reaction on aroylketene S, N-acetals: a facile route to 4-amino-6-aryl-2H-pyran-2-ones," *Synthesis*, 1988, vol. 3, pp. 248-250.
Di Braccio, M., et al., "1,2-fused pyrimidines VII," *Eur. J. Med., Chem.*, 1995, vol. 30, No. 1, pp. 27-38.
Di Braccio, M., et al., "Pyran derivatives XIX. (Dialkylamino) substituted 1-benzopyranones and naphthopyranoes with platelet antiaggregating activity," *Farmaco*, 1995, vol. 50, No. 10, pp. 703-711.

Durocher, Daniel, and Jackson, Stephen P., "DNA-PK, ATM and ATR as sensors of DNA damage: variations on a theme?," *Curr Opin Cell Biol.*, 13:225-231(2001).
Ermili, A., et al., "Chemical and pharmacological research on pyran derivatives," Enclosed: *Chemical Abstracts*, 1977, vol. 87, No. 15, p. 588 (XP-002218602), 117750g.
Gell, D., et al., "Mapping of protein-protein interactions within the DNA-dependent protein kinase complex," *Nucleic Acid Res.*, 1999, vol. 27, No. 17, pp. 3494-3502.
Giroux, A., et al, "One pot biaryl synthesis via in situ boronate formation," *Tet. Lett.*, 38:22, 3841-3844 (1997).
Goytisolo, et al., "The absence of DNA-dependent protein kinase catalytic subunit in mice results in anaphase bridges and in increased telomeric fusions with normal telomere length and G-strand overhang," *Mol. Cell. Biol.*, 2001, vol. 21, No. 11, pp. 3642-3651.
Greene, T. and Wuts, P., ed., *Protective Groups in Organic Synthesis*, Wiley (1999).
Griffin, et al., "Selective Benzopyranone and Pyrimido [2,1-a]isoquinolin-4-one Inhibitors of DNA-Dependent Protein Kinase: Synthesis, Structure—Activity Studies, and Radiosensitization of a Humn Tumor Cell Line in Vitro", *J. Med. Chem.*, 2005, 48, 569-585.
Hartley, K. O., et al., "DNA-dependent protein kinase catalytic subunit: a relative of phosphatidylinositol 3-kinase and the ataxia telengiectasia gene product," *Cell*, 1995, vol. 82, pp. 849-856.
Haselhorst, Dorte, et al., "Development of cell lines stably expressing human immunodeficiency virus type 1 proteins for studies in encapsidation and gene transfer," *J Gen Virol*, 79: 231-237 (1998).
Herzog, Karl-Heinz et al.,"Requirement for ATM in ionizing radiation-induced cell death in the developing central nervous system," *Science*, 280: 1089-1091 (1998).
Hickson, Ian, et al, "Identification and Characterization of a Novel and Specific Inhibitor of the Ataxia-Telangiectasia Mutated Kinase ATM," *Cancer Research* 64, Dec. 15, 2004, 9152-9159.
Hollick, J J, et al., "2,6-Disubstituted pyran-4-one and thiopyran-4-one inhibitors of DNA-dependent protein kinase" *Bioorganic and Medicinal Chemistry Letters*, vol. 13, No. 18, Sep. 15, 2003 pp. 3083-3086, XP002303369.
Ishiyama, T. et al., "Synthesis of arylboronates via the palladium(0)-catalyzed cross-coupling reaction of tetra(alkoxo)diborons with aryl triflates," *Tett. Lett.*, 38:19, 3447-3450 (1997).
Ismail, I.H. et al., "SU11752 inhibits the DNA-dependent protein kinase and DNA double-strand break repair resulting in ionizing radiation sensitization," *Oncogene* (2004) 23:873-883.
Izzard, R.A., et al., "Competitive & noncompetitive inhibition of the DNA-dependent protein kinase," *Cancer Research*, 1999, vol. 59, No. 11, pp. 2581-2586.
Jackson, S. P., "DNA damage detection by DNA dependent protein kinase and related enzymes," *Cancer Surv.*, 1996, vol. 28, pp. 261-279.
Jung, J. C., et al., "Simple and cost effective synthesis of 4-hydroxycoumarin," *Synth. Commun.*, 1999, vol. 29, No. 20, pp. 3587-3595.
Kashishian, A. et al., "DNA-dependent protein kinase inhibitors as drug candidates for the treatment of cancer," *Mol. Cancer Ther.* (2003) 2:1257-1264.
Keith, Curtis T. and Schreiber, Stuart L., "PIK-related kinases: DNA repair, recombination, and cell cycle checkpoints," *Science*, 270: 50-51 (1995).
Knight, A.R., et al., "Isolation and characterization of 4-chloro-3,4'; 3',4"-tercoumarin," *Can. J. Chem.*, 1968, vol. 46, pp. 2495-2499.
Kubik, et al., "Fine tuning of the cation affinity of artificial receptors based on cyclic peptides by intramolecular conformational control," *Eur. J. Org. Chem.*, 2001, pp. 311-312.
Lau et al., "Suprression of HIV-1 infection by a small molecule inhibitor of the ATM kinase," Nature Cell Biology (2005) 7:493-500.
Lavin, Martin F. and Shiloh, Yosef, "The genetic defect in ataxia-telangiectasia," *Annu. Rev. Immunol*, 15:177-202 (1997).
Leahy, et al., "Identification of a highly potent and selective DNA-dependent protein kinase (DNA-PK) inhibitor (NU7441) by screening of chromenone librariest", *Bioorganic & Medicinal Chemistry Letters* 14 (2004) 6083-6087.
Metcalfe, Judith A. et al., "Accelerated telomere shortening in ataxia telangiectasia," *Nature Genetics*, 13: 350-353 (1996).

Mlotkowska, B.L. et al., "Two-dimensional NMR studies of 2-substituted thioxanthene sulfoxides," *J. Heterocyclic Chem.*, 28: 731-736 (Apr.-May 1991).

Morris, J., et al., "Synthesis and biological evaluation of antiplatelet 2-aminochromones," *J. Med Chem.*, 1993, vol. 36, No. 14, pp. 2026-2032.

Morris, J., et al., "Synthesis of 2-amino-6-phenyl-4*H*-pyran-4-ones," *Synthesis*, 1994, pp. 43-46.

Morris, J., et al., "Reaction of phosgeniminium salts with enolates derived from Lewis acid complexes of 2'-hydroxypropiophenones and related β-Diketones," *J. Org. Chem.*, 1996, vol. 61, No. 9, pp. 3218-3220.

Muller, C. et al., "DNA-dependent protein kinase activity correlates with clinical and in vitro sensitivity of chronic lymphocytic leukemia lymphocytes to nitrogen mustards," Blood (1998) 92:2213-2219.

Naldini, Luigi et al., "In vivo gene delivery and stable transduction of nondividing cells by a lentiviral vector," *Science*, 272: 263-267 (1996).

Oh, C., et al., "Nucleophilic vinylic substitution of halocoumarins and halo-1,4-napthoquinones with morpholine," *J. Heterocyclic Chem.*, 1994, vol. 31, pp. 841-843.

*Remington's Pharmaceutical Sciences*, 18$^{th}$ ed., Mack Pub. Co., Easton, PA (1990).

Roma, G., et al., "Synthesis, antiplatelet activity and comparative molecular field analysis of substituted 2-amino-4H pyrido[1,2-a]pyrimidin-4-ones, their congeners and isosteric analogues," *Bioorganic & Medicinal Chemistry*, 2000, vol. 8, pp. 751-768.

Roma, G., et al., "Pyran derivatives XX. 2-aminochromone benzofused derivatives with antiproliferative properties," *Il Farmaco*, 1998, vol. 53, pp. 494-503.

Rosenzweig, K.E., et al., "Radiosensitization of human tumor cells by the phosphatidylinositol 3-kinase inhibitors Wortmannin and LY294002 correlates with inhibition of DNA-dependent protein kinase and prolonged G2-M delay," *Clin. Cancer Res.*, 1997, vol. 3, 1149-1156.

Sarkaria, Jann N. et al., "Inhibition of ATM and ATR kinase activities by the radiosensitizing agent, caffeine," *Cancer Res.*, 59: 4375-4382 (1999).

Savitsky, Kinneret et al., "A single ataxia telangiectasia gene with a product similar to P1-3 kinase," *Science*, 268:1749-1753 (1995).

Schroth, W., et al., "2,4,6-Tris(dialkylamino) pyrylium salts and related systems, synthesis and reaction behavior," *Tetrahedron Letters*, 1988, vol. 29, No. 37, pp. 4695-4698.

Schroth, W. et al., "2,4,6-Tris(dialkylamino) pyrylium salts and related systems, synthesis and reaction behavior," *Chemical Abstracts*, 110:135031.

Shiloh, Yosef, "ATM and ATR: networking cellular responses to DNA damage," *Curr. Opin. Genet. Dev.*, 11:71-77 (2001).

Sirzen, F. et al., "DNA-dependent protein kinase content and activity in lung carcinoma cell lines: correlation with intrinsic radiosensitivity," Eur. J. Cancer (1999) 35:111-116.

Skehan, P., et al., "New colorimetric cytotoxicity assay for anticancer-drug screening," *J. Natl. Cancer Inst.*, 1990, vol. 82, No. 13, pp. 1107-1112.

Smith, G. C. M., et al., "The DNA-dependent protein kinase," *Genes & Dev.*, 1999, vol. 13, pp. 916-934.

Snyder, et al., "Structure and reactions of malonyl-α-aminopyridine. I," *J. Am. Chem. Soc.*, 1952, vol. 74, pp. 4910-4914.

Ten Hoeve, et al., "Direct substitution of aromatic ethers by lithium amides. A new aromatic amination reaction," *J. Org. Chem.*, 1993, vol. 58, pp. 5101-5106.

Toker, Alex and Cantley, Lewis C., "Signalling through the lipid products of phosphoinositide-3-OH kinase," *Nature*, 387:673-676 (1997).

Veuger, S. J., et al., "Radiosensitization and DNA repair inhibition by the combined use of novel inhibitors of DNA-dependent protein kinase and poly (ADP-ribose) polymerase-1," *Cancer Research*, 2003, vol. 63, pp. 6008-6015.

Vlahos, C. J., et al., "A specific inhibitor of phosphatidylinositol 3-kinase, 2-(4- morpholinyl)-8-phenyl-4H-1-benzopyran-4-one (LY294002)," *J. Biol. Chem.*, 1994, vol. 269, No. 7, pp. 5241-5248.

Willmore et al., "A novel DNA-dependent protein kinase inhibitor, NU7026, potentiates the cytotoxicity of topoisomerase II poisons used in the treatment of leukemia", *Blood*, Jun. 15, 2004, vol. 103, No. 12, 4659-4665.

Wymann, M. T., et al., "Wortmannin inactivates phosphoinositide-3-kinase by covalent modification of Lys-802, a residue involved in the phosphate transfer reaction," *Mol. Cell Biol.*, 1996, vol. 16, No. 4, pp. 1722-1733.

Zakian, Virginia A., "ATM-related genes: What do they tell us about functions of the human gene?" *Cell*, 82:685-687 (1995).

Bryn, S.R. et al., "Hydrates and solvates," in Solid-State Chemistry of Drugs, Second Edition (1999) 233-247.

United States Patent Office Action for U.S. Appl. No. 11/403,606 dated Apr. 28, 2009 (9 pages).

United States Patent Office Action for U.S. Appl. No. 11/403,763 dated Apr. 29, 2009 (9 pages).

1

3

4

2

5

12

13

6

285

283

287

289

286

288

292

291

290

293

301

297

296

312

310

330

317

DNA-PK INHIBITORS

CROSS-REFERENCE TO RELATED APPLICATIONS

This application is a divisional of U.S. patent application Ser. No. 10/486,816, filed Feb. 13, 2004, now U.S. Pat. No. 7,226,918, which is a national stage filing under 35 U.S.C. §371 of PCT/GB02/03781, filed Aug. 14, 2002, which claims foreign priority benefits of United Kingdom Application No. 0119865.4, filed Aug. 14, 2001. These are incorporated herein by reference in their entirety.

NAMES OF PARTIES TO A JOINT RESEARCH AGREEMENT

The subject matter disclosed in this patent application was developed under a joint research agreement between Kudos Pharmaceuticals Ltd. and Cancer Research Technology Ltd., formerly known as Cancer Research Campaign Technology Ltd.

The present invention relates to compounds which act as DNA-PK inhibitors, their use and synthesis.

The DNA-dependent protein kinase (DNA-PK) is a nuclear serine/threonine protein kinase that is activated upon association with DNA. Biochemical and genetic data have revealed this kinase to be composed of a large catalytic subunit, termed DNA-PKcs, and a regulatory component termed Ku. DNA-PK has been shown to be a crucial component of both the DNA double-strand break (DSB) repair machinery and the V(D)J recombination apparatus. In addition, recent work has implicated DNA-PK components in a variety of other processes, including the modulation of chromatin structure and telomere maintenance (Smith, G. C. M. and Jackson, S. P., *Genes and Dev.* 13: 916-934 (1999)).

Human DNA is constantly under attack from reactive oxygen intermediates principally from by-products of the oxidative metabolism we have evolved for energy supply. Reactive oxygen species are capable of producing DNA single-strand breaks and, where two of these are generated in close proximity, DNA double strand breaks (DSBs). In addition, single- and double-strand breaks can be induced when a DNA replication fork encounters a damaged template, and are generated by exogenous agents such as ionising radiation (IR) and certain anti-cancer drugs (e.g. bleomycin). DSBs also occur as intermediates in site-specific V(D)J recombination, a process that is critical for the generation of a functional vertebrate immune system. If DNA DSBs are left unrepaired or are repaired inaccurately, mutations and/or chromosomal aberrations are induced, which in turn may lead to cell death. To combat the serious threats posed by DNA DSBs, eukaryotic cells have evolved several mechanisms to mediate their repair. In higher eukaryotes, the predominant of these mechanisms is DNA non-homologous end-joining (NHEJ), also known as illegitimate recombination. DNA-PK plays a key role in this pathway.

Biochemical studies on DNA-PK revealed that it is activated most potently by DNA DSBs, suggesting that it might play a role in recognising DNA damage. This stimulated investigations into the potential role of DNA-PKcs and Ku in DNA repair and led to the identification of cell lines which are radiosensitive due to mutations in DNA-PK components (Smith and Jackson, 1999). Cloning of the DNA-PKcs cDNA revealed that it corresponds to a ~470 kDa polypeptide, the N-terminal ~3500 amino acid residues of which does not appear to have significant homology to other characterised proteins (Hartley, K. O., et al., *Cell* 82: 849-856 (1995)). More significantly, the C-terminal ~500 amino acid residues of DNA-PKcs comprises a catalytic domain that falls into the PI 3-kinase family. Although this initially suggested that DNA-PK might be capable of phosphorylating inositol phospho-lipids, like certain well-characterised members of the PI 3-kinase family (Toker, A. and Cantley, L. C., *Nature* 387: 673-676 (1997)), the available evidence indicates that DNA-PK has protein but not lipid kinase activity (Hartley et al. 1995; Smith et al., 1999). At a similar time to the cloning of the DNA-PKcs cDNA, the genes and cDNAs for a range of other large PI 3-kinase like (PIKL) proteins were identified and cloned (Jackson, S. P., *Cancer Surv.* 28: 261-279 (1996)). These proteins have been shown to be involved in controlling transcription, the cell-cycle and/or genome stability in organisms from yeast to man. DNA-PKcs appears to be restricted to higher eukaryotes.

Besides DNA-PKcs, probably the best characterised member of the PIKL family is ATM, the protein deficient in the human neurodegenerative and cancer predisposition condition ataxia-telangiectasia (A-T; Lavin, M. F. and Shiloh, Y., *Annu. Rev. Immunol.* 15: 177-202 (1997)). ATM has been linked intimately to the detection and signalling of DNA damage.

It also has been previously found that the PI 3-kinase inhibitor LY294002:

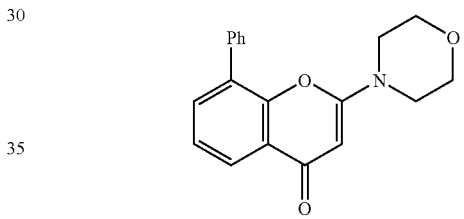

is able to inhibit DNA-PK function in vitro (Izzard, R. A., et al., *Cancer Res.* 59: 2581-2586 (1999)). The $IC_{50}$ (concentration at which 50% of enzyme activity is lost) for LY294002 towards DNA-PK is, at ~1 µM, the same as that for PI 3-kinase. Furthermore it has been shown that LY294002 is also able to weakly sensitise cells to the effects of IR (Rosenzweig, K. E., et al., *Clin. Cancer Res.* 3: 1149-1156 (1999)).

Given the involvement of DNA-PK in DNA repair processes, and that LY294002 has been shown to radiosensitise mammalian cells in culture, an application of (specific) DNA-PK inhibitory drugs would be to act as agents that will enhance the efficacy of both cancer chemotherapy and radiotherapy. DNA-PK inhibitors may also prove useful in the treatment of retroviral mediated diseases. For example it has been demonstrated that loss of DNA-PK activity severely represses the process of retroviral integration (Daniel R, et al., *Science*, 284:644-7 (1999)). DNA-PK inhibitors may also have potential as modulators of the immune system. DNA-PK has also been shown to play an important role in telomere maintenance, and hence inhibitors of DNA-PK may play a role in modulating telomere functions (Goytisolo, et al, *Mol. Cell. Biol.*, 21:3642-3651 (2001).

The present inventors have now discovered compounds which exhibit inhibition of DNA-PK; these compounds also exhibit selective inhibition of DNA-PK over the PI 3-kinase family members PI 3-kinase and ATM.

Accordingly, the first aspect of the invention provides for the use of compounds of formula I:

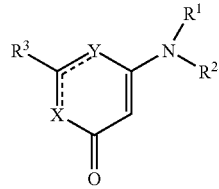

(I)

and isomers, salts, solvates, chemically protected forms, and prodrugs thereof, in the preparation of a medicament for inhibiting the activity of DNA-PK, wherein:

$R^1$ and $R^2$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms;

X and Y are selected from $CR^4$ and O, O and $CR'^4$ and $NR'^4$ and N, where the unsaturation is in the appropriate place in the ring, and where one of $R^3$ and $R^4$ or $R'^4$ is an optionally substituted $C_{3-20}$ heteroaryl or $C_{5-20}$ aryl group, and the other of $R^3$ and $R^4$ or $R'^4$ is H, or $R^3$ and $R^4$ or $R''^4$ together are —A—B—, which collectively represent a fused optionally substituted aromatic ring;

except that when X and Y are $CR^4$ and O, $R^3$ and $R^4$ together form a fused benzene ring, and $R^1$ and $R^2$ together with the N to which they are attached form a morpholino group, then the fused benzene does not bear as a sole substituent a phenyl substituent at the 8-position.

Thus, the three different possibilities for X and Y results in compounds of formulae Ia, Ib and Ic:

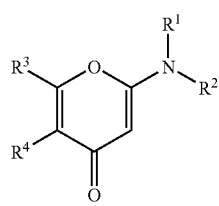

(Ia)

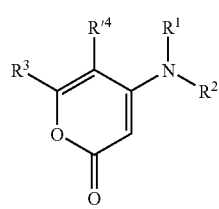

(Ib)

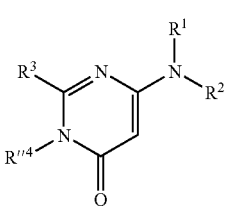

(Ic)

One aspect of the first aspect of the present invention relates to compounds of formulae Ia or Ib, where one $R^3$ and $R^4$ (or $R'^4$) is a $C_{3-20}$ heteroaryl or $C_{5-20}$ aryl group, and the other of $R^3$ and $R^4$ (or $R'^4$) is H.

Another aspect of the first aspect of the present invention relates to compounds of formulae Ia and Ic, where $R^3$ and $R^4$ or $R''^4$ together are —A—B—, which collectively represent a fused optionally substituted aromatic ring, with the proviso given above.

It is preferred that the medicament of the first aspect selectivity inhibits the activity of DNA-PK compared to PI 3-kinase and/or ATM. Selectivity is an important issue as inhibition of other PI 3-kinase family members may lead to unwanted side-effects associated with the loss of function of those enzymes.

A second aspect of the invention provides for the use of compounds as defined in the first aspect of the invention in the preparation of a medicament for use as an adjunct in cancer therapy or for potentiating tumour cells for treatment with ionising radiation or chemotherapeutic agents.

A third aspect of the invention provides for the use of compounds in the preparation of a medicament for the treatment of retroviral mediated diseases or disease ameliorated by the inhibition of DNA-PK.

A further aspect of the invention provides an active compound as described herein for use in a method of treatment of the human or animal body, preferably in the form of a pharmaceutical composition.

Another aspect of the invention provides a method of inhibiting DNA-PK in vitro or in vivo, comprising contacting a cell with an effective amount of an active compound as described herein.

A further aspect of the present invention provides novel compounds as described herein.

DEFINITIONS

The term "aromatic ring" is used herein in the conventional sense to refer to cyclic aromatic rings, that is, cyclic structures having 5 to 7 atoms in a ring with delocalised n-electron orbitals. Preferably, aromatic rings are those which meet Hückel's 4n+2 rule, ie. where the number of n-electrons is 4n+2, n representing the number of ring atoms. It is preferred that the aromatic ring has six atoms. In such a case, it is further preferred that the four atoms additional to the core moiety that make up the aromatic ring are all carbon, which yields compounds of the following general structure:

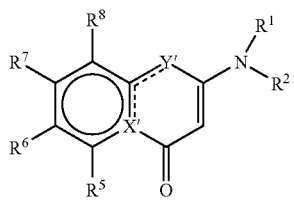

wherein X' and Y' are either C and O or N and N, respectively; and where $R^5$, $R^6$, $R^7$, and $R^8$ are preferably independently selected from hydrogen, $C_{1-7}$ alkyl, $C_{3-20}$ heterocyclyl, $C_{5-20}$ aryl, hydroxy, $C_{1-7}$ alkoxy (including $C_{1-7}$ alkyl-$C_{1-7}$ alkoxy and $C_{3-20}$ aryl-$C_{1-7}$ alkoxy) and acyloxy or adjacent pairs of substituents (i.e. $R^5$ and $R^6$, $R^6$ and $R^7$, $R^7$ and $R^8$) form, together with the atoms to which they are attached, an optionally substituted aromatic or carbocyclic ring.

The fused aromatic ring represented by —A—B— may be substituted by one or more of the following groups: $C_{1-7}$ alkyl, $C_{3-20}$ heterocyclyl, $C_{5-20}$ aryl, hydroxy, $C_{1-7}$ alkoxy (including $C_{1-7}$ alkyl-$C_{1-7}$ alkoxy and $C_{3-20}$ aryl-$C_{1-7}$ alkoxy) and acyloxy; adjacent pairs of substituents may form, together with the atoms to which they are attached, an optionally substituted aromatic or carbocyclic ring.

The term carbocyclic ring refers to a ring formed from 5 to 7 covalently linked carbon atoms. The ring may contain one or more carbon-carbon double bonds. Examples of carbocyclic rings include cyclopentane, cyclohexane, cycloheptane, cyclopentene, cyclohexene and cycloheptene.

$C_{1-7}$ alkyl: The term "$C_{1-7}$ alkyl", as used herein, pertains to a monovalent moiety obtained by removing a hydrogen atom from a $C_{1-7}$ hydrocarbon compound having from 1 to 7 carbon atoms, which may be aliphatic or alicyclic, or a combination thereof, and which may be saturated, partially unsaturated, or fully unsaturated.

Examples of saturated linear $C_{1-7}$ alkyl groups include, but are not limited to, methyl, ethyl, n-propyl, n-butyl, and n-pentyl (amyl).

Examples of saturated branched $C_{1-7}$ alkyl groups include, but are not limited to, iso-propyl, iso-butyl, sec-butyl, tert-butyl, and neo-pentyl.

Examples of saturated alicyclic $C_{1-7}$ alkyl groups (also referred to as "$C_{3-7}$ cycloalkyl" groups) include, but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of unsaturated $C_{1-7}$ alkyl groups which have one or more carbon-carbon double bonds (also referred to as "$C_{2-7}$alkenyl" groups) include, but are not limited to, ethenyl (vinyl, —CH=$CH_2$), 2-propenyl (allyl, —CH—CH=$CH_2$), isopropenyl (—C($CH_3$)=$CH_2$), butenyl, pentenyl, and hexenyl.

Examples of unsaturated $C_{1-7}$ alkyl groups which have one or more carbon-carbon triple bonds (also referred to as "$C_{2-7}$ alkynyl" groups) include, but are not limited to, ethynyl (ethinyl) and 2-propynyl (propargyl).

Examples of unsaturated alicyclic (carbocyclic) $C_{1-7}$ alkyl groups which have one or more carbon-carbon double bonds (also referred to as "$C_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

$C_{3-20}$ heterocyclyl: The term "$C_{3-20}$ heterocyclyl", as used herein, pertains to a monovalent moiety obtained by removing a hydrogen atom from a ring atom of a $C_{3-20}$ heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "$C_{3-20}$" denotes ring atoms, whether carbon atoms or heteroatoms.

Examples of $C_{3-20}$ heterocyclyl groups having one nitrogen ring atom include, but are not limited to, those derived from aziridine, azetidine, pyrrolidines (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine.

Examples of $C_{3-20}$ heterocyclyl groups having one oxygen ring atom include, but are not limited to, those derived from oxirane, oxetane, oxolane (tetrahydrofuran), oxole (dihydrofuran), oxane (tetrahydropyran), dihydropyran, pyran ($C_6$), and oxepin. Examples of substituted $C_{3-20}$ heterocyclyl groups include sugars, in cyclic form, for example, furanoses and pyranoses, including, for example, ribose, lyxose, xylose, galactose, sucrose, fructose, and arabinose.

Examples of $C_{3-20}$ heterocyclyl groups having one sulphur ring atom include, but are not limited to, those derived from thiirane, thietane, thiolane (tetrahydrothiophene), thiane (tetrahydrothiopyran), and thiepane.

Examples of $C_{3-20}$ heterocyclyl groups having two oxygen ring atoms include, but are not limited to, those derived from dioxolane, dioxane, and dioxepane.

Examples of $C_{3-20}$ heterocyclyl groups having two nitrogen ring atoms include, but are not limited to, those derived from imidazolidine, pyrazolidine (diazolidine), imidazoline, pyrazoline (dihydropyrazole), and piperazine.

Examples of $C_{3-20}$ heterocyclyl groups having one nitrogen ring atom and one oxygen ring atom include, but are not limited to, those derived from tetrahydrooxazole, dihydrooxazole, tetrahydroisoxazole, dihydroisoxazole, morpholine, tetrahydrooxazine, dihydrooxazine, and oxazine.

Examples of $C_{3-20}$ heterocyclyl groups having one oxygen ring atom and one sulphur ring atom include, but are not limited to, those derived from oxathiolane and oxathiane (thioxane).

Examples of $C_{3-20}$ heterocyclyl groups having one nitrogen ring atom and one sulphur ring atom include, but are not limited to, those derived from thiazoline, thiazolidine, and thiomorpholine.

Other examples of $C_{3-20}$ heterocyclyl groups include, but are not limited to, oxadiazine and oxathiazine.

Examples of heterocyclyl groups which additionally bear one or more oxo (=O) groups, include, but are not limited to, those derived from:

$C_5$ heterocyclics, such as furanone, pyrone, pyrrolidone (pyrrolidinone), pyrazolone (pyrazolinone), imidazolidone, thiazolone, and isothiazolone;

$C_6$ heterocyclics, such as piperidinone (piperidone), piperidinedione, piperazinone, piperazinedione, pyridazinone, and pyrimidinone (e.g., cytosine, thymine, uracil), and barbituric acid;

fused heterocyclics, such as oxindole, purinone (e.g., guanine), benzoxazolinone, benzopyrone (e.g., coumarin);

cyclic anhydrides (—C(=O)—O—C(=O)— in a ring), including but not limited to maleic anhydride, succinic anhydride, and glutaric anhydride;

cyclic carbonates (—O—C(=O)—O— in a ring), such as ethylene carbonate and 1,2-propylene carbonate;

imides (—C(=O)—NR—C(=O)— in a ring), including but not limited to, succinimide, maleimide, phthalimide, and glutarimide;

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam, γ-butyrolactam (2-pyrrolidone), δ-valerolactam, and ε-caprolactam;

cyclic carbamates (—O—C(=O)—NR— in a ring), such as 2-oxazolidone;

cyclic ureas (—NR—C(=O)—NR— in a ring), such as 2-imidazolidone and pyrimidine-2,4-dione (e.g., thymine, uracil).

$C_{5-20}$ aryl: The term "$C_{5-20}$ aryl", as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups", in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), naphthacene ($C_{18}$) and pyrene ($C_{16}$).

Examples of aryl groups which comprise fused rings, one of which is not an aromatic ring, include, but are not limited to, groups derived from indene and fluorene.

Alternatively, the ring atoms may include one or more heteroatoms, including but not limited to oxygen, nitrogen, and sulphur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine), triazine, tetrazole, and oxadiazole (furazan).

Examples of $C_{5-20}$ heterocyclic groups (some of which are $C_{5-20}$ heteroaryl groups) which comprise fused rings, include, but are not limited to, $C_9$ heterocyclic groups derived from benzofuran, isobenzofuran, indole, isoindole, purine (e.g., adenine, guanine), benzothiophene, benzimidazole; $C_{10}$ heterocyclic groups derived from quinoline, isoquinoline, benzodiazine, pyridopyridine, quinoxaline; $C_{13}$ heterocyclic groups derived from carbazole, dibenzothiophene, dibenzofuran; $C_{14}$ heterocyclic groups derived from acridine, xanthene, phenoxathiin, phenazine, phenoxazine, phenothiazine.

The above $C_{1-7}$ alkyl, $C_{3-20}$ heterocyclyl, and $C_{5-20}$ aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

$C_{1-7}$ alkoxy: —OR, wherein R is a $C_{1-7}$ alkyl group. Examples of $C_{1-7}$ alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam (2-pyrrolidone), δ-valerolactam, and ε-caprolactam.

Imino (imine): =NR, wherein R is an imino substituent, for example, hydrogen, $C_{1-7}$ alkyl group, a $C_{3-20}$ heterocyclyl group, or a $C_{5-20}$ aryl group, preferably hydrogen or a $C_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R$^2$ is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl and phthalimidyl:

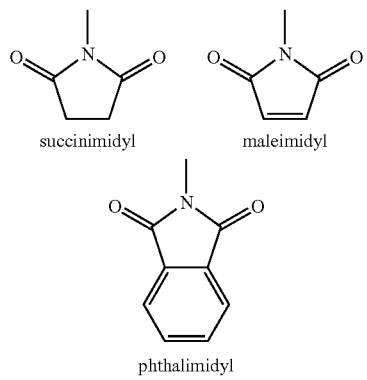

Acylureido: —N(R$^1$)C(O)NR$^2$C(O)R$^3$ wherein R$^1$ and R$^2$ are independently ureido substituents, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. R$^3$ is an acyl group as defined for acyl groups. Examples of acylureido groups include, but are not limited to, —NHCONHC(O)H, —NHCONMeC(O)H, —NHCONEtC(O)H, —NHCON-MeC(O)Me, —NHCONEtC(O)Et, —NMeCONHC(O)Et, —NMeCONHC(O)Me, —NMeCONHC(O)Et, —NMe-CONMeC(O)Me, —NMeCONEtC(O)Et, and —NMe-CONHC(O)Ph.

Carbamate: —NR$^1$—C(O)—OR$^2$ wherein R$^1$ is an amino substituent as defined for amino groups and R$^2$ is an ester group as defined for ester groups. Examples of carbamate groups include, but are not limited to, —NH—C(O)—O-Me, —NMe-C(O)—O-Me, —NH—C(O)—O-Et, —NMe-C(O)—O-t-butyl, and —NH—C(O)—O-Ph.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Tetrazolyl: a five membered aromatic ring having four nitrogen atoms and one carbon atom,

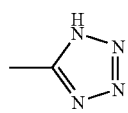

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$alkyl group, or, in the case of a "cyclic" amino group, R$^1$ and R$^2$, taken together with the nitrogen atom to which they are attached, form a heterocyclic ring having from 4 to 8 ring atoms. Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a C$_{1-7}$ alkyl group, a C$_{3-20}$ heterocyclyl group, or a C$_{5-20}$ aryl group, preferably H or a C$_{1-7}$ alkyl group.

Amidine: —C(=NR)NR$_2$, wherein each R is an amidine substituent, for example, hydrogen, a C$_{1-7}$alkyl group, a C$_{3-20}$ heterocyclyl group, or a C$_{5-20}$ aryl group, preferably H or a C$_{1-7}$ alkyl group. An example of an amidine group is —C(=NH)NH$_2$.

Carbazoyl (hydrazinocarbonyl): —C(O)—NN—R$^1$ wherein R$^1$ is an amino substituent as defined for amino groups. Examples of azino groups include, but are not limited to, —C(O)—NN—H, —C(O)—NN-Me, —C(O)—NN-Et, —C(O)—NN-Ph, and —C(O)—NN—CH$_2$-Ph.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.

Thioether (sulfide): —SR, wherein R is a thioether substituent, for example, a C$_{1-7}$ alkyl group (also referred to as a C$_{1-7}$ alkylthio group), a C$_{3-20}$ heterocyclyl group, or a C$_{5-20}$ aryl group, preferably a C$_{1-7}$ alkyl group. Examples of C$_{1-7}$ alkylthio groups include, but are not limited to, —SCH$_3$ and —SCH$_2$CH$_3$.

Disulfide: —SS—R, wherein R is a disulfide substituent, for example, a C$_{1-7}$ alkyl group, a C$_{3-20}$ heterocyclyl group, or a C$_{5-20}$ aryl group, preferably a C$_{1-7}$ alkyl group (also referred to herein as C$_{1-7}$ alkyl disulfide). Examples of C$_{1-7}$ alkyl disulfide groups include, but are not limited to, —SSCH$_3$ and —SSCH$_2$CH$_3$.

Sulfone (sulfonyl): —S(=O)$_2$R, wherein R is a sulfone substituent, for example, a C$_{1-7}$ alkyl group, a C$_{3-20}$ heterocyclyl group, or a C$_{5-20}$ aryl group, preferably a C$_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$, —S(=O)$_2$C$_4$F$_9$ (nonaflyl), —S(=O)$_2$CH$_2$CF$_3$ (tresyl), —S(=O)$_2$Ph (phenylsulfonyl), 4-methylphenylsulfonyl (tosyl), 4-bromophenylsulfonyl (brosyl), and 4-nitrophenyl (nosyl).

Sulfine (sulfinyl, sulfoxide): —S(=O)R, wherein R is a sulfine substituent, for example, a C$_{1-7}$ alkyl group, a C$_{3-20}$ heterocyclyl group, or a C$_{5-20}$ aryl group, preferably a C$_{1-7}$ alkyl group. Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfonyloxy groups include, but are not limited to, —OS(=O)$_2$CH$_3$ and —OS(=O)$_2$CH$_2$CH$_3$.

Sulfinyloxy: —OS(=O)R, wherein R is a sulfinyloxy substituent, for example, a C$_{1-7}$ alkyl group, a C$_{3-20}$ heterocyclyl group, or a C$_{5-20}$ aryl group, preferably a C$_{1-7}$ alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$) S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$ alkyl group, a C$_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$. A special class of sulfonamino groups are those derived from sultams—in these groups one of R$^1$ and R is a $C_{5-20}$ aryl group, preferably phenyl, whilst the other of R$^1$ and R is a bidentate group which links to the $C_{5-20}$ aryl group, such as a bidentate group derived from a $C_{1-7}$ alkyl group. Examples of such groups include, but are not limited to:

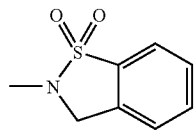

2,3-dihydro-tenzo[d]isothiazole-1,1-dioxide-2-yl

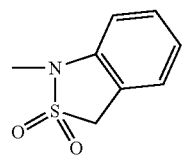

1,3-dihydro-benzo[c]isothiazole-2,2-dioxide-1-yl

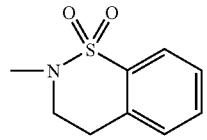

3,4-dihydro-2H-benzo[e][1,2]thiazine-1,1-dioxide-2-yl

Phosphoramidite: —OP(OR$^1$)—NR$_{22}$, where R$^1$ and R$^2$ are phosphoramidite substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr) 2.

Phosphoramidate: —OP(=O) (OR$^1$)—NR$_{22}$, where R$^1$ and R$^2$ are phosphoramidate substituents, for example, —H, a (optionally substituted) $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphoramidate groups include, but are not limited to, —OP(=O)(OCH$_2$CH$_3$)—N(CH$_3$)$_2$, —OP(=O) (OCH$_2$CH$_3$)—N(i-Pr)$_2$, and —OP(=O) (OCH$_2$CH$_2$CN)—N(i-Pr)$_2$.

In many cases, substituents may themselves be substituted. For example, a $C_{1-7}$ alkoxy group may be substituted with, for example, a $C_{1-7}$ alkyl (also referred to as a $C_{1-7}$ alkyl-$C_{1-7}$ alkoxy group), for example, cyclohexylmethoxy, a $C_{3-20}$ heterocyclyl group (also referred to as a $C_{5-20}$ aryl-$C_{1-7}$ alkoxy group), for example phthalimidoethoxy, or a $C_{5-20}$ aryl group (also referred to as a $C_{5-20}$ aryl-$C_{1-7}$alkoxy group), for example, benzyloxy.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/ amidine, nitroso/oxime, thioketone/enethiol, N-nitroso/hyroxyazo, and nitro/aci-nitro.

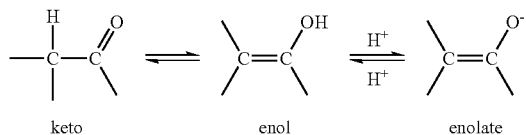

keto   enol   enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including 16O and 18O; and the like.

Unless otherwise specified, a reference to a particular compound includes all such isomeric forms, including (wholly or partially) racemic and other mixtures thereof. Methods for the preparation (e.g. asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts", *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al³⁺. Examples of suitable organic cations include, but are not limited to, ammonium ion (i.e., NH₄⁺) and substituted ammonium ions (e.g., NH₃R⁺, NH₂R₂⁺, NHR₃⁺, NR₄⁺). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH₃)₄⁺.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulphuric, sulphurous, nitric, nitrous, phosphoric, and phosphorous. Examples of suitable organic anions include, but are not limited to, those derived from the following organic acids: acetic, propionic, succinic, glycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, phenylsulfonic, toluenesulfonic, methanesulfonic, ethanesulfonic, ethane disulfonic, oxalic, pantothenic, isethionic, valeric, lactobionic, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form.

The term "chemically protected form", as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1999).

For example, a hydroxy group may be protected as an ether (—OR) or an ester (—OC(═O)R), for example, as: a t-butyl ether; a benzyl, benzhydryl(diphenylmethyl), or trityl (triphenylmethyl)ether; a trimethylsilyl or t-butyldimethylsilyl ether; or an acetyl ester (—OC(═O)CH₃, —OAc).

For example, an aldehyde or ketone group may be protected as an acetal or ketal, respectively, in which the carbonyl group (>C═O) is converted to a diether (>C(OR)₂), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH₃); a benzyloxy amide (—NHCO—OCH₂C₆H₅, —NH-Cbz); as a t-butoxy amide (—NHCO—OC(CH₃)₃, —NH-Boc); a 2-biphenyl-2-propoxy amide (—NHCO—OC(CH₃)₂C₆H₄C₆H₅, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO$).

For example, a carboxylic acid group may be protected as an ester for example, as: an $C_{1-7}$ alkyl ester (e.g. a methyl ester; a t-butyl ester); a $C_{1-7}$ haloalkyl ester (e.g., a $C_{1-7}$ trihaloalkyl ester); a tri$C_{1-7}$ alkylsilyl-$C_{1-7}$ alkyl ester; or a $C_{5-20}$ aryl-$C_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH₂NHC(═O)CH₃).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(═O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is $C_{1-7}$ alkyl (e.g. -Me, -Et); $C_{1-7}$ aminoalkyl (e.g. aminoethyl; 2-(N,N-diethylamino)ethyl; 2-(4-morpholino) ethyl); and acyloxy-$C_{1-7}$ alkyl (e.g. acyloxymethyl; acyloxyethyl; e.g. pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl) carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Selective Inhibition

'Selective inhibition' means the inhibition of one enzyme to a greater extent than the inhibition of one or more other enzymes. This selectivity is measurable by comparing the concentration of a compound required to inhibit 50% of the activity ($IC_{50}$) of one enzyme against the concentration of the same compound required to inhibit 50% of the activity ($IC_{50}$) of the other enzyme (see below). The result is expressed as a ratio. If the ratio is greater than 1, then the compound tested exhibits some selectivity in its inhibitory action.

The compounds of the present invention preferably exhibit a selectivity of greater than 3, 10, 20 or 50 against DNA-PK over PI 3-kinase.

The compounds of the present invention preferably exhibit a selectivity of greater than 5, 10, 50 or 100 against DNA-PK over ATM.

It is preferred that the $IC_{50}$s used to determine selectivity are determined using the methods described herein.

FURTHER PREFERENCES

Figure 1:
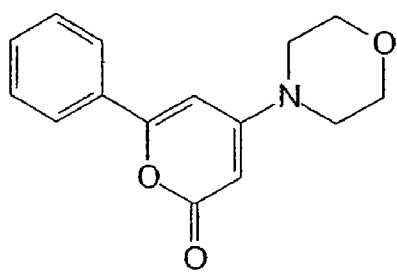
FIG. 1 shows the structure of preferred compounds of formula Ib.
Figure 1:
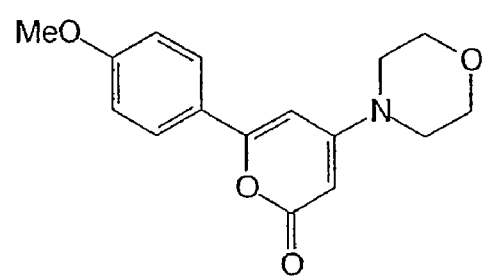
Figure 1:
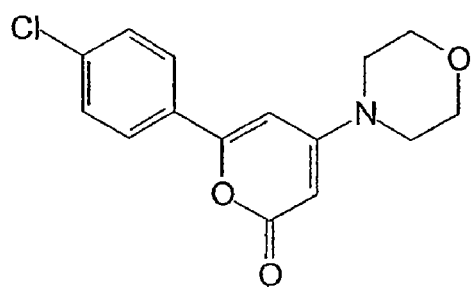
Figure 1:
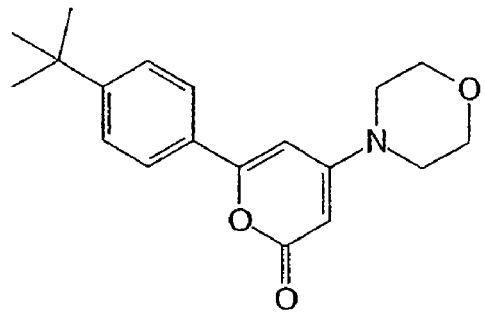

In formula I, when $R^1$ and $R^2$ form, along with the nitrogen atom to which they are attached, a heterocyclic ring having from 4 to 8 atoms, this may form part of a $C_{4-20}$ heterocyclyl group defined above (except with a minimum of 4 ring atoms), which must contain at least one nitrogen ring atom. It is preferred that $R^1$ and $R^2$ form, along with the nitrogen atom to which they are attached, a heterocyclic ring having 5, 6 or 7 atoms, more preferably 6 ring atoms.

Single rings having one nitrogen atom include azetidine, azetidine, pyrrolidine (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, and azepine; two nitrogen atoms include imidazolidine, pyrazolidine (diazolidine), imidazoline, pyrazoline (dihydropyrazole), and piperazine; one nitrogen and one oxygen include tetrahydrooxazole, dihydrooxazole, tetrahydroisoxazole, dihydroisoxazole, morpholine, tetrahydrooxazine, dihydrooxazine, and oxazine; one nitrogen and one sulphur include thiazoline, thiazolidine, and thiomorpholine.

Preferred rings are those containing one heteroatom in addition to the nitrogen, and in particular, the preferred heteroatoms are oxygen and sulphur. Thus preferred groups include morpholino, thiomorpholino, thiazolinyl. Preferred groups without a further heteroatom include pyrrolidino.

The most preferred groups are morpholino and thiomorpholino.

As mentioned above, these heterocyclic groups may themselves be substituted; a preferred class of substituent is a $C_{1-7}$ alkyl group. When the heterocyclic group is morpholino, the substituent group or groups are preferably methyl or ethyl, and more preferably methyl. A sole methyl substituent is most preferably in the 2 position.

As well as the single ring groups listed above, rings with bridges or cross-links are also envisaged. Examples of these types of ring where the group contains a nitrogen and an oxygen atom are:

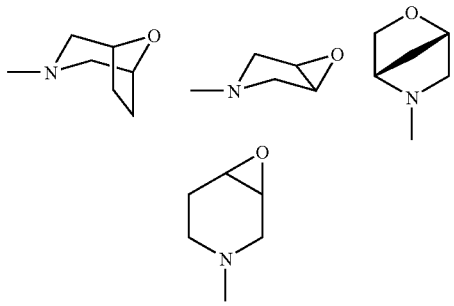

These are named 8-oxa-3-aza-bicyclo[3.2.1]oct-3-yl, 6-oxa-3-aza-bicyclo[3.1.0]hex-3-yl, 2-oxa-5-aza-bicyclo[2.2.1]hept-5-yl, and 7-oxa-3-aza-bicyclo[4.1.0]hept-3-yl, respectively.

The proviso as set in the first aspect of the invention preferably excludes compounds where X and Y are $CR^4$ and O, $R^3$ and $R^4$ together form a fused benzene ring, and $R^1$ and $R^2$ together with the N to which they are attached form a morpholino group, and the fused benzene does not bear as a sole substituent a substituent at the 8-position. An alternative preferred embodiment is to exclude compounds where X and Y are $CR^4$ and O, $R^3$ and $R^4$ together form a fused benzene ring, and $R^1$ and $R^2$ together with the N to which they are attached form a morpholino group, and the fused benzene does not bear a sole substituent that is a phenyl group.

Preferred Aspects of Compounds of Formula Ia

It is preferred that $R^1$ and $R^2$ in formula Ia together form a morpholino group.

In one preferred aspect of compounds of formula Ia, $R^4$ is preferably H. $R^3$ is preferably a $C_{5-20}$ aryl group, more preferably a $C_{5-20}$ carboaryl group, and in particular an optionally substituted phenyl group. Preferred substituents include halo (particularly fluoro and chloro), $C_{1-7}$ alkyl (particularly $C_1$, alkyl or t-butyl), ether, alkoxy (in particular methoxy), nitro, cyano, acyl, formyl, ester, acyloxy, hydroxy, carboxy, $C_{5-20}$ aryl (particularly phenyl), $C_{3-20}$ heterocyclyl, acylamido, acylureido, thioureido, carbamate, carbazoyl, amido, and amino.

When $R^3$ is $C_{5-20}$ aryl, examples of preferred groups include optionally substituted napthalene, quiniline, pyridine, indole, indazole, pyrazine, pyrrole, imidazole, thiophene, thiazole, benzo[b]thiophene, furan and benzofuran.

$R^3$ may be substituted with one or more substituents, preferably one substituent. Preferably $R^3$ is a mono substituted phenyl.

Where $R^3$ is a $C_{5-20}$ aryl group other than phenyl, preferred substituents include $C_{1-7}$ alkyl, formyl and ether (in particular alkoxy).

When $R^3$ is a $C_{3-20}$ aryl group, the substituents may be at any position on the aryl group. Accordingly, when $R^3$ is an optionally substituted phenyl the substituents may be at the ortho-(2-), meta-(3-) or para-(4-) position. It is generally preferred that the substituents are in the para- (or 4-) position. Preferably $R^3$ is a 4-substituted phenyl. The nature of the substituent is discussed below.

Preferred $R^3$ Substituents

A first group of preferred substituents include halo (particularly fluoro and chloro), $C_{1-7}$ alkyl (particularly t-butyl) and alkoxy (particularly methoxy).

Figure 3:
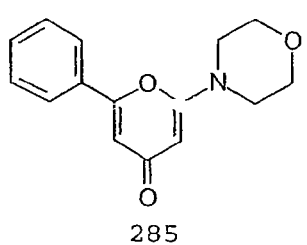
FIG. 3 shows the structure of preferred compounds of formula Ia.
Figure 3:
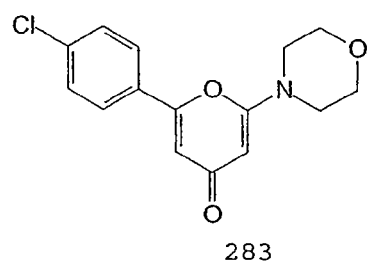
Figure 3:
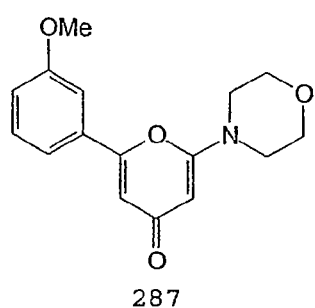
Figure 3:
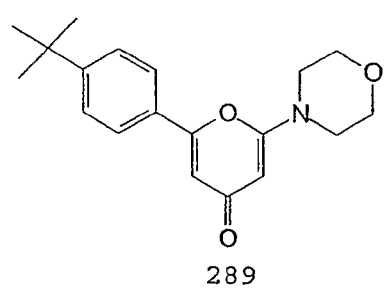
Figure 3:
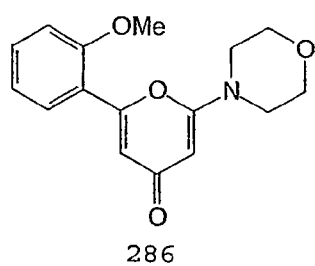
Figure 3:
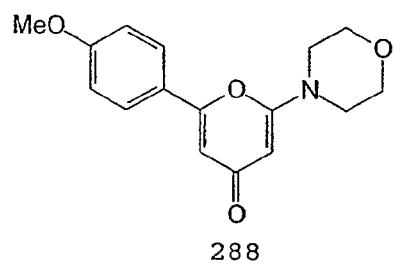
Figure 3:
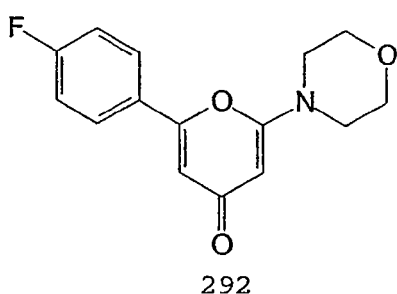
Figure 3:
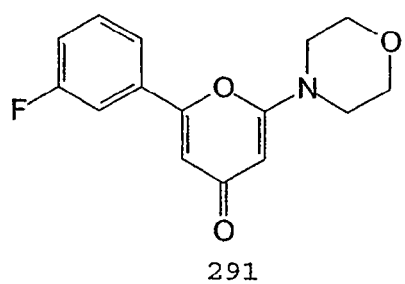
Figure 3:
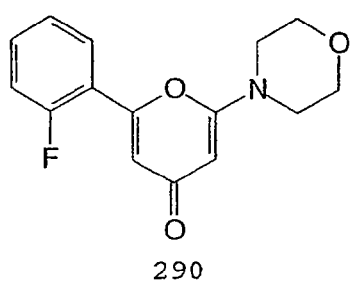

Preferred compounds of this type include 2-(morpholin-4-yl)-6-phenyl-pyran-4-one (Compound 285), 2-(4-chlorophenyl)-6-(morpholin-4-yl)-pyran-4-one (Compound 284), 2-(3-methoxyphenyl)-6-(morpholin-4-yl)-pyran-4-one (Compound 287), 2-(4-tert-butyl-phenyl)-6-(morpholin-4-yl)-pyran-4-one (Compound 289), 2-(2-methoxyphenyl)-6-(morpholin-4-yl)-pyran-4-one (Compound 286), 2-(4-Methoxyphenyl)-6-(morpholin-4-yl)-pyran-4-one (Compound 288), 6-(4-fluorophenyl)-2-(morpholin-4-yl)pyran-4-one (Compound 292), 6-(3-fluorophenyl)-2-(morpholin-4-yl)pyran-4-one (Compound 291) and 6-(2-fluorophenyl)-2-(morpholin-4-yl)pyran-4-one (Compound 290), with 6-(4-fluorophenyl)-2-(morpholin-4-yl)pyran-4-one (Compound 292) being the most preferred. (See FIG. 3).

Preferably the substituent is $C_{1-7}$ alkyl, and in particular $C_1$ alkyl or t-butyl. Preferably $R^3$ is substituted $C_{1-7}$ alkyl (i.e. $C_{1-7}$ alkylene), and preferred substituents are discussed below.

A second group of preferred substituents include acylamido, acylureido, thioureido, carbamate, carbazoyl, amido and amino.

In accordance with the definitions above, it is preferred that the amino, acyl, ester, acyloxy and amide groups of the preferred acylamido, acylureido, thioureido, carbamate, carbazoyl, amido and amino substituents are independently H, $C_{1-7}$ alkyl (including substituted $C_{1-7}$ alkyl, i.e. $C_{1-7}$ alkylene), $C_{5-20}$ aryl (including $C_{5-20}$ aralkyl), $C_{3-20}$ heterocycle or two of the groups form a heterocycle. Preferably the amino, acyl, ester, acyloxy and amide groups are independently H, $C_1$ alkyl, phenyl or heterocyclyl containing 3 to 7 ring atoms, or two or more groups form a heterocyclyl ring.

Where the amino, acyl, ester, acyloxy and amide groups of the second group of preferred substituents are $C_{5-20}$ aryl it is preferred that the $C_{5-20}$ aryl is phenyl, benzyl, pyridine, pyrimidine, oxazine, furan, thiophene, imidazole or oxazole. Where the amino, acyl, ester, acyloxy and amide groups of the second group of preferred substituents are $C_{3-20}$ heterocyclyl they preferably have 3 to 7 ring atoms and preferably contain from 1 to 4 ring heteroatoms.

Where two of the amino, acyl, ester, acyloxy and amide groups of the second group of preferred substituents form a heterocyclyl comprising a heteroatom from the preferred substituent, the heterocyclyl preferably comprises 3 to 7 ring members. Preferably the heterocyclyl contains from 1 to 4 ring heteroatoms. Examples of preferred heterocyclyls include those derived from piperazine and azepine, morpholine and thiomorpholine.

Further Substitution

In general, where $R^3$ of formula Ia is $C_{5-20}$ aryl group or $C_{5-20}$ carboaryl group, it is preferred that the $C_{5-20}$ aryl or $C_{5-20}$ carboaryl group is substituted. It is also preferred that when $R^3$ is optionally substituted phenyl, the optionally substituted phenyl group is itself further substituted. It is particularly preferred that the preferred $R^3$ substituents discussed above are further substituted (i.e. the $C_{1-7}$ alkyl, ether, alkoxy, acyl, ester, acyloxy, $C_{5-20}$ aryl, $C_{3-20}$ heterocyclyl, acylamido, acylureido, thioureido, carbamate, carbazoyl, amido, and amino are themselves further substituted). The further substitution may comprise any of the substituents or groups described herein but is preferably one or more of halo (in particular fluoro or chloro), nitro, cyano (in particular methyl- or ethylcyano), hydroxy, ester, ether, alkoxy (in particular methoxy), acyloxy, acyl, thioether, carboxy, amino (in particular —$NH_2$ and —$NMe_2$), $C_{5-20}$ aryl (in particular phenyl, thiophene and furan), thioether, carbamate, $C_{1-7}$ alkyl and $C_{3-20}$ heterocyclyl (in particular N-, O- and S-containing heterocyclyl including tetrahydrofuran, piperidine and pyrrolidine). Thus, for example, $R^3$ may be haloalkyl substituted phenyl, cyanoalkyl substituted phenyl or trifluoromethoxy substituted phenyl.

Accordingly, in a preferred class of compounds in which $R^3$ of formula Ia is $C_{1-7}$ alkyl substituted phenyl it is preferred that the alkyl substituent is further substituted (to form $C_{1-7}$ alkylene) by halo, amino, amido, acylamido, ester or acyloxy groups.

In the preferred class of compounds in which $R^3$ is a phenyl substituted with acylamido, acylureido, thioureido, carbamate, carbazoyl, amido or amino, it is preferred that these substituents are further substituted, preferably by halo (in particular fluoro or chloro), nitro, cyano (in particular methyl- or ethylcyano), hydroxy, ester, ether, acyloxy, acyl, thioether, carboxy, $C_{5-20}$ aryl, $C_{1-7}$ alkyl and $C_{3-20}$ heterocyclyl (in particular N-, O- and S-containing heterocyclyl).

In a preferred group of compounds in this preferred aspect of compounds of formula Ia $R^3$ is aminomethyl substituted phenyl, where the amino group is preferably further substituted as stated above. Preferably the aminomethyl group is at the 3- or 4-position on the phenyl.

In another preferred group of compounds in this preferred aspect of compounds of formula Ia $R^3$ is amido substituted phenyl, where the amido group is preferably further substituted as stated above. Preferably the amido group is at the 3- or 4-position on the phenyl.

In another preferred group of compounds in this preferred aspect of compounds of formula Ia $R^3$ is acylamido substituted phenyl, where the acylamido group is preferably further substituted as stated above. Preferably the acylamido group is at the 3- or 4-position on the phenyl.

In another preferred group of compounds in this preferred aspect of compounds of formula Ia $R^3$ is amino substituted phenyl, where the amino group is preferably further substituted as stated above. Preferably the amino group is at the 3- or 4-position on the phenyl.

In another preferred aspect of compounds of formula Ia, where $R^3$ and $R^4$ together are —A—B—, which collectively represent a fused aromatic ring which is benzene, it is preferred that the 5 position is unsubstituted (i.e. $R^5$=H) and that one or two of the 6, 7 and 8 positions are substituted. Preferably only one of the 6, 7 and 8 positions is substituted. Preferably the 7-position is substituted. Preferably the substituents are selected from halo (in particular bromo); ether (in particular aralkyl ethers and especially where the aryl is further substituted with halo, $C_{1-7}$ alkyl, alkoxy or nitro); $C_{5-20}$ aryl (in particular napth-1-yl and napth-2-yl) optionally substituted by $C_{1-7}$ alkyl (in particular methyl) including $C_{1-7}$ alkyl (in particular propyl) substituted by $C_{5-20}$ aryl (preferably phenyl); $C_{5-20}$ heteroaryl (in particular benzo[b]thiophen-3-yl, benzo[b]thiophen-2-yl, thiophen-3-yl, thiophen-2-yl, furan-2-yl, indol-6-yl, quinoline-8-yl, phenoxathiin-4-yl) optionally substituted by acyl (in particular 5-acetyl-thiophen-2-yl); $C_{3-20}$ heterocyclyl; amino; sulfonoxy (especially where the sulfonoxy substituent is haloalkyl, in particular $CF_3$).

In another preferred class of compounds in this preferred aspect of compounds of formula Ia, it is preferred that the fused benzene ring (i.e. —A—B—) is substituted at the 8-position with a $C_{3-20}$ heterocyclyl group. Preferably the heterocyclyl group is a tricyclic structure. Preferably the group comprises oxygen and/or sulfur heteroatoms and is based on the carbazole or anthracene system. Preferably a sulfur atom and/or oxygen atom is present in the central ring of the carbazole or anthracene systems.

In the preferred group of compounds where the 6, 7, or 8 substituent is phenyl, it is preferred that the phenyl is itself further substituted. Preferably the phenyl is mono substituted but it may also be di substituted. Preferred substitutents include ester (especially where the ester substituent is aralkyl, in particular benzyl, or $C_{1-7}$ alkyl, in particular methyl or ethyl); ether (especially where the ether substituent is $C_{1-7}$ alkyl, in particular methyl or trifluoromethyl, or arylalkyl, in particular benzyl); cyano; acyl (especially where the acyl substituent is $C_{1-7}$ alkyl, in particular methyl); $C_{5-20}$ aryl (in particular phenyl); acylamido (especially where the acyl substituent is $C_{1-7}$ alkyl, in particular methyl); halo (in particular chloro); $C_{1-7}$ alkyl (preferably methyl or ethyl) especially $C_{1-7}$ alkyl substituted by hydroxy, fluoro, acylamido (in particular phthalimidyl) and $C_{1-7}$ alkyl substituted with an ester with the ester substituent being $C_{1-7}$ alkyl; hydroxy; amido (in particular where both amino substituents are H); amino (in particular where both amino substituents are H); and carboxy.

In another preferred group of compounds, the 5, 6 and 8 positions are unsubstituted (i.e. $R^5$, $R^6$ and $R^8$=H), and the 7 position is substituted (i.e. $R^7$ is not H). More preferably, the substituent ($R^7$) is selected from hydroxy, $C_{1-7}$ alkoxy (including $C_{1-7}$ alkyl-$C_{1-7}$ alkoxy and $C_{3-20}$ aryl-$C_{1-7}$ alkoxy), and acyloxy, with $C_{3-20}$ aryl-$C_{1-7}$ alkoxy being the most preferred. In this group, the $C_{1-7}$ alkoxy is preferably either ethoxy, especially ethoxy substituted by optionally substituted aryl (in particular phenyl or pyridinyl), optionally substituted aryloxy (in particular phenoxy, napthyloxy), alkoxy, sulfonoxy (in particular where the sulfonoxy substituent is alkyl, such as methyl or ethyl, or aryl, such as phenyl), or $C_{1-7}$ alkoxy is —O—CH$_2$—, where the alkoxy substituent is preferably optionally substituted aryl (in particular phenyl or pyridinyl) and the $C_{3-20}$ aryl group is preferably optionally substituted phenyl, where the phenyl group being substituted is more preferred.

Figure 4:
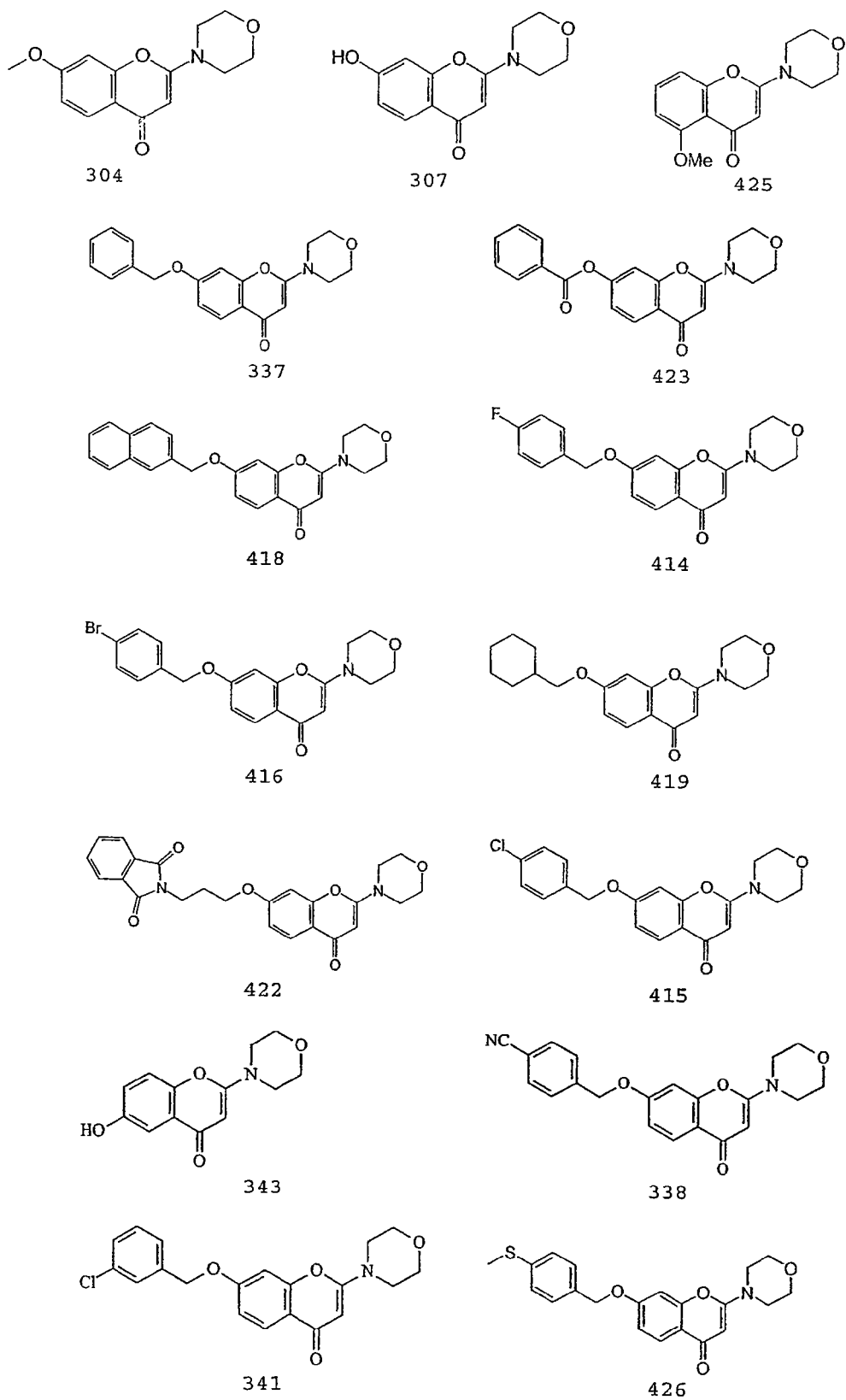
FIG. 4 shows the structures of further preferred compounds of formula Ia.

Preferred compounds of this type include 7-methoxy-2-morpholin-4-yl-benzo[h]chromen-4-one (Compound 304), 7-hydroxy-2-(morpholin-4-yl)-chromen-4-one (Compound 307), 7-Benzyloxy-2-morpholin-4-yl-chromen-4-one (Compound 337), 7-Benzoyloxy-2-morpholin-4-yl-chromen-4-one (Compound 423), 2-Morpholin-4-yl-7-(naphthalene-2-ylmethoxy)-chromen-4-one (Compound 418), 7-(4-Fluoro-benzyloxy)-2-morpholin-4-yl-chromen-4-one (Compound 414), 7-(4-Bromo-benzyloxy)-2-morpholin-4-yl-chromen-4-one (Compound 416), 7-Cyclohexylmethoxy-2-morpholin-4-yl-chromen-4-one (Compound 419), N-[3-(2-Morpholin-4-yl-4-oxo-4H-chromen-7-yloxy)-propyl]-isoindole-1,3-dione (Compound 422), 7-(2-Chloro-benzyloxy)-2-morpholin-4-yl-chromen-4-one (Compound 417), 7-(4-chlorobenzyloxy)-2-(morpholin-4-yl)-chromen-4-one (Compound 415), 7-(4-cyano-benzyloxy)-2-morpholin-4-yl-chromen-4-one (Compound 338), 7-(3-Chlorobenzyloxy)-2-(morpholin-4-yl)-chromen-4-one (Compound 341) and 7-(3-Methylbenzyloxy)-2-(morpholin-4-yl)-chromen-4-one (Compound 342). Of these benzyloxy-2-morpholin-4-yl-chromen-4-one (Compound 337), 7-(4-Bromo-benzyloxy)-2-morpholin-4-yl-chromen-4-one (Compound 416) and 7-(4-Chlorobenzyloxy)-2-(morpholin-4-yl)-chromen-4-one (Compound 415) are particularly preferred. (See FIG. 4).

In a further preferred aspect of formula Ia, where $R^3$ and $R^4$ together are —A—B—, which collectively represent a fused aromatic ring which is benzene, it is preferred that there is a further ring fused to the fused benzene ring, which further fused ring is preferably benzene or cyclohexane. These further fused rings may be in any position on the fused ring.

Figure 5:
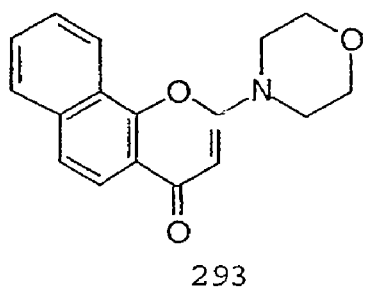
FIG. 5 shows the structures of further preferred compounds of formula Ia.
Figure 5:
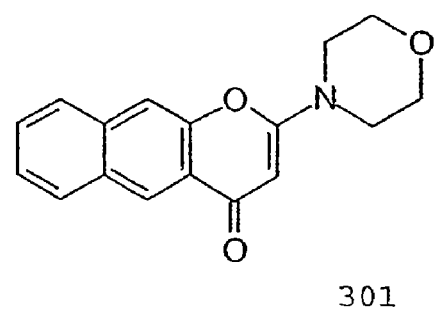
Figure 5:
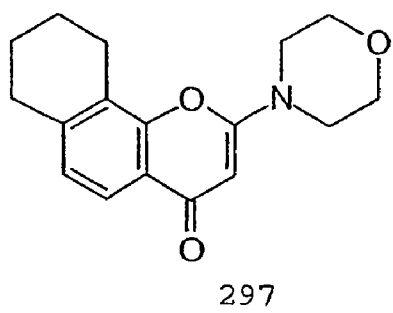
Figure 5:
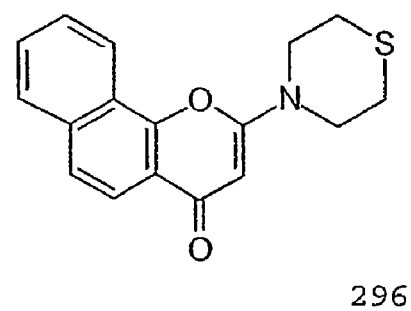
Figure 5:
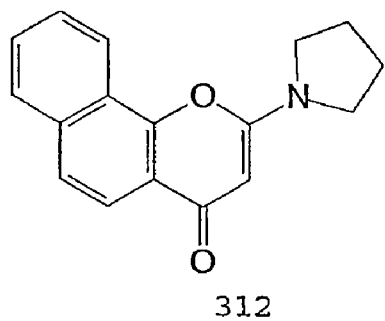
Figure 5:
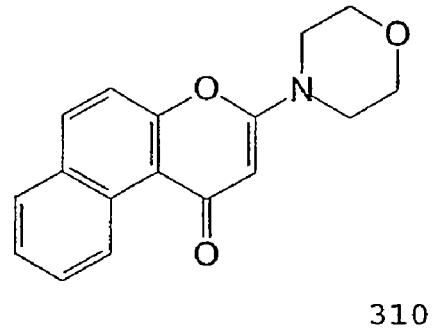
Figure 5:
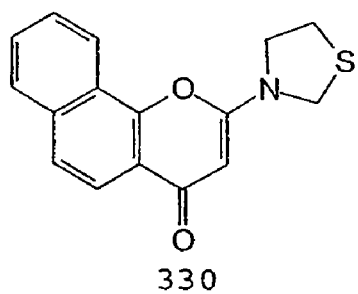
Figure 5:
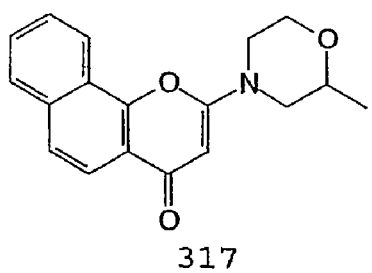

Preferred compounds of this type include 2-(morpholin-4-yl)-benzo[h]chromen-4-one (Compound 293), 2-(morpholin-4-yl)-benzo[g]chromen-4-one (Compound 301), 7,8,9,10-tetrahydro-benzo[h]-2-(morpholin-4-yl)-chromen-4-one (Compound 297), 2-(thiomorpholin-4-yl)-benzo[h]chromen-4-one (Compound 296), 2-pyrrolidin-1-yl-benzo[h]chromen-4-one (Compound 312), 2-morpholin-4-yl-benzo[f]chromen-4-one (Compound 310), 2-(Thiazolidin-3-yl)-benzo[h]chromen-4-one (Compound 330) and 2-(2-Methyl-morpholin-4-yl)-benzo[h]chromen-4-one (Compound 317), with 2-(2-Methyl-morpholin-4-yl)-benzo[h]chromen-4-one (Compound 317) being the most preferred. (See FIG. 5).

It is generally preferred in compounds of formula Ia where $R^3$ and $R^4$ together form —A—B— which represents a fused ring, that the amino group at the 2 position (i.e. $NR^1R^2$) is selected from dimethylmorpholino (in particular 3,5-dimethylmorpholino), methylmorpholino (in particular 3-methylmorpholino), 3,4-dihydro-2H-benzo[1,4]oxazin-4-yl, di(2-hydroxyethyl)amino, 2-(2-Hydroxy-ethoxy)-ethylamino or 2-(2-Bromo-phenoxy)-ethylamino.

Preferred Aspects of Compounds of Formula Ib

For compounds of formula Ib, $R^4$ is preferably H. $R^3$ is preferably a $C_{5-20}$ aryl group, more preferably a $C_{5-20}$ carboaryl group, and in particular an optionally substituted phenyl group. It is generally preferred that the substituents are in the para- (or 4-)position. Preferred substituents include halo, $C_{1-7}$ alkyl and alkoxy, and more preferably halo (particularly chloro) and alkoxy (particularly methoxy).

Preferred compounds of this type are 6-(4-methoxyphenyl)-4-morpholin-4-yl-pyran-2-one (Compound 3) and 6-(4-chlorophenyl)-4-morpholin-4-yl-pyran-2-one (Compound 4). (See FIG. 1).

Preferred Aspects of Compounds of Formula Ic

In a first preferred aspect of compounds of formula Ic, $R^3$ and $R^{"4}$ together are —A—B— which represents a fused aromatic ring which is pyridine, and the compounds are substituted at the 2-position, preferably with amino substituents. It is preferred that the amino groups are ethylmorpholino (in particular 3-ethylmorpholino), dimethylmorpholino (in particular 3-dimethylmorpholino), 2,5-dihydro-1H-pyrrol-1-yl, or pyrrolidin-1-yl.

In a second preferred aspect of compounds of formula Ic, where $R^3$ and $R'^4$ together are —A—B—, which collectively represent a fused aromatic ring which is pyridine, it is preferred that a further benzene ring is fused to the pyridine (at the 7 and 8 positions) to result in pyrimidino[2,1-a]isoquinoline-4-ones. The further benzene ring is preferably unsubstituted.

In this preferred aspect it is preferred that $R^1$ and R2 of formula Ic form morpholine, ethylmorpholine (in particular 3-ethylmorpholine), dihydropyrrole (in particular 2,5-dihydro-1H-pyrrol-1-yl or tetrahydropyrrole).

Figure 2:
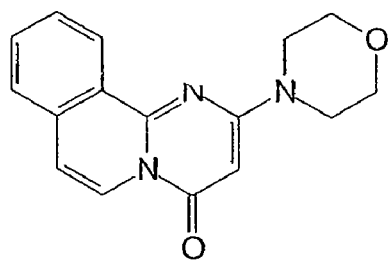
FIG. 2 shows the structure of preferred compounds of formula Ic.
Figure 2:
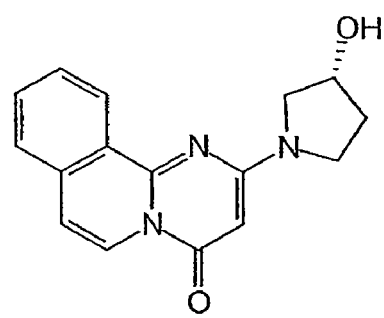
Figure 2:
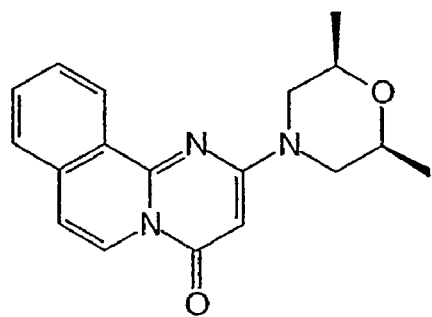
Figure 2:
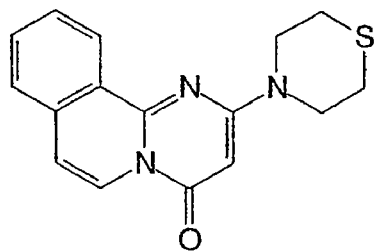

Preferred compounds of this type are 2-morpholin-1-yl-pyrimido-[2,1-a]isoquinolin-4-one (Compound 5), 2-((S)-3-Hydroxy-pyrrolin-1-yl)-pyrimido[2,1-a]isoquinolin-4-one (Compound 12), 2-((2S,6R)-2,6-Dimethyl-morpholin-4-yl)-pyrimido[2,1-a]isoquinolin-4-one (Compound 13) and 2-Thiomorpholin-4-yl-pyrimido[2,1-a]isoquinolin-4-one (Compound 6), with 2-morpholin-1-yl-pyrimido-[2,1-a]isoquinolin-4-one (Compound 5) being the most preferred. (See FIG. 2).

In a second preferred aspect of compounds of formula Ic, where $R^3$ and $R'^4$ together are —A—B—, which collectively represent a fused aromatic ring which is pyridine, it is preferred that the 5, 6 and 8 positions are unsubstituted (i.e. $R^5$, $R^6$ and $R^8$=H), and that the 7 position is substituted (i.e. $R^7$ is not H). More preferably, the substituent ($R^7$) is selected from hydroxy, $C_{1-7}$ alkoxy (including $C_{1-7}$ alkyl-$C_{1-7}$ alkoxy and $C_{3-20}$ aryl-$C_{1-7}$ alkoxy) and acyloxy, with $C_{3-20}$ aryl-$C_{1-7}$ alkoxy being the most preferred. In this group, the $C_{1-7}$ alkoxy is preferably —O—$CH_2$— and the $C_{3-20}$ aryl group is preferably optionally substituted phenyl.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether ($Et_2O$), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis Routes

Compounds as described in the first aspect of the invention can be synthesised by a number of methods, examples of some of which are given below.

Broadly, the synthetic strategy involves performing a cyclisation to form the central core followed by a coupling reaction such as a Suzuki reaction to add substituents to the core structure.

The key step in most of these synthesis routes is the formation of the central aromatic ring; this can be accomplished in numerous ways, as shown below, and include condensative cyclisation.

In many cases appropriate substitution can be present in the starting materials, although example of the further derivation of end products is also given.

Synthesis Route 1

Synthesis of 4-Morpholin-4-yl-6-(aryl)-pyran-2-ones

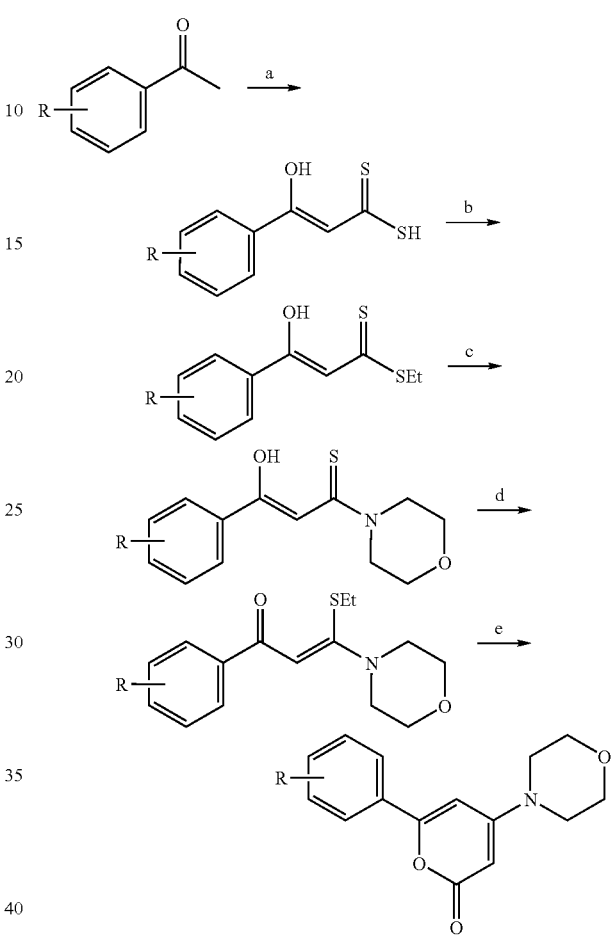

a t-BuOK, $CS_2$, THF;
b n-$Bu_4NHSO_4$, NaOH, EtI, DCM;
c morpholine, EtOH, reflux;
d EtI, $K_2CO_3$, acetone;
e ethyl bromoacetate, Zn, THF (a) 3-aryl-3-hydroxy-dithioacrylic acids A solution of $CS_2$ (1.81 ml, 30 mmol) and acetophenone derivative (30 mmol) in dry THF (20 ml) was added dropewise over 30 min to a well-stirred solution of potassium tert-butoxide (6.73 g, 60 mmol) in dry THF (50 ml) under $N_2$. A bright red coloration and the formation of a precipitate were observed. The mixture was left under vigorous stirring overnight and then was poured onto water (200 ml) and extracted with ether (3×100 ml). The aqueous layer was acidified with 2N $H_2SO_4$ to pH 1-2 (Watmann pH paper) and then extracted with ether (3×100 ml). The organics were dried over $Na_2SO_4$ and the solvent was evaporated in vacuo to give the desired compound.

(b) Ethyl 3-aryl-3-hydroxy-dithioacrylates

Tetrabutylammonium hydrogen sulphate (6.76 g, 20 mmol) and sodium hydroxide (21.6 g, 40 mmol) were dissolved in water (50 ml). A solution of 3-aryl-3-hydroxydithioacrylic acid (20 mmol) in dichloromethane (50 ml) was added to the solution in one portion and the reaction mixture was stirred vigorously for 30 min. The aqueous layer was removed and iodoethane (5 ml) was added to the dichloromethane solution that was then stirred for 1 h. The solvent was removed in vacuo and the residue taken into water (200 ml). The organic were extracted with ether (3×100 ml), dried over $Na_2SO_4$ and evaporated in vacuo. The residue was then purified by column chromatography (ethyl acetate:petroleum ether 40-60°, 1:4) to give the desired compound.

(c) 1-aryl-3-morpholin-4-yl-3-thioxo-propan-1-ones

Morpholine (1.31 ml, 15 mmol) was added to a solution of ethyl 3-aryl-3-hydroxy-dithioacrylate (15 mmol) in ethanol (20 ml). The reaction mixture was refluxed for 5 h and upon cooling at room temperature the desired compound crystallized. The compound was then isolated by filtration.

(d) 1-aryl-3-ethylsulfanyl-3-morpholin-4-yl-propen-1-ols 1-aryl-3-morpholin-4-yl-3-thioxo-propan-1-one (12 mmol) was dissolved in dry acetone (20 ml) and finely powdered $K_2CO_3$ (1.83 g, 13.2 mmol) and iodoethane (1.07 ml, 13.2 mmol) were added to the solution. The reaction mixture was then reflux overnight and the solvent was then removed in vacuo. The residue was taken into water (50 ml) and the organics were extracted with dichloromethane (3×30 ml), dried over sodium sulfate and evaporated in vacuo. The residue was purified by column chromatography to give the desired compound.

(e) 4-morpholin-4-yl-6-(aryl)-pyran-2-ones

A suspension of activated zinc (heated at 120° C. for 1 hr) (2.6 g, 0.04 g atom), ethyl bromoacetate (3.18 g, 20 mmol) and a few crystals of iodine in dry THF (30 ml) was heated at 50° C. for 45 min with stirring. A solution of the respective 1-aryl-3-ethylsulfanyl-3-morpholin-4-yl-propenone (10 mmol) in dry THF (50 ml) was added dropwise with stirring and the mixture was refluxed for 3-4 h. The mixture was then poured over-ice cold dilute 3% $H_2SO_4$ (100 ml), the aqueous layer was extracted with ethyl acetate (3×50 ml), the combined extract was dried over $Na_2SO_4$ and the solvent was evaporated. The residue was purified by column chromatography (ethyl acetate:pet ether 40-60, 1:4) to give the pure pyran-2-one.

Variations

If the amino group in the final product is desired to be other than morpholino, than the relevant amine can be used in step (c) in place of morpholine. The 6-aryl group in the final product can be a heteroaryl group, if the appropriate acetophenone derivative is used as a starting material.

Synthesis Route 2

Synthesis of 2-Amino pyrimidine isoquinolin-4-ones

References: Snyder and Robison, *J. Amer. Chem. Soc.*, 74; 4910-4914 (1952); Di Braccio, M., et al., *Eur. J. Med. Chem.*; 30(1), 27-38 (1995).

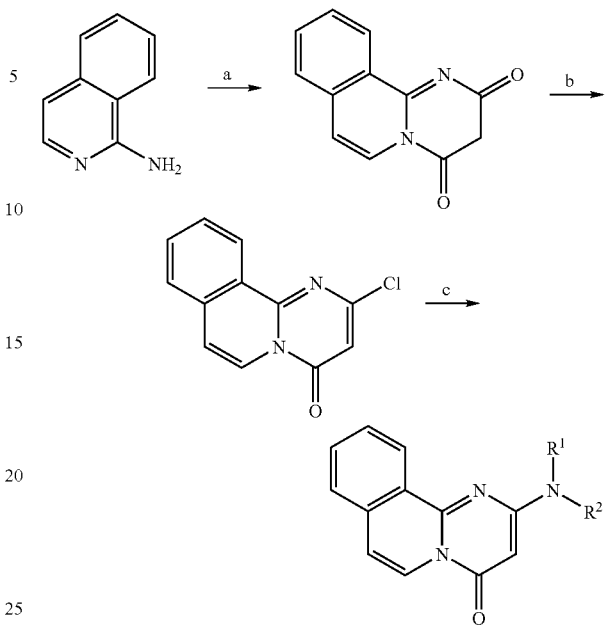

a Diethyl Malonate;
b $POCl_3$;
c $HNR^1R^2$, EtOH (a) Pyrimido[1,2-a]isoquinoline-2,4-dione Aminoisoquinoline (5.16 g, 35.79 mmol) was dissolved in diethyl malonate (5.43 ml, 35.79 mmol). Ethanol (20 ml) was added, and the solution was heated to 170° C. for 4 h. The ethanol was removed by distillation and upon cooling, the dark residue in the reaction flask was triturated in ethyl acetate (10 ml). This resulted in formation of a pale solid which was collected by filtration and washed with ethyl acetate to furnish the title compound as a pale brown solid. (4.43 g, 24.89 mmol, 70% yield). mp=294-296° C. Analytically pure by LC-MS: m/z ($ES^+$): 213 ($M^+$)

(b) 2-Chloro-pyrimido[1,2-a]isoquinolin-4-one

Pyrimido[1,2-a]isoquinoline-2,4-dione (4.43 g, 24.89 mmol) was dissolved in phosphorous oxychloride (20 ml) and this solution was heated to reflux for 5 h. Upon cooling, the reaction mixture was poured carefully into ice water (~250 ml) and adjusted to pH 7 by addition of sodium carbonate. This resulted in formation of a brown precipitate which was collected by filtration and washed with water to yield a brown solid. The crude product was chromatographed, eluting with DCM to provide the title compound as pale yellow crystals. (5.21 g, 22.70 mmol, 91% yield). mp 197-199° C. Analytically pure by LC-MS: m/z ($ES^+$): 231.5 ($M^+$)

(c) 2-Aminopyrimidine isoquinolin-4-ones

2-Chloro-pyrimido[2,1-a]isoquinolin-4-one was dissolved in boiling ethanol (20 ml), and to this solution was added the appropriate amine (4 mol equiv). The solution was heated to reflux, with vigorous stirring, for 16 h. The reaction mixture was then allowed to cool to room temperature, upon which a solid slowly crystallised. The crystalline solid was collected by filtration and washed with cold ethanol (30 ml). This solid was dried under vacuum to provide the desired compound.

Variations

If different substituents are desired on the central core of two fused rings, these can be introduced by varying the substituents on the 2-amino pyridine ring of the starting material, using protecting groups where appropriate.

Synthesis Route 3

Synthesis of
2-Chloro-6-morpholin-4-yl-pyran-4-ones

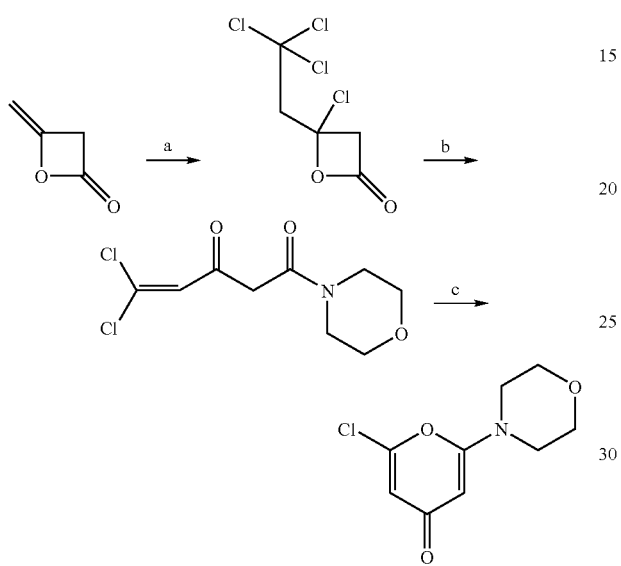

a (bis-4-t-butylcyclohexyl)peroxydicarbonate
b morpholine, NaHCO₃, 15° C.
c perchloric acid, 90° C.

(a) 4-Chloro-4-(2,2,2-trichloro-ethyl)-oxetan-2-one

A solution of (bis-4-t-butylcyclohexyl) peroxydicarbonate (11.8 g) and diketene (83.5 ml) in CCl₄ (300 ml) was added drop wise over 120 min to a refluxing solution of CCl₄, and was stirred for a further 1 h. The resulting pale yellow solution was cooled and azeotroped with dichloromethane. The resulting residue was stirred with hexane (3×150 ml) for 10 min and the liquor was decanted off through a celite pad. The filtered liquors were combined and concentrated in vacuo to give the desired compound as a pale yellow oil (125.0 g, 52.9%).

(b) 5,5-Dichloro-1-morpholin-4-yl-pent-4-ene-1,3-dione

Two separate solutions of 4-Chloro-4-(2,2,2-trichloro-ethyl)-oxetan-2-one (62.5 g, 0.26 mmol) and morpholine (24.0 g, 0.28 mol) in dichloromethane (120 ml) were added simultaneously to a mixture of NaHCO₃ (44.0 g, 0.52 mol) in dry dichloromethane (300 ml). The reaction was maintained at 15° C. over 140 min with stirring. The reaction was filtered, washed with dichloromethane (3×100 ml) and the combined organic layers were concentrated in vacuo to a slurry which was then passed through a short silica pad, and further washed with dichloromethane (4×100 ml). The combined organic layers were concentrated in vacuo, suspended in hexane (400 ml) and stirred for 1 h, filtered and dried to give a cream solid. The solid was suspended in tert-butyl methyl ether (100 ml), stirred for 15 min, filtered, washed with butyl methyl ether and dried to give the desired compound as a white powder (47.8 g, 72%). m/z (LC-MS, ESP): 252 (M$^+$+1).

(c) 2-Chloro-6-morpholin-4-yl-pyran-4-one

To a suspension of 5,5-Dichloro-1-morpholin-4-yl-pent-4-ene-1,3-dione (11.3 g, 44.9 mmol) in dioxane was added perchloric acid (11.4 ml, 0.14 mol) and the reaction was heated at 90° C. under N₂ for 1 h. The reaction was cooled, neutralised with 2M NaOH (75 ml) and filtered. The aqueous layer was extracted with dichloromethane (4×30 ml) and the organic layers were combined and dried over MgSO₄. The organic layer was further treated with charcoal and filtered through celite. The dark yellow filtrate was evaporated in vacuo, and the resulting solid was triturated with hexane (50 ml) and dried to give the desired compound (7.3 g, 75%) as a light yellow powder. m/z (LC-MS, ESP): 216 (M$^+$+1). $^1$HNMR (300 MHz, DMSO-d₆): 3.3 (t, 4H), 3.65 (t, 4H), 5.4 (d, 1H), 6.25 (d, 1H).

Variations:

If the amino group in the final product is desired to be other than morpholino, then the relevant amine, for example dimethylmorpholine can be used in step (b) in place of morpholine.

Synthesis Route 4

Synthesis of 6-Aryl-2-morpholin-4-yl-pyran-4-one
and 6-heterocycle-2-morpholin-4-yl-pyran-4-one

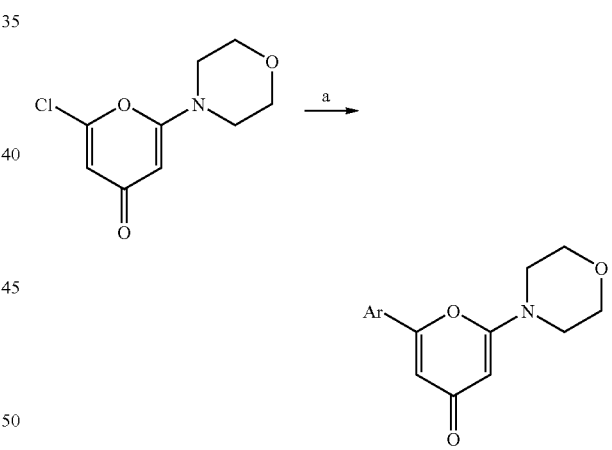

a aryl/heterocycle boronic acid, Cs₂CO₃, Pd(PPh₃)₄, 90° C.

(a) 6-Aryl-2-morpholin-4-yl-pyran-4-ones

A solution of chloropyranone (22 mg, 0.1 mmol) in dioxane (0.3 ml, degassed by sonication and saturation with N₂) was added to aryl boronic acid (0.13 mmol) and Cs₂CO₃ (65 mg, 0.2 mmol) under N₂ atmosphere. Pd(PPh₃)₄ (5 mg, 0.005 mmol) in dioxane (0.2 ml, degassed by sonication and saturation with N₂) was then added to the solution under N₂ atmosphere. The reaction was heated at 90° C. with vigorous stirring overnight. The sample was diluted with methanol/dichloromethane (1:2; 1 ml), passed through a plug of silica (isolute Si 500 mg) and purified by preparative HPLC.

Variations

Where the 6-substituent is desired to be a heterocycle rather than aryl, the appropriate heterocycle boronic acid can be substituted for aryl boronic acid above.

Synthesis Route 4a

Synthesis of N-Alkyl 3-(6-Morpholin-4-yl-4-oxo-4H-pyran-2-yl)-benzamide Derivatives

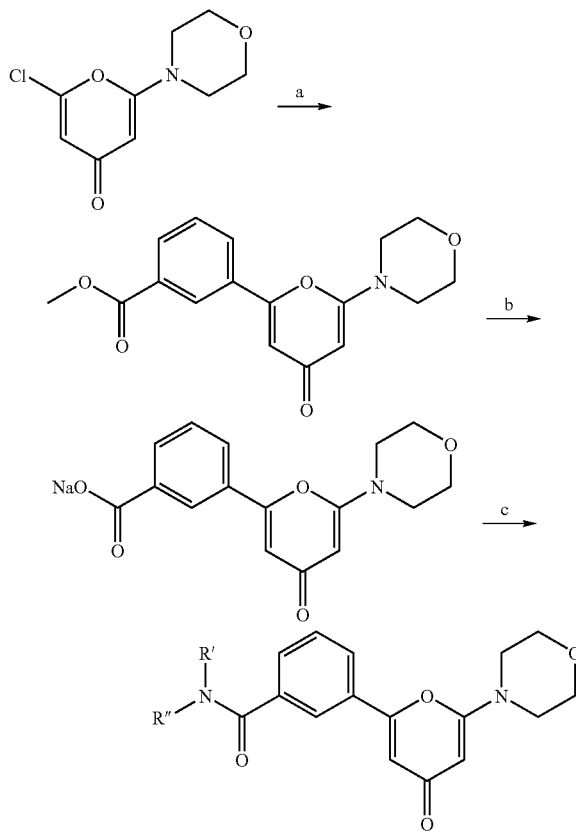

a (3-methoxycabonylphenyl)boronic acid, $K_2CO_3$, Pd(PPh$_3$)$_4$, 90° C.
b NaOH
c N,N dimethylaminopyridine, ethylchloroformate (a) 3-(6-Morpholin-4-yl-4-oxo-4H-pyran-2-yl)-benzoic acid methyl ester 2-Chloro-6-morpholin-4-yl-pyran-4-one (7.98 g, 37 mmol), (3-methoxycarbonylphenyl) boronic acid (8.01 g, 44.5 mmol), and ground potassium carbonate (11.23 g, 81.40 mmol) were suspended in dioxane (50 ml) and degassed (sonication for 5 min then saturated with $N_2$). Pd(PPh$_3$)$_4$ (2.13 g, 1.85 mmol) was then added and the reaction mixture was then heated at 90° C. for 24 hrs under a vigorous stirring and a $N_2$ atmosphere. The solvent were removed in vacuo and the residue was then suspended in water 50 ml) and extracted with ethyl acetate (100 ml). The organics were combined, washed with saturated brine and dried over sodium sulphate. The solvent was removed in vaccuo and the residue was purified by column chromatography (silica; dichloromethane:methanol; 9:1) to give the title compound as a white solid (5.42 g, 46%). m/z (LC-MS, ESP): 316 (M$^+$+1).

(b) 3-(6-Morpholin-4-yl-4-oxo-4H-pyran-2-yl)-benzoic acid sodium salt 3-(6-Morpholin-4-yl-4-oxo-4H-pyran-2-yl)-benzoic acid methyl ester (5.42 g, 17.20 mmol) was dissolved in methanol (25 ml) and sodium hydroxide (0.75 g, 18.90 mmol) was added. The stirred solution was then refluxed under nitrogen for three hours. The methanol was removed in vacuo and the residue was triturated in ether to give the title compound as a brown solid (4.30 g, 83.33%). m/z (LC-MS, ESP): 301 (M$^+$+1).

(c) N-Alkyl 3-(6-Morpholin-4-yl-4-oxo-4H-pyran-2-yl)-benzamide Derivatives

To a stirred solution of 3-(6-Morpholin-4-yl-4-oxo-4H-pyran-2-yl)-benzoic acid sodium salt (52 mg, 0.16 mmol) in anhydrous dimethylacetamide (1 ml), N,N-dimethylaminopyridine (2 mg, catalytic) and ethylchloroformate (19 µl, 0.192 mmol) were added, the solution was stirred for 45 minutes. The desired amine (0.32 mmol) was then added to the reaction mixture was left under stirring overnight. The compound was then purified by preparative HPLC to give the desired compound.

Variations

Where an aryl other than phenyl, or a heterocycle, is desired at the 3-position, the appropriate (methoxycarbonylaryl/heterocycle) boronic acid is substituted for (3-methoxycarbonylphenyl) boronic acid in step (a).

Synthesis Route 4b

Synthesis of N-Alkyl 4-(6-Morpholin-4-yl-4-oxo-4H-pyran-2-yl)-benzamide Derivatives

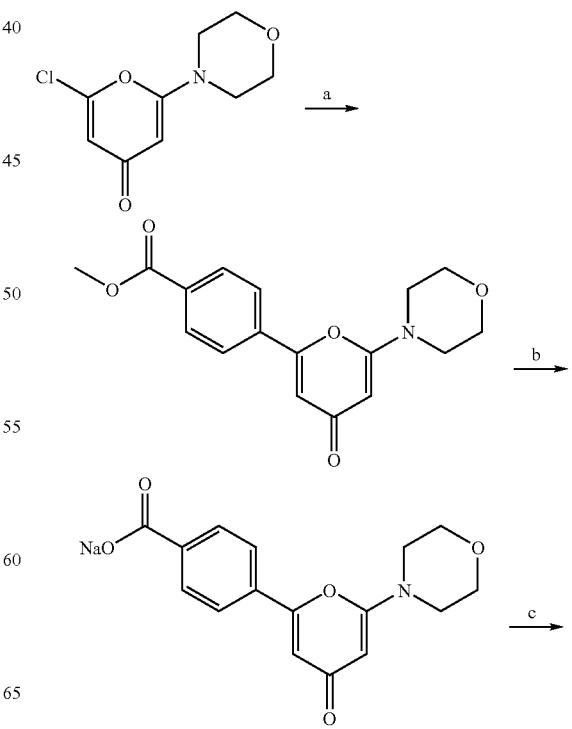

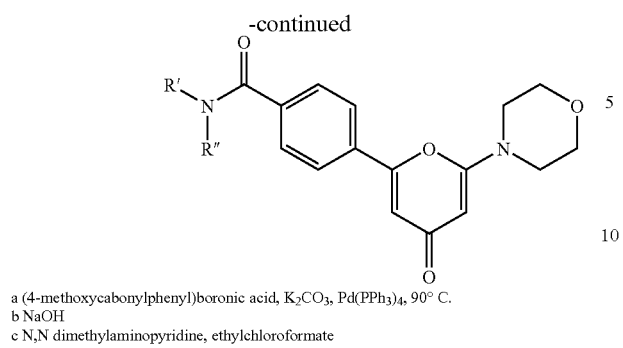

a (4-methoxycabonylphenyl)boronic acid, $K_2CO_3$, $Pd(PPh_3)_4$, 90° C.
b NaOH
c N,N dimethylaminopyridine, ethylchloroformate

(a) 4-(6-Morpholin-4-yl-4-oxo-4H-pyran-2-yl)-benzoic acid methyl ester

2-Chloro-6-morpholin-4-yl-pyran-4-one (4.01 g, 18.60 mmol), (4-methoxycarbonylphenyl)boronic acid (4.01 g, 22.32 mmol), and ground potassium carbonate (5.64 g, 40.92 mmol) were suspended in dioxane (20 ml) and degassed (sonication for 5 min then saturated with $N_2$). $Pd(PPh_3)_4$ (0.5 g, 0.4 mmol) was then added and the reaction mixture was then heated at 90° C. for 24 hrs under a vigorous stirring and a $N_2$ atmosphere. The solvent were removed in vacuo and the residue was then suspended in water 50 ml) and extracted with ethyl acetate (100 ml). The organics were combined, washed with saturated brine and dried over sodium sulphate. The solvent was removed in vacuo and the residue was purified by column chromatography (silica; dichloromethane:methanol; 9:1) to give the title compound as a white solid 3.71 g, 63%). m/z (LC-MS, ESP): 316 ($M^+$+1).

(b) 4-(6-Morpholin-4-yl-4-oxo-4H-pyran-2-yl)-benzoic acid sodium salt 4-(6-Morpholin-4-yl-4-oxo-4H-pyran-2-yl)-benzoic acid methyl ester (3.00 g, 9.52 mmol) was dissolved in methanol (20 ml) and sodium hydroxide (0.381 g, 9.52 mmol) was added. The stirred solution was then refluxed under nitrogen for three hours. The methanol was removed in vacuo and the residue was triturated in ether to give the title compound as a brown solid (3 g, 97%). m/z (LC-MS, ESP): 301 ($M^+$+1).

(c) N-Alkyl 4-(6-Morpholin-4-yl-4-oxo-4H-pyran-2-yl)-benzamide Derivatives

To a stirred solution of 4-(6-Morpholin-4-yl-4-oxo-4H-pyran-2-yl)-benzoic acid sodium salt (52 mg, 0.16 mmol) in anhydrous dimethylacetamide (1 ml), N,N-dimethylaminopyridine (2 mg, catalytic) and ethylchloroformate (19 μl, 0.192 mmol) were added, the solution was stirred for 45 minutes. The desired amine (0.32 mmol) was then added to the reaction mixture was left under stirring overnight. The compound was then purified by preparative HPLC to give the desired compound.

Variations

Where an aryl other than phenyl, or a heterocycle, is desired at the 4-position, the appropriate (methoxycarbonylaryl/heterocycle) boronic acid is substituted for (4-methoxycarbonylphenyl) boronic acid in step (a).

Synthesis route 4c(i)

Synthesis of (3-aminomethyl-phenyl)-6-morpholin-4-yl-pyran-4-one Derivatives

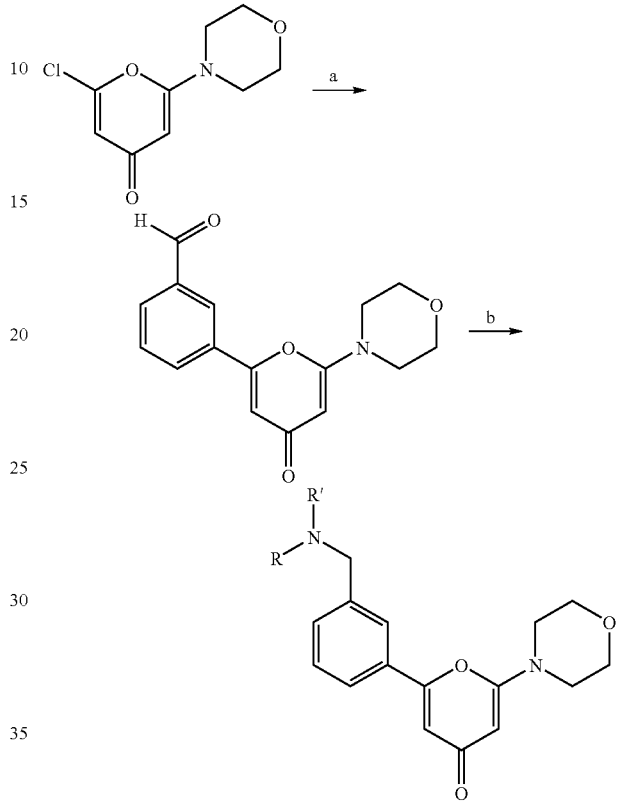

a 3-formylphenylboronic acid, $K_2CO_3$, $Pd(PPh_3)_4$, 80° C.
b amine, sodium triacetoxyborohydride, glacial acetic acid

(a) [3-(6-Morpholine-4-yl-4-oxo-4H-pyran-2yl)-phenyl]benzaldehyde

Chloropyranone (10.75 g, 50 mmol) and 3-formylphenylboronic acid (9.0 g, 60 mmol) were stirred in a solution of degassed dioxane (110 ml) for 20 min. This was followed by the addition of Na2CO3 (13.8 g, 100 mmol) and tetrakis (triphenylphosphine) palladium (2.88 g, 2.5 mmol). The reaction mixture was further degassed for 10 min and heated to 80° C. under $N_2$ for 18 h. The reaction was then cooled to room temperature, concentrated in vacuo and purified by flash column chromatography (ethyl acetate/methanol) to yield 3-(6-morpholin-4-yl-4-oxo-4H-pyran-2-yl)benzaldehyde as a orange solid (6.5 g, 45%). m/z (LC-MS, ESP): 286 ($M^+$+1).

(b) (3-aminomethyl-phenyl)-6-morpholin-4-yl-pyran-4-ones Derivatives 3-(6-morpholin-4-yl-4-oxo-4H-pyran-2-yl)benzaldehyde (0.2 mmol) and the appropriate amine (0.24 mmol) were dissolved in dichloroethane (2 ml). Sodium triacetoxyborohydride (0.28 mmol) and glacial acetic acid (6.0 mmol) were then added and stirred at room temperature for 16 h. The reaction mixtures were then purified by preparatory HPLC.

Synthesis route 4c(ii)

Synthesis of (4-aminomethyl-phenyl)-6-morpholin-4-yl-pyran-4-one Derivatives

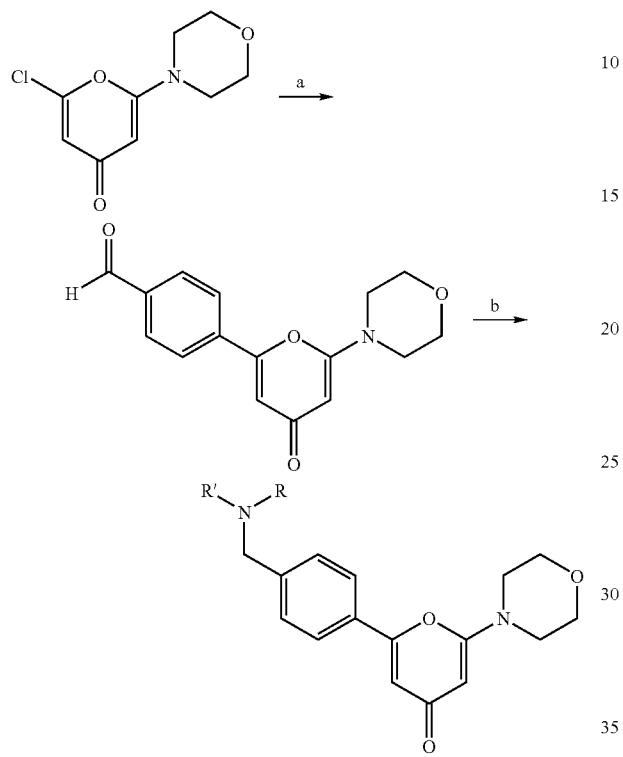

a 4-formylphenylboronic acid, $K_2CO_3$, $Pd(PPh_3)_4$, 80° C.
b amine, sodium triacetoxyborohydride, glacial acetic acid

(a) [4-(6-Morpholine-4-yl-4-oxo-4H-pyran-2yl)-phenyl]benzaldehyde

Chloropyranone (10.75 g, 50 mmol) and 4-formylphenylboronic acid (9.0 g, 60 mmol) were stirred in a solution of degassed dioxane (110 ml) for 20 min. This was followed by the addition of $Na_2CO_3$ (13.8 g, 100 mmol) and tetrakis(triphenylphosphine) palladium (2.88 g, 2.5 mmol). The reaction mixture was further degassed for 10 min and heated to 80° C. under $N_2$ for 18 h. The reaction was then cooled to room temperature, concentrated in vacuo and purified by flash column chromatography (ethyl acetate/methanol) to yield 4-(6-morpholin-4-yl-4-oxo-4H-pyran-2-yl)benzaldehyde as a yellow powder (6 g, 42%). m/z (LC-MS, ESP): 286 ($M^+$+1).

(b) (4-aminomethyl-phenyl)-6-morpholin-4-yl-pyran-4-ones Derivatives 4-(6-morpholin-4-yl-4-oxo-4H-pyran-2-yl)benzaldehyde (0.2 mmol) and the appropriate amine (0.24 mmol) were dissolved in dichloroethane (2 ml). Sodium triacetoxyborohydride (0.28 mmol) and glacial acetic acid (6.0 mmol) were then added and stirred at room temperature for 16 h. The reaction mixtures were then purified by preparatory HPLC.

Synthesis route 4d (i)

Synthesis of (3-amino-phenyl)-6-morpholin-4-yl-pyran-4-ones

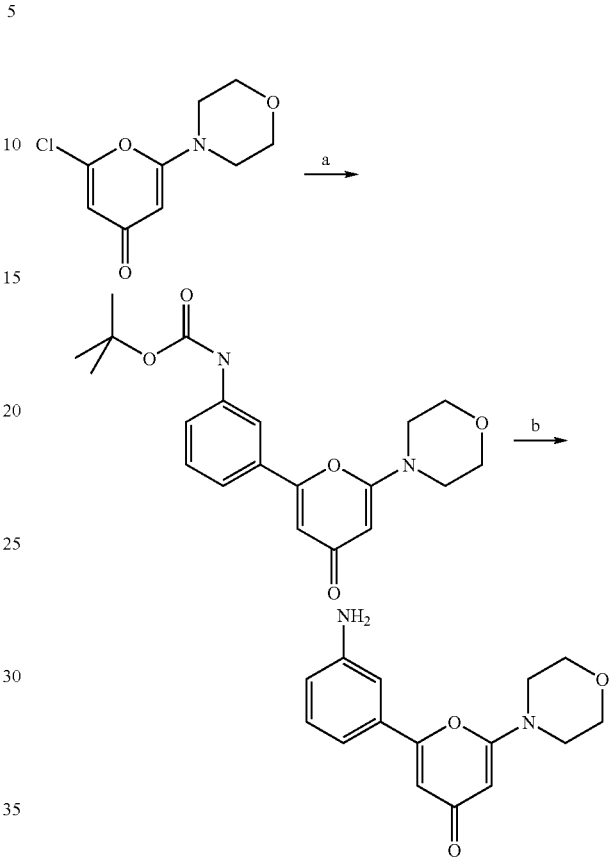

a 3-(BOC-aminophenyl)boronic acid, $Na_2CO_3$, $Pd(PPh_3)_4$
b TFA

(a) Synthesis of [3-(6-Morpholine-4-yl-4-oxo-4H-pyran-2-yl)-phenyl]carbamic acid tert-butyl ester Chloropyranone (1.8 g, 8.35 mmol) and 3-(BOC-aminophenyl)boronic acid (2.4 g, 10 mmol) were stirred in a solution of degassed dioxane (45 ml) for 20 min. This was followed by the addition of $Na_2CO_3$ (2.78 g, 20.16 mmol) and tetrakis(triphenylphosphine) palladium (483 mg, 0.08 mmol). The reaction mixture was further degassed for 10 min and heated to 80° C. under $N_2$ for 18 h. The reaction was then cooled to room temperature, concentrated in vacuo and purified by flash column chromatography (ethyl acetate/methanol) to yield to the title compound (1.51 g, 48%). m/z (LC-MS, ESP): 373 ($M^+$+1).

(b) Synthesis of (3-amino-phenyl)-6-morpholin-4-yl-pyran-4-one

[3-(6-Morpholine-4-yl-4-oxo-4H-pyran-2yl)-phenyl]carbamic acid tert-butyl ester (3.4 g, 9.2 mmol) was dissolved in 25% trifluoroacetic acid in dichloromethane mixture (30 ml) and stirred for 1 hour at room temperature. The reaction was concentrated in vacuo, precipitated with saturated $NaHCO_3$, filtered, washed with diethyl ether and dried to yield (3-amino-phenyl)-6-morpholin-4-yl-pyran-4-one as a white solid (2.1 g, 85%). m/z (LC-MS, ESP): 273 ($M^+$+1).

Synthesis route 4d (ii)

Synthesis of (4-aminophenyl)-6-morpholin-4-yl-pyran-4-ones

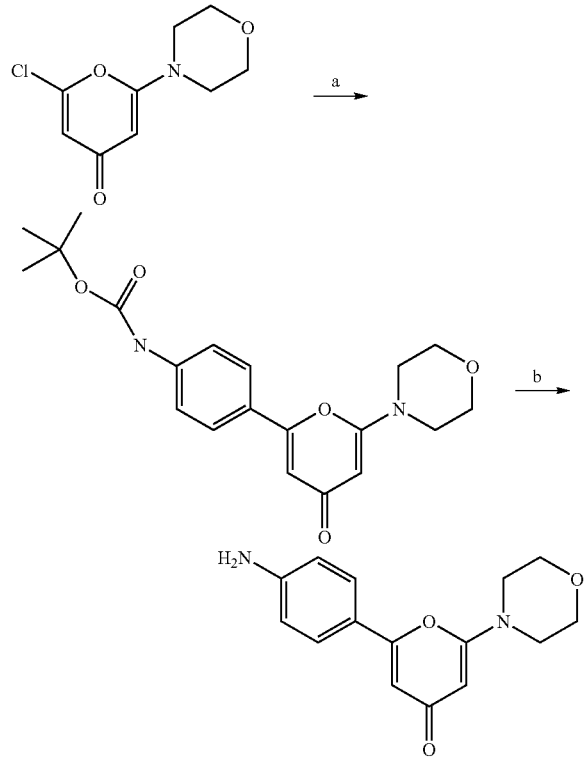

a 4-(BOC-aminophenyl)boronic acid, NaCO₃, Pd(PPh₃)₄
b TFA

(a) Synthesis of [4-(6-Morpholine-4-yl-4-oxo-4H-pyran-2yl)-phenyl]carbamic acid tert-butyl ester Chloropyranone (1 g, 4.64 mmol) and 4-(BOC-aminophenyl)boronic acid (1.14 g, 5.57 mmol) were stirred in a solution of degassed dioxane (10 ml) for 20 min. This was followed by the addition of Na₂CO₃ (1.41 g, 10.21 mmol) and tetrakis(triphenylphosphine) palladium (268 mg, 0.05 mmol). The reaction mixture was further degassed for 10 min and heated to 80° C. under N₂ for 18 h. The reaction was then cooled to room temperature, concentrated in vacuo and purified by flash column chromatography (ethyl acetate/methanol) to yield to the title compound (0.9 g, 52%). m/z (LC-MS, ESP): 373 (M⁺+1).

(b) Synthesis of (4-amino-phenyl)-6-morpholin-4-yl-pyran-4-one

[4-(6-Morpholine-4-yl-4-oxo-4H-pyran-2yl)-phenyl]carbamic acid tert-butyl ester (402 mg, 1.08 mmol) was dissolved in 25% trifluoroacetic acid in dichloromethane mixture (5 ml) and stirred for 1 hour at room temperature. The reaction was concentrated in vacuo, precipitated with saturated NaHCO₃, filtered, washed with diethyl ether and dried to yield (4-amino-phenyl)-6-morpholin-4-yl-pyran-4-one as a yellow solid (230 mg, 79%). m/z (LC-MS, ESP): 273 (M⁺+1).

Synthesis route 4d(iii)

(4-acylamido-phenyl)-6-Morpholin-4-yl-pyran-4-ones Derivatives

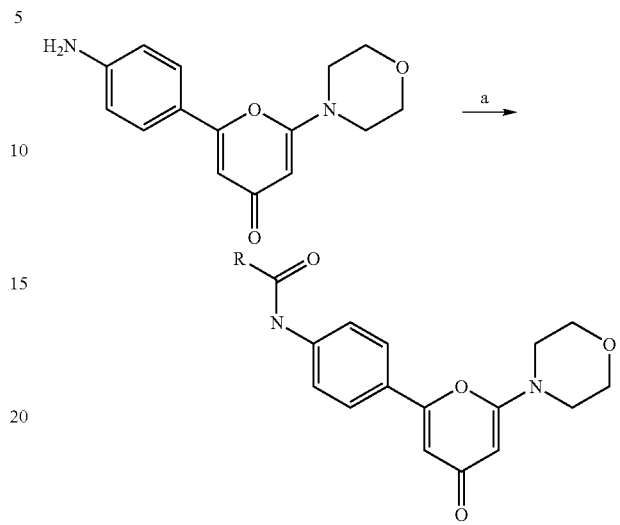

a acid chloride/isocyanate/isothiocyanate, Hünig's base (a) Appropriate acid chloride (0.24 mmol) was added to a solution of (4-Amino-phenyl)-6-morpholin-4-yl-pyran-4-one (0.2 mmol) in dichloromethane (2 ml). Hünig's base (0.4 mmol) was then added and the reaction was stirred at room temperature for 16 h. The reaction mixtures were then purified by preparatory HPLC.

Variations

Isocyanate or isothiocyanate can be used in place of acid chloride to generate ureido or thioureido structures.

Synthesis route 4d(iv)

(3-acylamido-phenyl)-6-Morpholin-4-yl-pyran-4-ones Derivatives

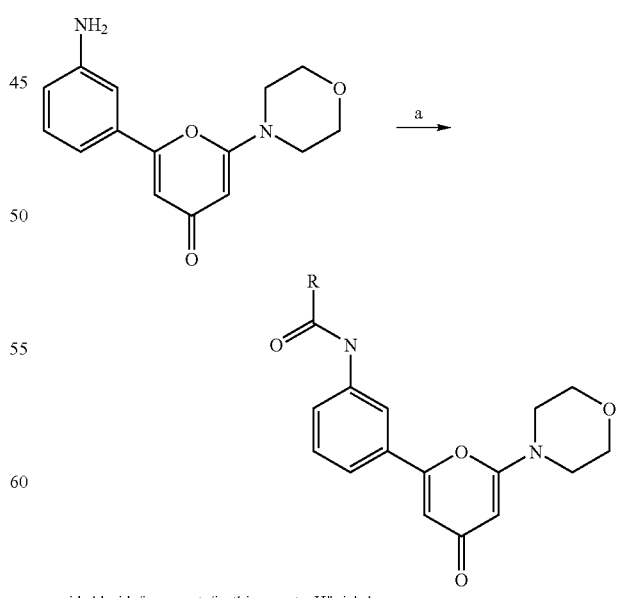

a acid chloride/isocyanate/isothiocyanate, Hünig's base (a) Appropriate acid chloride (0.24 mmol) was added to a solution of (3-Amino-phenyl)-6-morpholin-4-yl-pyran-4-one (0.2 mmol) in dichloromethane (2 ml). Hünig's base (0.4 mmol) was then added and the reaction was stirred at room temperature for 16 h. The reaction mixtures were then purified by preparatory HPLC.

Variations

Isocyanate or isothiocyanate can be used in place of acid chloride to generate ureido or thioureido structures.

Synthesis route 4d(v)

Synthesis of (3-amino-phenyl)-6-morpholin-4-yl-pyran-4-one Derivatives

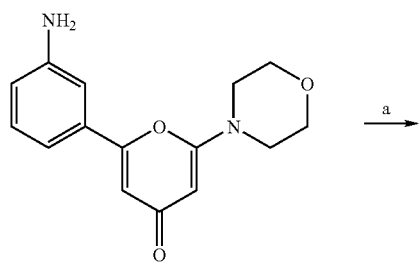

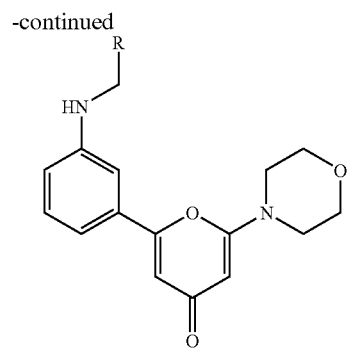

a aldehyde, sodium triacetoxyborohydride, glacial acetic acid (a) (3-Amino-phenyl)-6-morpholin-4-yl-pyran-4-one (0.2 mmol) and the appropriate aldehydes (0.24 mmol) were dissolved in dichloroethane (2 ml). Sodium triacetoxyborohydride (0.28 mmol) and glacial acetic acid (6.0 mmol) was then added and stirred at room temperature for 16 h. The reaction mixtures were then purified by preparatory HPLC.

Synthesis Route 5

Synthesis of 2-(4-Morpholinyl)-6-aryl-4H-pyran-4-ones

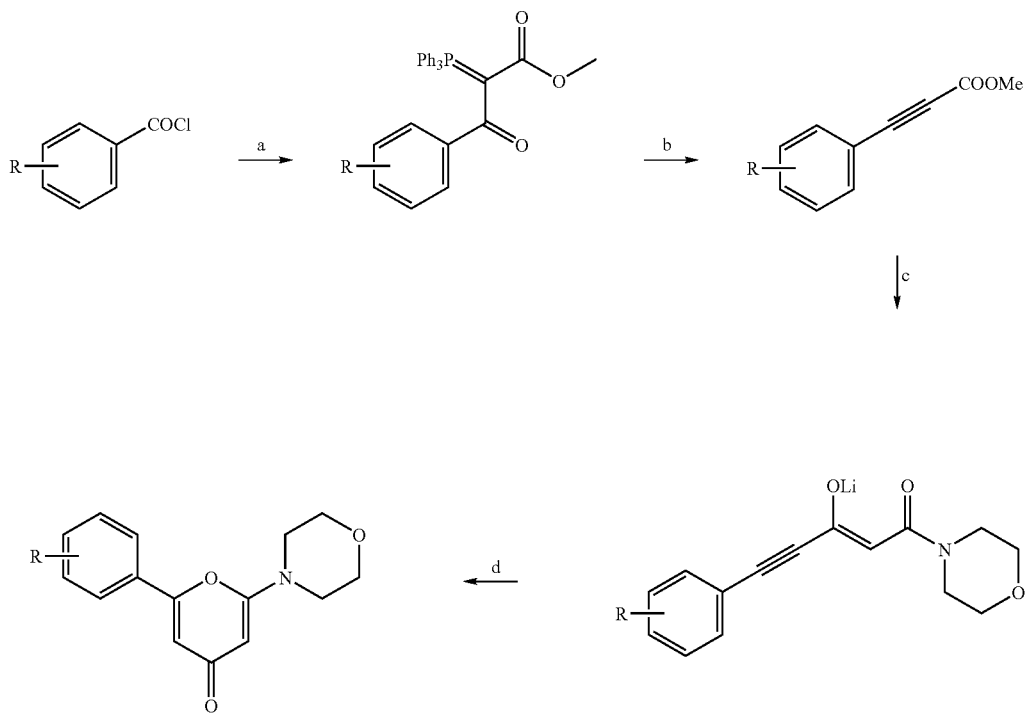

a Ph$_3$P=CHCO$_2$Me
b 250° C.
c acetyl morpholine, LDA
d MeSO$_3$H

(a) 3-(Aryl)-3-oxo-2-triphenylphosphoranylpropionates

A mixture of methyl triphenylphosphoranylideneacetate (20 mmol) and appropriate aroyl chloride (10 mmol) in anhydrous toluene (100 ml) under nitrogen was refluxed for 3 h, cooled to room temperature and the white precipitate formed was filtered. The filter cake was thoroughly washed with ethyl acetate (4×40 ml) and the combined filtrate evaporated in vacuo. The oil was purified by column chromatography to give the desired compound.

(b) Methyl 3-(aryl)propiolates

Methyl 3-(3-aryl)-3-oxo-2-triphenylphosphoranylpropanoate (9 mmol) was slowly warmed to 250° C. in a kugelrohr distillation apparatus (1 Torr). Distillate was collected for 20 minutes at 250° C. and was purified by column chromatography to give the desired product.

(c) 4-[(2-Oxo-4-aryl-3-butynyl)carbonyl]morpholine lithium salts n-Butyllithium (2.5 M in hexanes, 5.3 ml, 13.2 mmol) was added dropwise at 0° C. to a stirred solution of diisopropylamine (1.87 ml, 13.2 mmol) in THF (20 ml) under a nitrogen atmosphere. After 30 minutes, acetyl morpholine (1.53 ml, 13.2 mmol) was added dropewise to the reaction mixture and left for one h under stirring at 0° C. The reaction was then cooled to −78° C. and methyl 3-(3-aryl)propiolate (6 mmol) in THF (5 ml) was added dropwise to the reaction mixture and left to react at −78° C. for 30 minutes and then to 0° C. for 1 h. The reaction mixture was quenched with water (15 ml) and the white suspension extracted twice with dichloromethane (30 ml). The organics were combined and evaporated under reduce pressure to give a solid which was triturated with acetone (10 ml). The solid was filtered and washed successively with water (5 ml), acetone (5 ml) and ether (5 ml). The solid obtained was then dried in vacuo overnight at 40° C. to give the desired compound.

(d) 2-(4-Morpholinyl)-6-aryl-4H-pyran-4-one

A solution of 4-[(2-oxo-4-aryl-3-butynyl)carbonyl]morpholine lithium salt (2 mmol) in methanesulphonic acid (6 ml) was stirred under nitrogen for 3 h at room temperature. The mixture was poured into saturated sodium carbonate solution (100 ml) and extracted with dichloromethane (3×50 ml). The combined organics were dried over sodium sulphate and evaporated in vacuo. The residue was purified by column chromatography Variations If the amino group in the final product is desired to be other than morpholino, than the relevant acetyl amine can be used in step (c) in place of acetyl morpholine.

Synthesis Route 6

Synthesis of 2-amino-chromen-4-ones (1$^{st}$ Method)

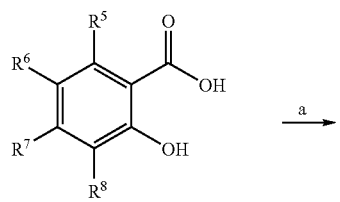

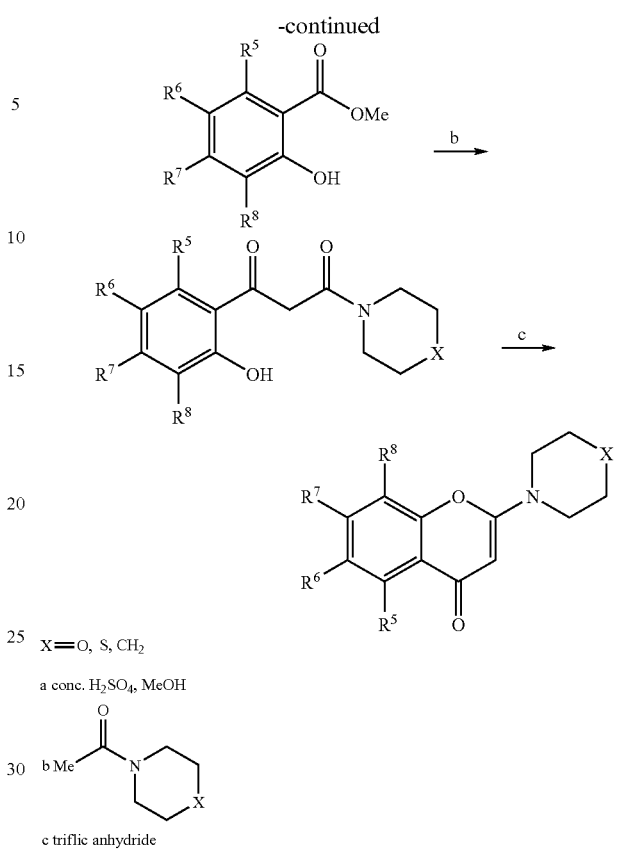

X=O, S, CH$_2$ a conc. H$_2$SO$_4$, MeOH b Me-C(O)-N(piperazine)-X c triflic anhydride

(a) Salicylate Esters

A solution of the appropriate acid in methanol (150 ml) was treated with concentrated sulphuric acid (3 ml). The solution was heated to reflux for 40 h and then cooled to room temperature. The reaction mixture was evaporated in vacuo and then re-suspended in ethyl acetate (200 ml). The solution was washed with 50% saturated sodium bicarbonate solution (4×150 ml). The aqueous extracts were combined and washed with ethyl acetate (150 ml). The organic extracts were combined, washed with brine (50 ml), dried over sodium sulphate and evaporated in vacuo to give the product, which was then crystallised from methanol to provide the desired compound.

(b) β-ketoamides

A solution of diisopropylamine (5.1 ml, 3.0 mmol) in THF (30 ml) was cooled to −70° C. and slowly treated with 2.5 M solution of n-butyl lithium in hexanes (14.0 ml, 35 mmol) and then warmed to 0° C. and stirred for 15 minutes. The solution was cooled to −10° C. and slowly treated with a solution of N-acetyl morpholine, N-acetyl piperidine, or N-acetyl thiomorpholine in THF (25 ml), maintaining the temperature below −10° C. The reaction mixture was stirred at this temperature for 90 minutes and then treated with a solution of the relevant salicylate ester in THF (25 ml), followed by additional THF (5 ml). The reaction mixture was slowly warmed to room temperature and stirred for 16 h. The solution was quenched with water (5 ml) and 2 M hydrochloric acid (50 ml) and extracted into DCM (3×80 ml). The organic extracts were combined, washed with brine (50 ml), dried over sodium sulphate and evaporated in vacuo to give an oily residue. The crude product was stirred vigorously in hot ether, causing precipitation of a white solid. This was collected, after cooling in ice, by filtration and washed with cold ether, to provide the desired compound.

(c) 2-amino-chromen-4-ones

A solution of the appropriate β-ketoamides in DCM (35 ml) was treated with triflic anhydride (3.8 ml, 23 mmol) and stirred at room temperature under nitrogen for 16 h. The mixture was evaporated in vacuo and then re-dissolved in methanol (80 ml). The solution was stirred for 4 h, treated with water (80 ml) and stirred for a further hour. The mixture was evaporated in vacuo to remove methanol. The aqueous mixture was adjusted to pH 8 by treatment with saturated sodium bicarbonate and then extracted into DCM (3×150 ml). The extracts were dried over sodium sulphate and evaporated in vacuo to give a solid. The crude product was partially dissolved in DCM and loaded onto a silica column, eluting with DCM followed by (1%; 2%; 5%) methanol in DCM. All fractions containing the desired product were combined and evaporated in vacuo to give an orange solid. The crude product was dissolved in hot methanol, treated with charcoal, filtered through celite and recrystallised from methanol to provide the desired compound.

Variations

If the amino group in the final product is desired to be other than morpholino, than the relevant acetyl amine can be used in step (b) in place of acetyl morpholine.

Synthesis Route 7a

Synthesis of 2-amino-chromen-4-ones ($2^{nd}$ Method)

Di Braccio, M., et al., *Farmaco*, 50(10), 703-711 (1995); Vlahos, C. J., et al., *J. Biol. Chem.*, 269(7), 5241-5248 (1994).

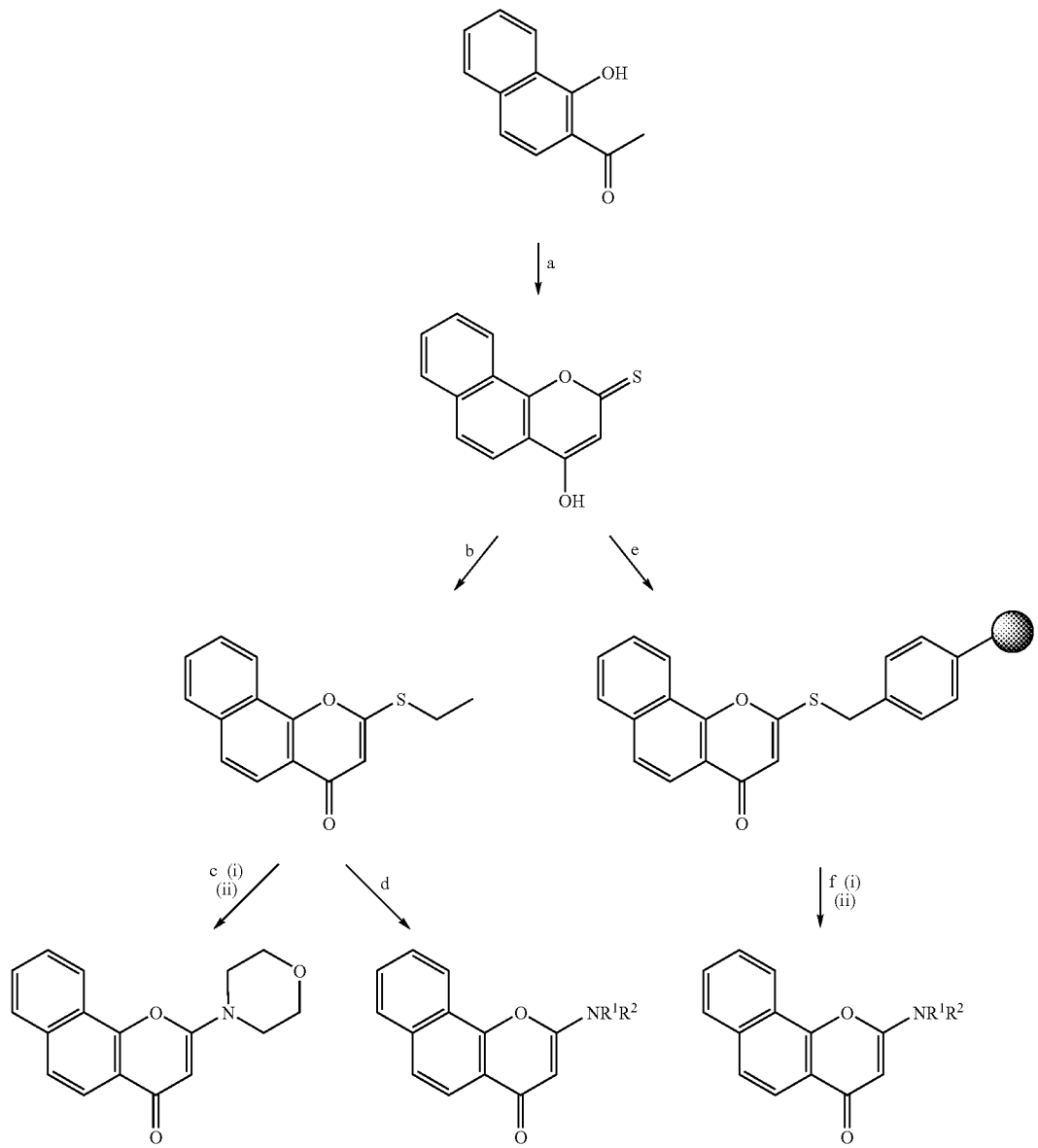

a CS$_2$, Potassium t-Butoxide;
b EtI, K$_2$CO$_3$, Acetone;
c (i) mCPBA, DCM; (ii) HNR$^1$R$^2$, MeCN;
d HNR$^1$R$^2$, Ethylene Glycol, 160° C.;

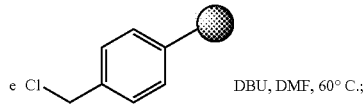

e Cl— ... DBU, DMF, 60° C.;

f (i) mCPBA, DCM; (ii) HNR$^1$R$^2$, MeCN;
Route illustrated for benzo-[h]-chromen-4-ones

(a) 4-hydroxy-chromen-2-thiones

A suspension of potassium tert-butoxide (7.20 g, 64 mmol) in toluene (50 ml) was cooled to ~10° C. and treated with a solution of the appropriate acetoaryl and carbon disulphide (1.20 ml, 20.0 mmol) in toluene (50 ml). The resultant mixture was stirred at room temperature for 16 h and then treated with water (500 ml). The mixture washed with ether (2×100 ml) and charged into a 3-neck round bottom flask. The aqueous solution was treated with 10% sulphuric acid, venting the flask through a bleach trap. The resultant suspension was stirred for 24 h to allow for removal of hydrogen sulphide. The solid was collected by filtration, washing with water (3×50 ml) and cold petrol (3×50 ml). Recrystallisation from ethyl acetate/petrol provided the desired compound.

(b) 2-(Ethylthio)-chromen-4-ones

A solution of 4-hydroxy-chromen-2-thione in acetone (10 ml) is treated with potassium carbonate and ethyl iodide and heated to reflux. The reaction mixture was evaporated in vacuo, re-dissolved in DCM (20 ml) and washed with water (20 ml). The aqueous layer washed with additional DCM (3×20 ml) and the organic extracts were combined, dried over sodium sulphate and evaporated in vacuo. The residue was recrystallised from ethyl acetate/petrol to provide the desired compound.

(c) 2-amino-benzo-chromen-4-ones

A solution of the appropriate 2-(ethylthio)-benzo-chromen-4-one in DCM (10 ml) at 0° C. is treated with a solution of mCPBA in DCM (10 ml) and stirred at room temperature. The reaction mixture is cooled to −20° C. to form a precipitate which is removed and washed. This is suspended in acetonitrile, and treated with the appropriate secondary amine and stirred at room temperature. The reaction mixture is evaporated in vacuo and re-dissolved in ethyl acetate (100 ml). This solution is then washed with 50% saturated sodium bicarbonate solution (2×100 ml), dried over sodium sulphate and evaporated in vacuo. The solid residue is triturated in ether, filtered and the solid collected recrystallised from methanol to provide the desired compound.

(d) 2-amino benzenechromen-4-ones

A mixture of 2-ethylsulphanyl-benzochromen-4-one, the appropriate amine (10 mol equiv) and ethylene glycol (10 ml) was heated to 160° C., with stirring, for 3 h. Upon cooling to room temperature the reaction mixture was poured onto ice water (100 ml) and extracted into DCM. The organic extracts were collected, dried over sodium sulphate, and the solvent was removed by evaporation in vacuo to yield the product as a pale solid. The product was purified by recrystallisation from a suitable solvent.

(e) (Benzo-4-oxo-4H-chromen-2-yl)-thiomethylpolystyrene-divinylbenzene Resin Merrifield resin (1% cross-linked, 1.2 mmol/g) (0.70 g, 0.84 mmol) was swelled in anhydrous DMF (4 ml). The mixture was shaken gently for 15 minutes and then treated with a solution of the appropriate 4-Hydroxy-benzo-chromen-2-thione (0.50 g, 2.2 mmol) in DMF (3 ml). After shaking for a further 15 minutes, the mixture is treated with 1,8-diazabicyclo[5.4.0]undec-7-ene (0.4 ml, 2.7 mmol). The reaction mixture is then heated to 70° C. and gently shaken for 24 h. The resin is collected by filtration and washed with DMF, followed by methanol and finally washed with DCM.

(f) Benzo-chromen-4-ones Library

The appropriate (Benzo-4-oxo-4H-chromen-2-yl)-thiomethylpolystyrene-divinylbenzene resin (0.030 g, 0.036 mmol) is swelled in anhydrous DMF and gently shaken for 15 minutes. The reaction mixture was treated with a prepared solution of amine (0.036 mmol) in DCM (0.2 ml). The mixture is shaken at room temperature for 24 h, followed by addition of Amberlite IR120+ resin (50 mg) and shaking for a further 1 h. The reaction mixture is then filtered, washing the resin with DCM and methanol. The filtrate was evaporated in vacuo to provide 0.0014 g (0.004 mmol) of the crude desired compound, which is submitted for analysis by LC-MS without further purification.

Variations

If different substituents are desired on the central core of two fused rings, these can be introduced by varying the substituents on the ring of the salicylic acid starting material, using protecting groups where appropriate (e.g. see route 7b).

Substituted Morpholines

Substituted morpholines such as 2-Ethyl-morpholine and 2,2-Dimethyl-morpholine were prepared using methodology described in Bettoni et al. Tetrahedron, 1980, 36, 409-415, as discussed in relation to Compound 317 below.

Synthesis Route 7b

Solid Phase Synthesis of 7-alkoxy-2-(morpholin-4-yl)-chromen-4-ones

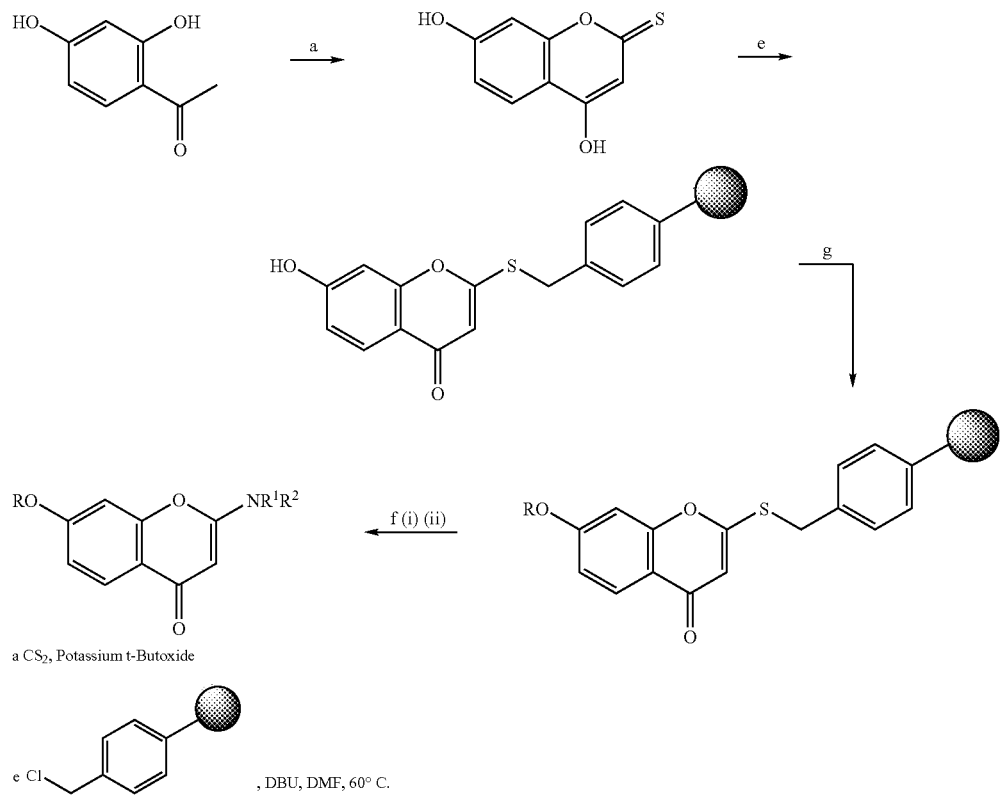

a CS$_2$, Potassium t-Butoxide e Cl—[benzyl-resin], DBU, DMF, 60° C.

g Alkylating agent
f (i) mCPBA, DCM
  (ii) HNR$^1$R$^2$, MeCN

Steps (a), (e) and (f) are as for Synthesis Route 7a.

(g) (7-(Alkoxyoxy)-4-oxo-4H-chromen-2-yl)-thiomethylpolystyrene-divinylbenzene Resins (7-(Hydroxy)-4-oxo-4H-chromen-2-yl)-thiomethylpolystyrene-divinylbenzene resin (0.030 g, <0.036 mmol) was swelled in anhydrous DMF and gently shaken for 15 minutes. The mixture was treated with 1,8-diazabicyclo[5.4.0]undec-7-ene (0.2 ml, 1.3 mmol). After shaking for a further 15 minutes, the mixture was treated with an alkylating agent (e.g. benzyl bromide). The reaction was heated to 65° C. and shaken for 20 h. The resin was collected by filtration and washed in order with DMF, methanol and DCM. This procedure was repeated on the resin with fresh reagents a further 3 times.

Variations

If different substituents are desired on the central core of two fused rings, these can be introduced by varying the substituents on the ring of the acetophenone starting material, for example using 2,5-dihydroxyacetophenone in place of 2,4-dihydroxyacetophenone to generate 6-hydroxy substituted chromen-4-ones.

Synthesis Route 7b(i)

Derivatisation of 7-hydroxy Substituted chromen-4-ones

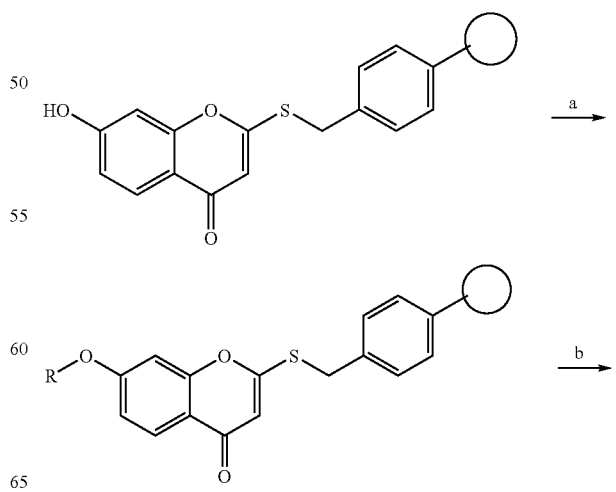

-continued

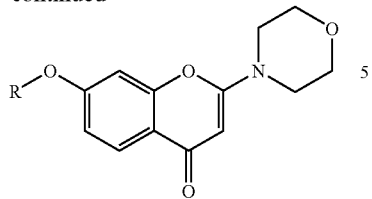

a TEA, PPh₃, ROH, DIAD
b mCPBA, morpholine (a) (7-aryloxy-4-oxo-4H-chromen-7-yl)-thiomethylpolystyrene-divinylbenzene resins S-(7-Hydroxy-4-oxo-4H-chromen-7-yl)-thiomethylpolystyrene-divinylbenzene resin (0.020 g, <0.024 mmol) was swelled in THF (1 ml) in an Advanced Chemtech reaction fritted vessel and gently shaken for 15 min. Gently agitating for 10 min between the addition of each reagent, the vessel was sequentially treated with TEA (0.05 ml), a solution of triphenylphosphine (0.063 g) in THF (0.5 ml) and a solution of the appropriate alcohol (0.25 mmol) in THF (0.5 ml). After a further 10 min the vessel was treated with a solution of DIAD (0.047 ml) in THF (0.5 ml), chilled in a dry ice/acetone bath prior to addition. The reaction vessels were gently agitated for 20 h, drained, and the resin washed with DCM×2, DMF×1, methanol×1 and DCM×2

(b) 7-aryloxy-2-morpholin-4-yl-chromen-4-ones

The resin bound chromone (maximum 0.036 mmol) was suspended in DCM (2 ml) and after shaking for 10 min, the mixture was treated with mCPBA (0.2 g, 1.1 mmol). The mixture was shaken at room temperature for 3 hours and then filtered. The resin washed in order with DCM×2, methanol× 2, DCM×2 and re-suspended in DCM (2 ml). After shaking for 15 minutes the mixture was treated with a solution of morpholine (0.005 ml, 0.05 mmol) in DCM (2 ml). The mixture was shaken at room temperature for 16 h and filtered, washing the resin with methanol (2×2 ml). The filtrate was evaporated in vacuo to provide the title compound. The product was submitted for analysis by LC-MS without further purification.

Variations

If the amino group in the final product is desired to be other than morpholino, than the amine can be used in step (b) in place of morpholine. The 7-substituent may be substituted or unsubstituted alkyl, heterocyclyl, etc rather than aryl by using the appropriate alcohol in step (a).

Synthesis Route 7c

Synthesis of 2-(morpholin-4-yl)-chromen-4-ones Derivatives

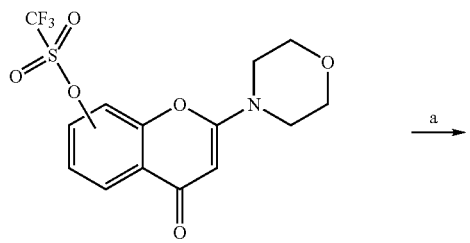

a

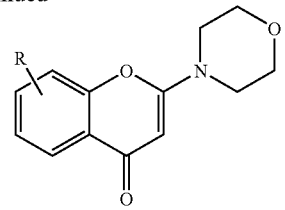

a Organoboron, K₂CO₃, Pd(PPh₃)₄, 90° C.

(a) Aryl substituted 2-(morpholin-4-yl)-chromen-4-ones

Organoboron compound (0.058 mmol), Trifluoro-methanesulfonic acid 2-morpholin-4-yl-4-oxo-4H-chromenyl ester (Compound 305 or 306) (20 mg, 0.053 mmol and powdered potassium carbonate (14.6 mg, 0.106 mmol) were added to a reaction tube, which was then purged with nitrogen and sealed. A flask of dioxane was degassed with nitrogen purge and sonication for 5 min before addition to the reaction tube (0.5 ml). To this was added a solution of tetrakis(triphenylphosphine) palladium(0) (3.1 mg) in degassed dioxane (0.3 mL) and the reaction mixture was heated to 90° C. with reflux under a nitrogen atmosphere for 18 h. The reaction was cooled and passed through a silica plug (isolute Si 500 mg cartridge) and eluted with 30% Methanol/DCM (8 mL). The solution was analysed by LCMS and purified by preparative HPLC.

Synthesis Route 8

Further Derivitisation of 7-(hydroxy)-2-(morpholin-4-yl)-chromen-4-one to 7-alkoxy-2-(morpholin-4-yl)-chromen-4-ones

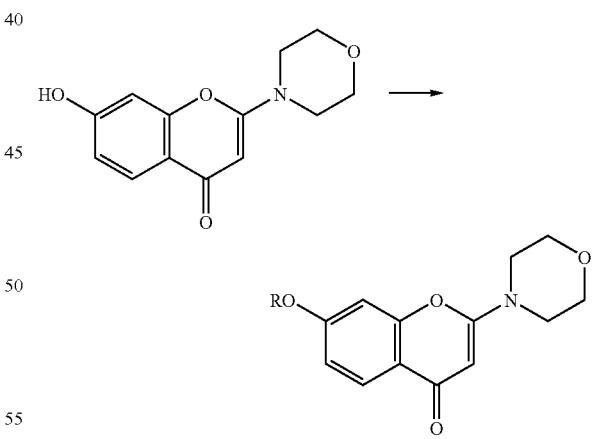

A solution of 7-(hydroxy)-2-(morpholin-4-yl)-chromen-4-one (307) (0.125 g, 0.50 mmol) in anhydrous DMF (5 ml) was treated with the appropriate aryl bromide, followed by a 40% methanolic solution of benzyltrimethylammonium hydroxide (0.54 ml, 1.2 mmol). The solution was heated to 80° C. and stirred for 16 h. After cooling, the solution was treated with ethyl acetate (25 ml) and water (10 ml). The mixture was stirred vigorously for 30 minutes and allowed to settle. The ethyl acetate layer was removed by pipette and evaporated in vacuo. The crude product was recrystallised from methanol.

Synthesis Route 9

Further Derivitisation of 7-(hydroxy)-2-(morpholin-4-yl)-chromen-4-one to 7-aroyloxy-2-(morpholin-4-yl)-chromen-4-ones

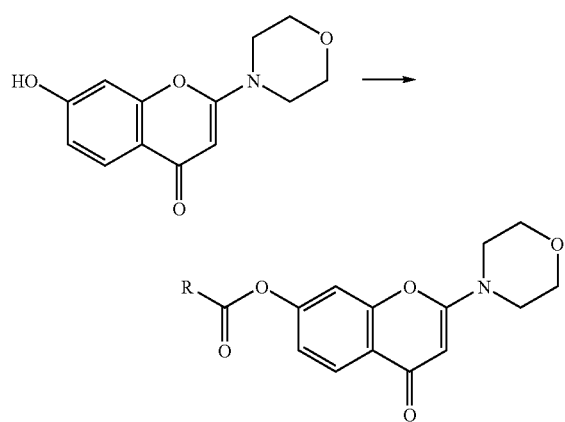

A solution of 7-hydroxy-2-(morpholin-4-yl)-chromen-4-one (299)(0.25 g, 1.0 mmol) in DMF (10 ml) was treated with the appropriate aroyl chloride, followed by pyridine (0.10 ml, 1.2 mmol) at 0° C. The solution was warmed to room temperature and stirred for 16 h. The resultant suspension was diluted with ethyl acetate (100 ml) and washed with 0.5 M hydrochloric acid (50 ml), water (50 ml) and brine (50 ml). The organic extract was dried over sodium sulphate and evaporated in vacuo. The crude product was recrystallised from ethyl acetate.

Use of Compounds of the Invention

The present invention provides active compounds, specifically, active 4-amino-pyran-2-ones, 2-amino-pyran-4-ones, 2-amino-4-ones, and 2-amino-pyridine-isoquinolin-4-ones.

The term "active", as used herein, pertains to compounds which are capable of inhibiting DNA-PK activity, and specifically includes both compounds with intrinsic activity (drugs) as well as prodrugs of such compounds, which prodrugs may themselves exhibit little or no intrinsic activity.

One assay which may be used in order to assess the DNA-PK inhibition offered by a particular compound is described in the examples below.

The present invention further provides a method of inhibiting DNA-PK inhibition in a cell, comprising contacting said cell with an effective amount of an active compound, preferably in the form of a pharmaceutically acceptable composition. Such a method may be practised in vitro or in vivo.

For example, a sample of cells (e.g. from a tumour) may be grown in vitro and an active compound brought into contact with said cells in conjunction with agents that have a known curative effect, and the enhancement of the curative effect of the compound on those cells observed.

The present invention further provides active compounds which inhibit DNA-PK activity as well as methods of methods of inhibiting DNA-PK activity comprising contacting a cell with an effective amount of an active compound, whether in vitro or in vivo.

The invention further provides active compounds for use in a method of treatment of the human or animal body. Such a method may comprise administering to such a subject a therapeutically-effective amount of an active compound, preferably in the form of a pharmaceutical composition.

The term "treatment," as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "therapeutically-effective amount" as used herein, pertains to that amount of an active compound, or a material, composition or dosage from comprising an active compound, which is effective for producing some desired therapeutic effect, commensurate with a reasonable benefit/risk ratio.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g. in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

Where molecular weight (Mw) is quoted as confirmation that the desired compound has been synthesised, this is the molecular weight of the protonated compound detected using LC-MS, and is therefore one unit higher than the actual Mw of the compound, i.e. Mw+1.

Synthesis Details

Route 1

Compound 1

(a) 3-phenyl-3-hydroxy-dithioacrylic acid

Bright orange solid (5.9 g, 75%) from (4.67 ml, 40 mmol) of acetophenone; FT-IR (ATR/cm$^{-1}$) 3055, 1542, 1450, 1234, 1059, 909, 751, 674; $^1$H NMR (CDCl$_3$) δ=7.30 (1H, s); 7.35-8.05 (5H, m), 15.18 (1H, s)

(b) Ethyl 3-phenyl-3-hydroxy-dithioacrylate

Brown oil (3.84 g, 68%) from (4.91 g, 25 mmol) of 3-phenyl-3-hydroxy-dithioacrylic acid; FT-IR (ATR/cm$^{-1}$): 3062, 2970, 2923, 2550, 1395, 1225, 1042, 948, 755; $^1$H NMR (CDCl$_3$) δ=1.31 (3H, t), 3.20 (2H, q), 6.84 (1H, s), 7.34-7.83 (5H, m), 15.06 (1H, s)

(c) 1-Phenyl-3-morpholin-4-yl-3-thioxo-propan-1-one

White crystalline solid (3.26 g, 80%) from (3.64 g, 16.25 mmol) of ethyl 3-phenyl-3-hydroxy-dithioacrylate; FT-IR (ATR/cm$^{-1}$): 3023, 2908, 2871, 1681, 1496, 1433, 1311, 1169, 1103, 953, 748; $^1$H NMR (CDCl$_3$) δ=3.59-3.80 (6H, m); 4.33 (2H, m); 4.72 (2H, s); 7.38-7.96 (5H, m)

(d) 1-phenyl-3-ethylsulfanyl-3-morpholin-4-yl-propenone

Brown oil (3.21 g, 97%)

(e) 4-morpholin-4-yl-6-(phenyl)-pyran-2-one (Compound 1)

White solid (0.38 g, 15%); mp 161-162° C.; FT-IR (ATR/cm$^{-1}$): 3049, 2956, 2901, 2862, 1977, 1628, 1537, 1436, 1109, 761, 687; $^1$H NMR (DMSO) δ=3.63 (4H, t, 4.5 Hz, CH$_2$N), 3.81 (4H, t, 4.5 Hz, CH$_2$O), 5.37 (1H, d, 2 Hz, H-3), 7.17 (1H, d, 2 Hz, H-5), 7.61-7.65 (3H, m, ArH), 8.03-8.08 (2H, m, ArH); UV: $\lambda_{max}$ (MeOH/nm): 291, 250; MS: m/z (LC-MS/ESP+): 258 (M$^+$+1), 211, 179, 133; Calcd C$_{15}$H$_{15}$NO$_3$. 0.1 EtOAc: C 69.51; H, 5.98; N, 5.26. Found: C, 69.54; H, 5.93; N, 4.96.

4-morpholin-4-yl-6-(4-(t-butyl)phenyl)-pyran-2-one (Compound 2)

White needles (0.61 g, 19%); mp 230-232° C.; FT-IR (ATR/cm$^{-1}$): 3109, 3051, 2947, 2862, 1674, 1633, 1511, 1446, 1114, 941, 826, 782; $^1$H NMR (DMSO) δ=1.42 (9H, s, (CH$_3$)$_3$C), 3.62 (4H, m, CH$_2$N), 3.79 (4H, m, CH$_2$O), 5.34 (1H, bs, H-3), 7.10 (1H, bs, H-5), 7.63 (2H, d, 8.5 Hz, ArH), 7.96 (2H, d, 8.5 Hz, ArH); UV: λ$_{max}$(MeOH/nm): 265.5, 235.5; MS: m/z (LC-MS/ESP+): 314 (M$^+$+1); Calcd C$_{19}$H$_{23}$NO$_3$.0.1H$_2$O: C 72.40; H, 7.42; N, 4.44. Found: C, 72.50; H, 7.48; N, 4.18.

4-morpholin-4-yl-6-(4-methoxyphenyl)-pyran-2-one (Compound 3)

White needles (0.43 g, 15%); mp 212-213° C.; FT-IR (ATR/cm$^{-1}$): 2969, 2926, 1681, 1619, 1505, 1442, 1240, 1180, 1113, 789; $^1$H NMR (DMSO) δ=3.60 (4H, t, 4.5 Hz, CH$_2$N); 3.79 (4H, t, 4.5 Hz, CH$_2$O); 3.94 (3H, s, MeO); 5.30 (1H, d, 2 Hz, H-3); 7.02 (1H, d, 2 Hz, H-5); 7.16 (2H, d, 9 Hz, ArH); 7.98 (2H, d, 9 Hz, ArH); UV: λ$_{max}$ (MeOH/nm): 226, 256, 301.5; MS: m/z (LC-MS/ESP+): 288 (M$^+$+1), 157; Calcd C$_{16}$H$_{17}$NO$_4$: C 66.89; H, 5.96; N, 4.88. Found: C, 66.65; H, 6.03; N, 4.51.

4-morpholin-4-yl-6-(4-chlorophenyl)-pyran-2-one (Compound 4)

White needles (0.31 g, 21%) from (1.55 g, 5 mmol) of 1-(4-chloro-phenyl)-3-ethylsulfanyl-3-morpholin-4-yl-propenone; mp 236-237° C.; FT-IR (ATR/cm$^{-1}$): 3040, 2969, 1681, 1624, 1535, 1235, 941, 785; $^1$H NMR (DMSO) δ=3.65 (4H, m, CH$_2$N); 3.83 (4H, m, CH$_2$O); 5.40 (1H, m, H-3); 7.22 (1H, m, H-5); 7.75 (2H, m, ArH); 8.09 (2H, m, ArH); UV: λ$_{max}$ (MeOH/nm): 296.5, 254; MS: m/z (LC-MS/ESP+): 292-294 (M$^+$+1); Calcd C$_{15}$H$_{14}$ClNO$_3$: C 61.76; H, 4.84; N, 4.80. Found: C, 61.55; H, 4.91; N, 4.55.

Route 2-Step (c)

2-Morpholin-1-yl-pyrimido[2,1-a]isoquinolin-4-one (Compound 5)

Prepared from 2-chloro-pyrimido[2,1-a]isoquinolin-4-one (0.230 g, 1 mmol) and morpholine (0.35 ml, 4 mmol) to give white crystals (0.236 g, 0.83 mmol, 83% yield). FT-IR (KBr disc): cm$^{-1}$ 3070, 2983, 2945, 2911, 2864, 1701, 1641, 1574, 1546, 1522, 1488, 1427, 1402, 1286, 1225, 1116, 773. m/z (EI): 281 (M$^+$), 250, 224, 195, 168, 128, 101, 77. $^1$H NMR 200 MHz, DMSO): 3.82 (8H, s, morpholine-H), 5.73 (1H, s, H-3); 7.37 (1H, d, 8 Hz, ArH); 7.75 (1H, m, ArH); 7.77 (1H, d, 5 Hz, ArH); 7.91 (1H, d, 5 Hz, ArH); 8.62 (1H, d, 7.5 Hz, ArH); 8.88 (1H, d, 7.5 Hz, ArH)

2-(Thiomorpholin-4-yl)pyrimido[2,1-a]isoquinolin-4-one (Compound 6)

Pale yellow crystals (0.255 g, 0.86 mmol, 86% yield). Mp=240-242 (C. UV (max=354.5, 335.5, 320, 280.5, 261.5, 232, 200 nm (Methanol). $^1$H NMR (200 MHz, CDCl3) (2.66 (4H, m); 4.06 (4H, m); 5.62 (1H, s); 7.01 (1H, d); 7.62 (3H, m); 8.60 (1H, d); 8.75 (1H, m). ES-MS m/z=298 (M+1). Anal. Calcd for C$_{16}$H$_{15}$N$_3$OS: C, 64.62; H, 5.08; N, 14.13. Found: C, 64.22; H, 4.86; N, 13.94.

2-(2,5-Dimethyl-piperidin-1-yl)pyrimido[2,1-a]isoquinolin-4-one (Compound 7)

White crystals (0.126 g, 0.41 mmol, 41% yield). mp 214-216° C. λ$_{max}$=356, 336, 322, 261.5, 231.5, 200 nm (Methanol). m/z (ES$^+$): 308 (M$^+$+1), 179, 133. $^1$H NMR (200 MHz, CDCl$_3$) δ0.89 (3H, s); 0.93 (3H, s); 1.65 (4H, m); 4.42 (2H, s); 5.62 (1H, s); 6.96 (1H, d); 7.61 (3H, m); 8.59 (1H, d); 8.76 (1H, m). Anal. Calcd. for C$_{19}$H$_{21}$N$_3$O. 0.2CH$_3$OH: C, 73.49; H, 7.00; N, 13.39. Found: C, 73.92; H, 6.77; N, 13.56.

2-(4-Methyl-piperazin-1-ly)pyrimido[2,1-a]isoquinolin-4-one (Compound 8)

White solid (0.095 g, 0.32 mmol, 32% yield. mp=Sublimes above 285° C. m/z (ES$^+$) 295 (MH$^+$), 257, 179. $^1$H NMR (200 MHz, d$_6$-DMSO) δ2.91 (3H, s); 3.44 (8H, m); 5.95 (1H, s); 7.49 (1H, d); 7.95 (1H, m); 8.02 (2H, m); 8.67 (1H, d); 8.99 (1H, m).

2-(3-Hydroxymethyl-piperidin-1-yl)pyrimido[2,1-a]isoquinolin-4-one (Compound 9)

White solid (0.157 g, 0.50 mmol, 50% yield). mp 165-166° C. ESMS m/z (ES$^+$) 310 (M+H), 257, 179. $^1$H NMR (200 MHz, CDCl$_3$) 1.75 (5H, m); 2.39 (1H, m); 3.31 (1H, m); 3.59 (3H, m); 4.09 (2H, m); 5.64 (1H, s); 7.01 (1H, d); 7.63 (3H, m); 8.63 (1H, d); 8.77 (1H, m).

2-[(Tetrahydro-furan-2-ylmethyl)-amino]pyrimido[2,1-a]isoquinolin-4-one (Compound 10)

White solid (0.173 g, 0.58 mmol, 58% yield). mp 174-175° C. ESMS m/z=296 (M+H), 257, 179. $^1$H NMR (200 MHz, CDCl$_3$) δ1.81 (4H, m); 3.56 (2H, d); 3.73 (1H, q); 3.86 (1H, q); 4.07 (1H, m); 5.29 (1H, s, NH); 5.43 (1H, s); 6.96 (1H, d); 7.59 (3H, m); 8.57 (1H, d); 8.76 (1H, d)

2-[Bis-(2-hydroxy-ethyl)-amino]pyrimido[2,1-a]isoquinolin-4-one (Compound 11)

White solid (0.076 g, 0.26 mmol, 26% yield). mp 211-212° C. ESMS m/z=300 (M+1), 257, 179. $^1$H NMR (200 MHz, D$_6$DMSO) δ3.90 (4H, m,); 5.62 (1H, s); 7.38 (1H, d); 7.81 (1H, m); 7.94 (1H, d); 8.58 (1H, d); 8.85 (1H, d). Anal. Calcd for C$_{16}$H$_{17}$N$_3$O$_3$: C, 69.88; H, 6.19; N, 13.55. Found: 69.70; H, 6.27; N, 13.44

2-(3-Hydroxy-pyrrolidin-1-yl)pyrimido[2,1-a]isoquinolin-4-one (Compound 12)

Beige solid (0.211 g, 0.75 mmol, 75% yield). mp 240-241° C. UV λ$_{max}$=248.5, 258.0, 273.5, 344.5, 362.0 nm (Methanol). ESMS m/z=282 (M+1), 257, 179, 133. $^1$H NMR (200 MHz, d$_6$DMSO) δ2.18 (2H, m); 3.45 (2H, m); 3.86 (2H, m); 4.52 (1H, m); 5.17 (1H, s); 7.36 (1H, d); 7.80 (1H, m); 7.94 (2H, d); 8.63 (1H, d); 8.86 (1H, d)

2-(Cis-2,6-dimethylmorpholin-4yl)pyrimido[2,1-a]isoquinolin-4-one (Compound 13)

White crystals (0.088 g, 0.28 mmol, 56% yield). mp 208-209° C. ESMS m/z=310 (M+1), 257, 179, 101. $^1$H NMR (200 MHz, CDCl$_3$) δ1.29 (6H, d); 2.68 (2H, dd); 3.70 (2H, m); 4.30 (2H, m); 5.63 (1H, s); 7.06 (1H, d); 7.67 (3H, m); 8.65 (1H, d); 8.81 (1H, d)

2-[Benzyl-(2-hydroxy-ethyl)-amino]pyrimido[2,1-a]isoquinolin-4-one (Compound 14)

White crystals (0.077 g, 0.22 mmol, 44% yield). ESMS m/z=346 (M+1), 257, 179, 101. $^1$H NMR (200 MHz, d₆DMSO) δ 3.77 (4H, m); 4.97 (2H, m); 5.63 (1H, s); 7.41 (6H, m); 7.95 (3H, m); 8.63 (1H, d); 8.84 (1H, d).

2[(2-hydroxy-ethyl)-methyl-amino]-pyrimido[2,1-a]isoquinolin-4-one (Compound 15)

White crystals (0.079 g, 0.29 mmol, 58% yield). ESMS m/z 270 (M+1), 257, 179, 133, 101. $^1$H NMR (200 MHz, CDCl$_3$) δ 3.15 (3H, s); 3.92 (4H, m); 5.55 (1H, s); 7.00 (1H, d); 7.64 (3H, m); 8.62 (1H, d); 8.73 (1H, d).

2-[(2-Hydroxy-2-phenyl-ethyl)-methyl-amino]-pyrimido[2,1-a]isoquinolin-4-one (Compound 16)

Off-white crystalline solid (0.115 g, 0.33 mmol, 66% yield). mp 195-196° C. UV λ$_{max}$=354, 334.5, 320, 259, 232, 200 nm (Methanol). ESMS m/z=346 (M+1). $^1$H NMR (200 MHz, CDCl$_3$) δ2.94 (3H, s); 3.99 (2H, m); 4.60 (1H, s); 5.13 (1H, m); 5.54 (1H, s); 7.04 (1H, d); 7.36 (5H, m); 7.71 (3H, m); 8.65 (1H, d); 8.82 (1H, m). Anal Calcd for C$_{21}$H$_{19}$N$_3$O$_2$.0.15CH$_3$OH: C, 72.48; H, 5.65; N, 11.98. Found: C, 72.57; H, 5.51; N, 11.89

3-[Methyl-(4-oxo-4H-pyrimido[2,1-a]isoquinolin-2-yl)-amino]-propionitrile (Compound 17)

Off-white crystalline solid (0.067 g, 0.24 mmol, 48% yield). mp 166-167° C. UV λ$_{max}$=352, 334, 316, 200 nm (Methanol). ESMS m/z=279 (M+1). $^1$H NMR (200 MHz, CDCl$_3$) δ2.80 (2H, t); 3.18 (3H, s); 4.08 (2H, t); 5.58 (1H, s); 7.01 (1H, d); 7.71 (3H, m); 8.68 (1H, d); 8.76 (1H, m). Anal Calcd for C$_{16}$H$_{14}$N$_4$O: C, 69.05; H, 5.07; N, 20.13. Found: C, 68.47; H, 4.99; N, 19.93.

2-(2-Thiophen-2-yl-ethylamino)-pyrimido[2,1-a]isoquinolin-4-one (Compound 18)

Off-white crystalline solid (0.115 g, 0.36 mmol, 72% yield). mp 162-163° C. UV λ$_{max}$=352, 334, 318.5, 253, 229.5, 200 nm (Methanol). ESMS m/z=322 (M+1), 301, 181. $^1$H NMR (200 MHz, CDCl$_3$) δ3.15 (3H, m); 3.56 (2H, m); 5.07 (1H, s); 5.47 (1H, s); 6.73 (2H, m); 7.16 (2H, m); 7.61 (3H, m); 8.60 (1H, d); 8.75 (1H, m). Anal. Calcd. for C$_{18}$H$_{15}$N$_3$OS: C, 67.27; H, 4.70; N, 13.07. Found: C, 66.84; H, 4.57; N, 13.07.

2-(2,3-Dihydroxypropylamino)-pyrimido[2,1-a]isoquinolin-4-one (Compound 19)

Off-white crystalline solid (0.045 g, 0.16 mmol, 32% yield). mp 215-216° C. ESMS m/z=286 (M+1), 157, 110. $^1$H NMR (200 MHz, d$_6$-DMSO) δ1.14 (2H, m); 3.47 (2H, m); 3.78 (1H, m); 4.47 (1H, t); 4.77 (1H, t); 5.01 (1H, d); 5.51 (1H, s); 7.36 (1H, d); 7.80 (1H, m); 7.94 (2H, m); 8.63 (1H, d); 8.86 (1H, m)

2-(2-Hydroxypropylamino)-pyrimido[2,1-a]isoquinolin-4-one (Compound 20)

Off-white crystalline solid (0.072 g, 0.27 mmol, 54% yield). mp 199-200° C. ESMS m/z=270 (M+1), 179, 157, 133, 111. $^1$H NMR (200 MHz, d$_6$-DMSO) δ1.23 (3H, d); 3.55 (2H, m); 3.95 (2H, t); 4.93 (1H, d); 5.50 (1H, s); 7.36 (1H, d); 7.82 (1H, m); 7.95 (2H, m); 8.63 (1H, d); 8.88 (1H, m)

2-[2-Hydroxy-2-(3-hydroxy-phenyl)-ethylamino]-pyrimido[2,1-a]isoquinolin-4-one (Compound 21)

Off-white crystalline solid (0.117 g, 0.34 mmol, 68% yield). mp 159-161° C. UV λ$_{max}$=352.5, 333, 317, 257, 231, 200 nm (Methanol). ESMS m/z=348 (M+1), 239, 222, 133. $^1$H NMR (200 MHz, d$_6$-DMSO) δ4.81 (2H, m); 5.52 (1H, s); 5.64 (1H, d); 6.75 (1H, m); 6.96 (2H, m); 7.24 (1H, t); 7.39 (1H, d); 7.82 (1H, m); 7.96 (2H, m); 8.65 (1H, d); 8.89 (1H, m); 9.48 (1H, br s). Anal. Calcd. for C$_{20}$H$_{17}$N$_3$O$_3$.0.3CH$_2$Cl$_2$: C, 65.07; H, 4.65; N, 11.19. Found: C, 65.05; H, 4.92; N, 11.06.

2-(2-Hydroxy-ethylamino)-pyrimido[2,1-a]isoquinolin-4-one (Compound 22)

Off-white crystalline solid (0.091 g, 0.36 mmol, 72% yield). mp 218-221° C. UV λ$_{max}$=352, 333.5, 316, 226.5, 200 nm (Methanol). ESMS m/z=256 (M+1), 229. $^1$H NMR (200 MHz, CDCl$_3$) δ3.45 (2H, m); 3.71 (2H, m); 4.92 (1H, t); 5.49 (1H, s); 7.39 (1H, d); 7.83 (1H, m); 7.96 (2H, m); 8.64 (1H, d); 8.89 (1H, m). Anal. Calcd. for C$_{14}$H$_{13}$N$_3$O$_2$: C, 65.87; H, 5.13; N, 16.46. Found: C, 65.40; H, 4.96; N, 16.12.

Additional examples of compounds synthesised using synthetic route 2 are given in the table below.

| Compound | Structure | Mw LC-MS |
|---|---|---|
| 23 | (structure: pyrimido[2,1-a]isoquinolin-4-one with 2-ethylmorpholinyl substituent) | 310 |
| 24 | (structure: pyrimido[2,1-a]isoquinolin-4-one with 2,5-dihydropyrrol-1-yl substituent) | 264 |
| 25 | (structure: pyrimido[2,1-a]isoquinolin-4-one with pyrrolidin-1-yl substituent) | 266.25 |

Route 3

Examples of compounds synthesised using synthetic route 3 and synthetic route 4 are listed in the following table. An asterix on the structure indicates the place at which the sub stituent and core structure are joined. So, for example, a core structure of

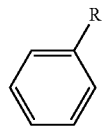

where

defines a compound with structure

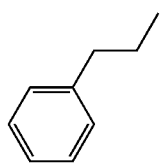

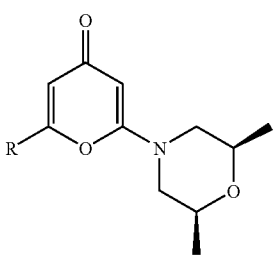

| Compound No. | R | Mw LC-MS | Purity |
|---|---|---|---|
| 26 | 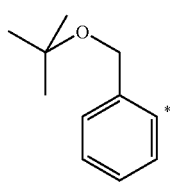 | 372 | 85 |

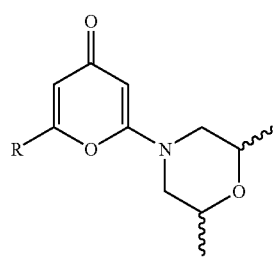

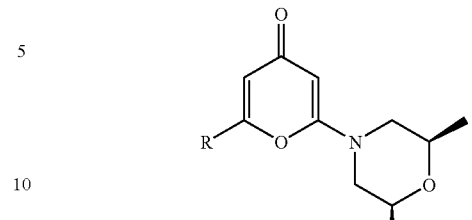

| Compound No. | R | Mw LC-MS | Purity |
|---|---|---|---|
| 27 | 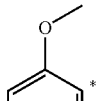 | 346 | 85 |
| 28 | 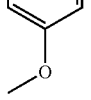 | 376 | 85 |

The wavey bonds,

in the structures of compounds 27 and 28 indicate a bond pointing either up or down (axial or equatorial positions). The structures therefore represent a dimethylmorpholino group having a mixture of cis and trans methyl groups.

Route 4

Examples of compounds synthesised using synthetic route 4 are listed in the tables below.

| Compound No. | Structure | Mw LC-MS | Purity |
|---|---|---|---|
| 29 | 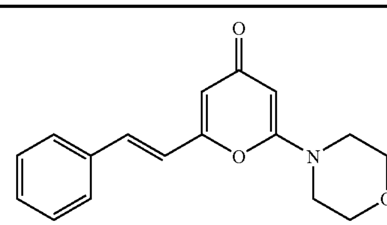 | 284 | 90 |

| Compound No. | R | Mw LC-MS | Purity |
|---|---|---|---|
| | 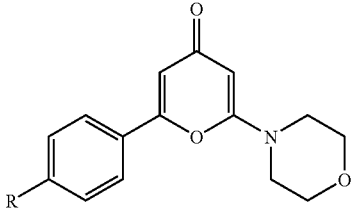 | | |
| 30 | *≡N | 283 | 95 |
| 31 | 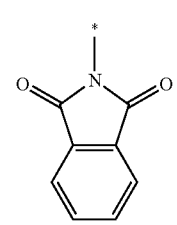 | 417 | 95 |
| 32 | 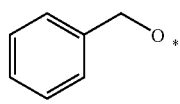 | 364 | 95 |
| 33 | 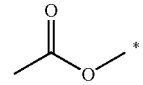 | 330 | 85 |
| 34 | 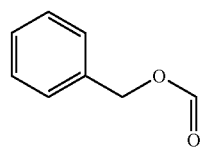 | 392 | 90 |
| 35 | 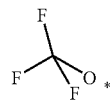 | 342 | 95 |
| 36 |  | 334 | 95 |
| | 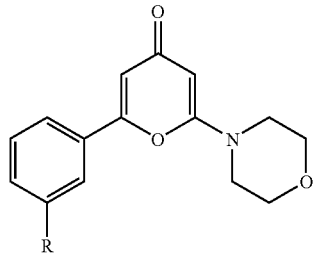 | | |
| 37 | O= * | 286 | 90 |

-continued
| Compound No. | R | Mw LC-MS | Purity |
|---|---|---|---|
| 38 | 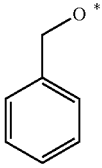 | 364 | 95 |
| 39 |  | 316 | 90 |
| 40 |  | 300 | 85 |
| 41 | 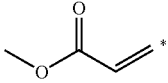 | 342 | 90 |
| 42 | 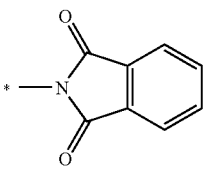 | 417 | 85 |
| 43 | N≡≡* | 283 | 90 |
| 44 |  | 342 | 95 |
| 45 | 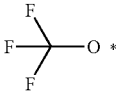 | 302 | 85 |
| 46 | 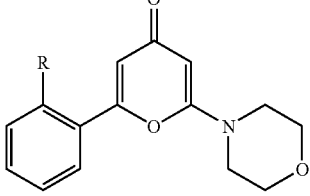 | 364 | 95 |
| 47 | CF$_3$ | 326 | 85 |
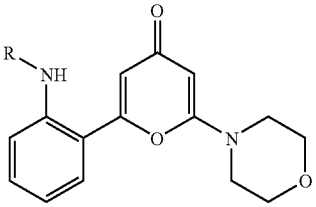
| 48 | H | 273 | 85 |

-continued
| Compound No. | R | Mw LC-MS | Purity |
|---|---|---|---|
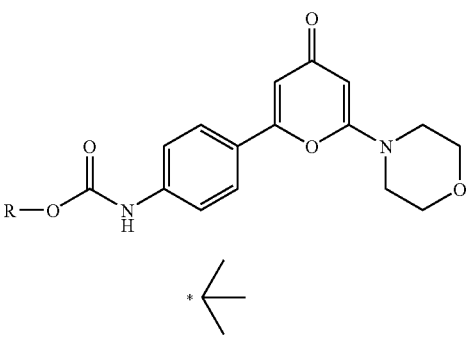
| 49 | 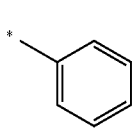 | 373 | 95 |
| 50 | 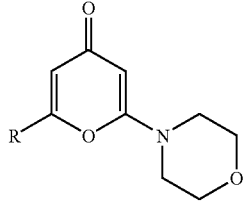 | 407 | 90 |
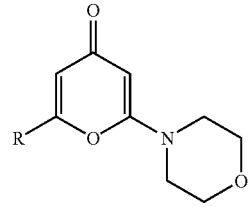
| Compound No. | R | Mw LC-MS | Purity |
|---|---|---|---|
| 51 |  | 266 | 90 |
| 52 |  | 260 | 90 |
| 53 |  | 262 | 90 |
| 54 |  | 261 | 90 |
| 55 | 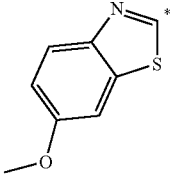 | 346 | 90 |
-continued
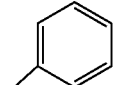
| Compound No. | R | Mw LC-MS | Purity |
|---|---|---|---|
| 56 | 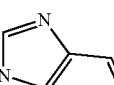 | 330 | 90 |
| 57 | 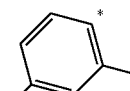 | 343 | 90 |
| 58 | 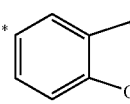 | 322 | 85 |
| 59 | 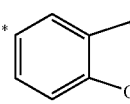 | 300 | 90 |

-continued
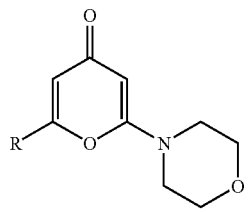
| Compound No. | R | Mw LC-MS | Purity |
|---|---|---|---|
| 60 | 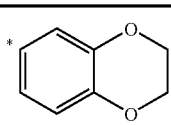 | 316 | 90 |
| 61 |  | 248 | 90 |
| 62 | 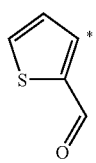 | 292 | 90 |
| 63 | 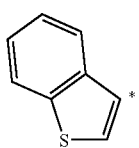 | 314 | 85 |
| 64 | 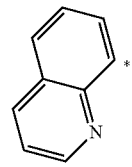 | 309 | 85 |
| 65 | 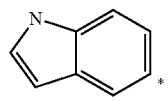 | 297 | 95 |
| 66 |  | 264 | 95 |
-continued
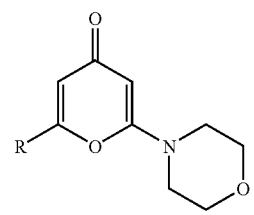
| Compound No. | R | Mw LC-MS | Purity |
|---|---|---|---|
| 67 | | 264 | 85 |
| 68 | | 314 | 95 |
| 69 | | 308 | 95 |
| 70 | 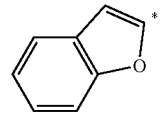 | 336 | 85 |
| 71 | | 298 | 95 |
| 72 | 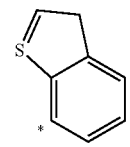 | 314 | 95 |
Route 4a
Examples of compounds synthesised using synthetic route 4a are listed in the following tables.

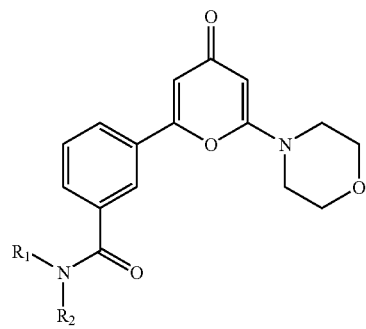
| Compound No. | R₁ | R₂ | Mw LC-MS | Purity |
|---|---|---|---|---|
| 73 | *—≡N | H | 339 | 85 |
| 74 | cyclopropyl | H | 341 | 95 |
| 75 | geranyl | H | 437 | 95 |
| 76 | n-butyl | H | 371 | 95 |
| 77 | n-hexyl | H | 399 | 95 |
| 78 | isopropyl | H | 343 | 95 |
| 79 | cyclohexylmethyl | H | 397 | 90 |
| 80 | cyclobutyl | H | 355 | 90 |
| 81 | n-propyl | H | 343 | 95 |
| 82 | sec-butyl | H | 357 | 95 |
| 83 | neopentyl | H | 385 | 95 |
| 84 | allyl | allyl | 381 | 95 |
| 85 | adamantyl | H | 435 | 95 |

-continued
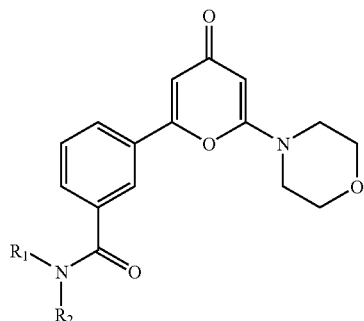
| Compound No. | R₁ | R₂ | Mw LC-MS | Purity |
|---|---|---|---|---|
| 86 | 2,5-dimethoxy-substituted benzyl (* at position with two OMe groups) | H | 481 | 95 |
| 87 | phenyl | phenyl | 481 | 95 |
| 88 | 4-(trifluoromethyl)phenyl | H | 459 | 95 |
| 89 | phenyl | H | 391 | 95 |
| 90 | 2-methoxyphenyl | H | 421 | 95 |
| 91 | 3-fluorophenyl | H | 409 | 95 |
| 92 | 2-phenylethyl | H | 419 | 95 |
| 93 | 3-methylphenyl (with extra methyl) | H | 405 | 95 |

-continued
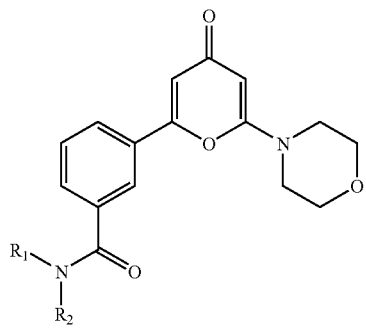
| Compound No. | R₁ | R₂ | Mw LC-MS | Purity |
|---|---|---|---|---|
| 94 | 3,4,5-trimethoxyphenyl | H | 481 | 95 |
| 95 | 4-fluorophenyl | H | 409 | 95 |
| 96 | 1-(4-chlorophenyl)ethyl | H | 454 | 95 |
| 97 | 4-(trifluoromethoxy)phenyl | H | 475 | 90 |
| 98 | 3,5-bis(trifluoromethyl)phenyl | H | 527 | 90 |
| 99 | 3-(trifluoromethyl)phenyl | H | 459 | 95 |

-continued
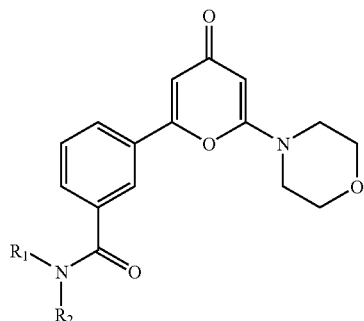
| Compound No. | R₁ | R₂ | Mw LC-MS | Purity |
|---|---|---|---|---|
| 100 | 3-fluoro-5-(trifluoromethyl)phenyl | H | 477 | 95 |
| 101 | 3,5-dimethoxyphenyl | H | 451 | 85 |
| 102 | 2-aminophenyl | H | 406 | 95 |
| 103 | 2-methylphenyl | H | 405 | 95 |
| 104 | 3-aminophenyl | H | 406 | 90 |
| 105 | 4-(dimethylamino)phenyl | H | 434 | 90 |
| 106 | phenyl | 2-(dimethylamino)ethyl | 462 | 90 |
| 107 | 3-(aminomethyl)phenyl | H | 420 | 90 |

-continued
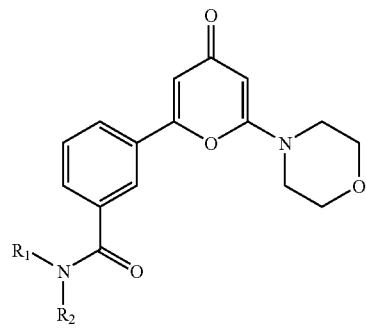
| Compound No. | R₁ | R₂ | Mw LC-MS | Purity |
|---|---|---|---|---|
| 108 | *-CH₂-S-CH₂-(2-Cl,6-F-phenyl) | H | 505 | 95 |
| 109 | *-CH₂-S-CH₂CH₃ | H | 389 | 95 |
| 110 | *-CH₂-S-CH₂CH₂-OH | H | 405 | 95 |
| 111 | *-CH(CF₃)-F (CF₃ group) | H | 383 | 90 |
| 112 | *-CH₂-CN | H | 354 | 90 |
| 113 | *-CH₂CH₂-OH (propanol) | H | 359 | 90 |
| 114 | *-cyclohexyl-OH | H | 399 | 90 |
| 115 | *-(2-hydroxycyclohexyl) | H | 413 | 95 |
| 116 | *-CH(CH₂OH)₂ | H | 375 | 95 |
| 117 | *-CH₂-N(CH₂CH₃)₂ | H | 400 | 90 |
| 118 | *-CH₂CH₂-N(CH₂CH₃)₂ | H | 414 | 90 |

-continued
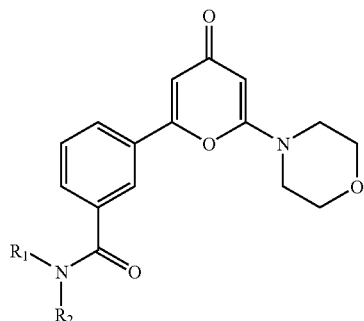
| Compound No. | R₁ | R₂ | Mw LC-MS | Purity |
|---|---|---|---|---|
| 119 | phenyl | CH₂CH₂N(CH₃)₂ | 462 | 90 |
| 120 | CH₂CH₂N(CH₃)₂ | Me | 386 | 90 |
| 121 | CH₂CH₂N(CH₃)₂ | H | 372 | 95 |
| 122 | CH₂CH₂CH₂NHC(O)OCH₂Ph | H | 492 | 95 |
| 123 | 3-nitrobenzoyl-CH₂ | H | 464 | 85 |
| 124 | 3-hydroxybenzoyl-CH₂ | H | 437 | 90 |
| 125 | CH₂CH₂OCH₃ | H | 373 | 95 |
| 126 | CH₂CH₂OPh | H | 421 | 95 |
| 127 | CH₂OCH₃ | H | 359 | 95 |
| 128 | CH₂CH₂OCH₂CH₃ | H | 387 | 95 |

-continued
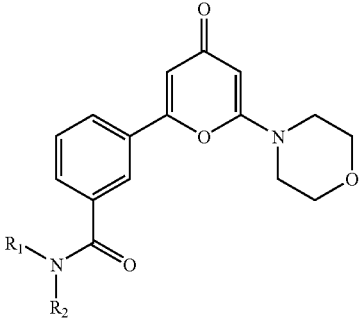
| Compound No. | R₁ | R₂ | Mw LC-MS | Purity |
|---|---|---|---|---|
| 129 | 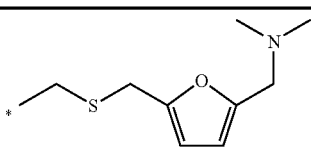 | H | 498 | 90 |
| 130 | 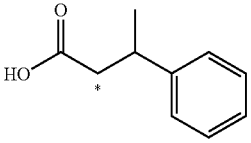 | H | 463 | 90 |
| 131 | 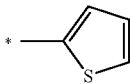 | H | 397 | 85 |
| 132 | 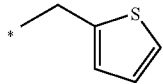 | H | 411 | 95 |
| 133 | 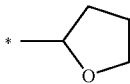 | H | 385 | 95 |
| 134 | 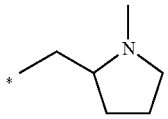 | H | 412 | 90 |
| 135 | 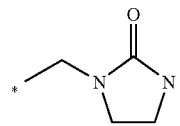 | H | 413 | 90 |

-continued
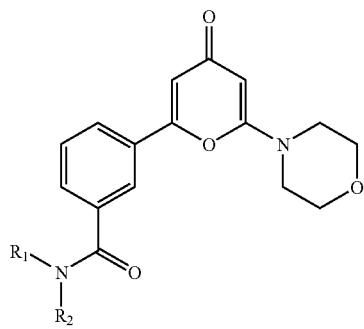
| Compound No. | R₁ | R₂ | Mw LC-MS | Purity |
|---|---|---|---|---|
| 136 | 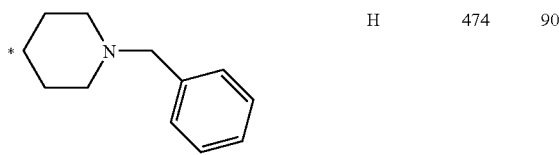 | H | 474 | 90 |
| 137 |  | | 412 | 90 |
| 138 |  | | 417 | 95 |
| 139 |  | | 371 | 95 |
| 140 |  | | 399 | 95 |
| 141 |  | | 398 | 90 |

-continued
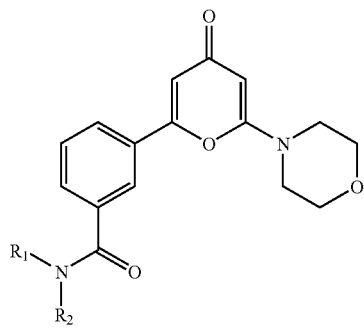
| Compound No. | R₁ | R₂ | Mw LC-MS | Purity |
|---|---|---|---|---|
| 142 | 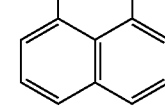 | | 453 | 95 |
| 143 | 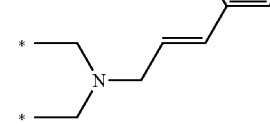 | | 486 | 95 |
| 144 |  | | 385 | 95 |
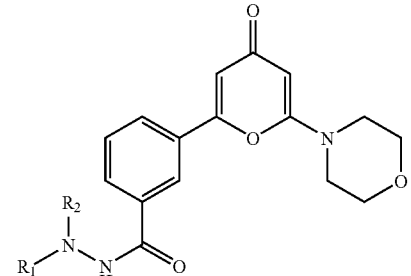
| Compound No. | R₁ | R₂ | Mw LC-MS | Purity |
|---|---|---|---|---|
| 145 | H | H | 316 | 85 |
| 146 | 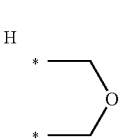 | | 386 | 90 |
| 147 | 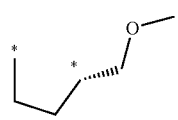 | | 414 | 95 |

-continued
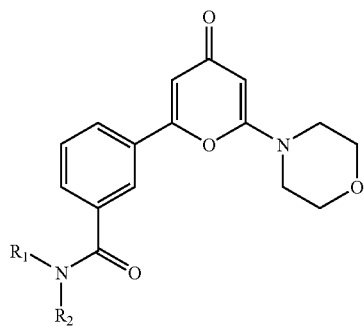
| Compound No. | R₁ | R₂ | Mw LC-MS | Purity |
|---|---|---|---|---|
| 148 | *−CH₂−N(−)−CH₂−* (N-methyl) | | 399 | 90 |
Route 4b
Examples of compounds synthesised using synthetic route 4b are listed in the following tables.
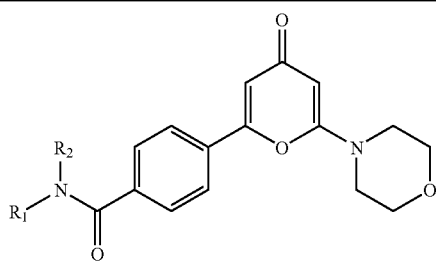
| Compound No. | R₁ | R₂ | Mw LC-MS | Purity |
|---|---|---|---|---|
| 149 | *−≡N | H | 339 | 90 |
| 150 | *−(CH₂)₅−CH₃ | H | 399 | 90 |
| 151 | *−cyclohexyl-tBu | H | 439 | 90 |
| 152 | Me | H | 315 | 85 |
| 153 | *−cyclopropyl | H | 341 | 85 |
| 154 | *−geranyl | H | 437 | 90 |

-continued
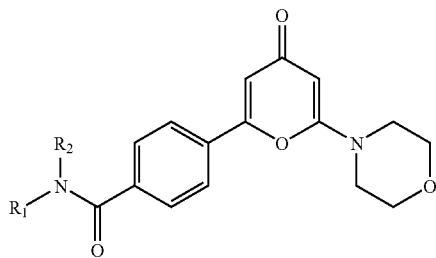
| Compound No. | R₁ | R₂ | Mw LC-MS | Purity |
|---|---|---|---|---|
| 155 | *–CH₂CH₂CH₂CH₃ (n-butyl) | H | 371 | 90 |
| 156 | *–cyclohexyl (via CH₂) | H | 397 | 90 |
| 157 | *–CH₂CH(CH₃)CH₂CH₃ | H | 385 | 90 |
| 158 | *–CH₂CH(CH₃)₂ | H | 371 | 90 |
| 159 | *–CH(CH₃)₂ | H | 343 | 90 |
| 160 | *–cyclohexyl (2-methyl) | H | 394 | 90 |
| 161 | *–cyclobutyl | H | 355 | 90 |
| 162 | *–2,4,6-trimethoxyphenyl | H | 481 | 90 |
| 163 | *–2-methylphenyl | H | 405 | 90 |
| 164 | *–3-nitrophenyl | H | 436 | 90 |

-continued
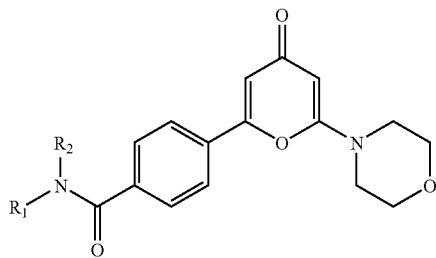
| Compound No. | R₁ | R₂ | Mw LC-MS | Purity |
|---|---|---|---|---|
| 165 | 2,4-dimethoxyphenyl | H | 451 | 90 |
| 166 | phenyl | phenyl | 481 | 90 |
| 167 | 4-methoxybenzyl | H | 435 | 90 |
| 168 | 2-methoxyphenyl | H | 421 | 90 |
| 169 | 3-fluorophenyl | H | 409 | 90 |
| 170 | phenethyl | H | 419 | 90 |
| 171 | 3-methylphenyl | H | 405 | 90 |

-continued
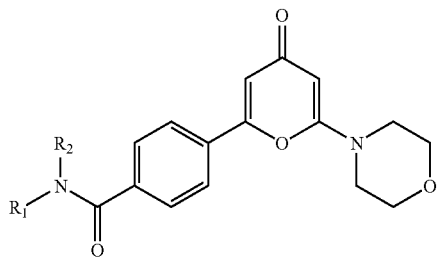
| Compound No. | R₁ | R₂ | Mw LC-MS | Purity |
|---|---|---|---|---|
| 172 | 3,4,5-trimethoxyphenyl | H | 481 | 90 |
| 173 | 1-(4-chlorophenyl)ethyl | H | 454 | 90 |
| 174 | 4-methoxyphenyl | H | 421 | 90 |
| 175 | 4-(trifluoromethoxy)phenyl | H | 475 | 90 |
| 176 | 3,5-bis(trifluoromethyl)phenyl | H | 527 | 90 |
| 177 | 2,3-dimethoxyphenyl | H | 451 | 90 |
| 178 | 3-(trifluoromethyl)phenyl | H | 459 | 90 |

-continued
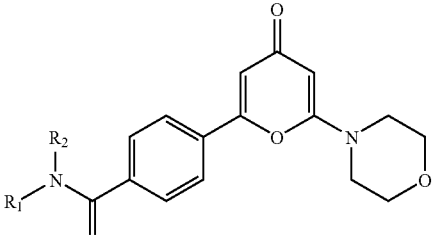
| Compound No. | R₁ | R₂ | Mw LC-MS | Purity |
|---|---|---|---|---|
| 179 | 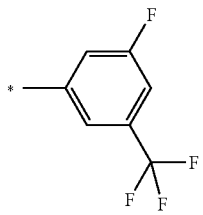 | H | 477 | 90 |
| 180 | 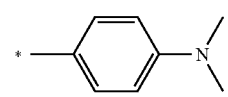 | H | 419 | 90 |
| 181 | 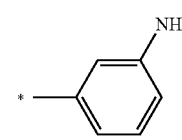 | H | 434 | 85 |
| 182 | 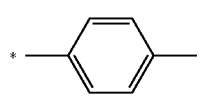 | H | 406 | 90 |
| 183 | 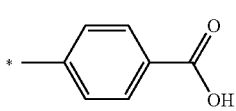 | H | 405 | 90 |
| 184 | 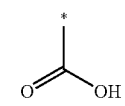 | H | 435 | 85 |
| 185 | 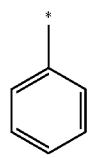 | 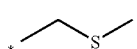 | 449 | 90 |
| 186 | ``*``—CH₂—S—CH₃ | H | 375 | 90 |
| 187 | 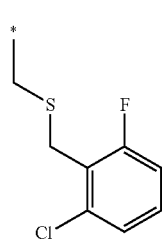 | H | 504 | 90 |

-continued
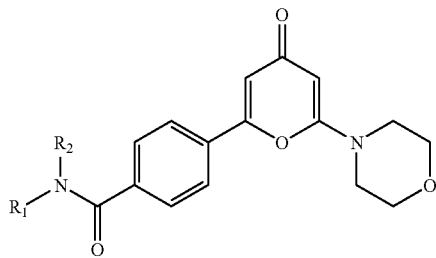
| Compound No. | R₁ | R₂ | Mw LC-MS | Purity |
|---|---|---|---|---|
| 188 | *–CH₂–S–CH₂CH₂–OH | H | 405 | 90 |
| 189 | *–C≡N | H | 340 | 90 |
| 190 | *–CH(CH₂OH)(CH₂OH) (1,3-propanediol) | H | 375 | 90 |
| 191 | 2-hydroxycycloheptyl* | H | 427 | 90 |
| 192 | *–CH(CH₂OH)(CH₂CH₂–S–CH₃) | H | 419 | 90 |
| 193 | *–cyclohexyl–OH | H | 399 | 90 |
| 194 | *–CH₂–C(=O)–O–C(CH₃)₃ | H | 415 | 90 |
| 195 | methyl 2-(4-nitrobenzyl) propanoate* | H | 508 | 90 |
| 196 | methyl 2-phenyl acetate* | H | 449 | 90 |

-continued
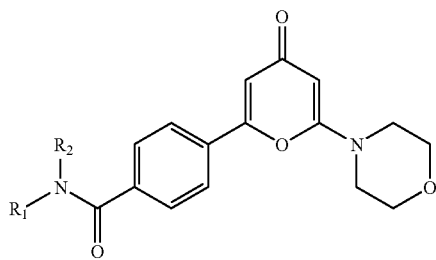
| Compound No. | R₁ | R₂ | Mw LC-MS | Purity |
|---|---|---|---|---|
| 197 | (3,3-dimethyl-butanoic acid with OH) | H | 415 | 85 |
| 198 | (3-phenyl-butanoic acid) | H | 463 | 90 |
| 199 | (3-(4-nitrophenyl)-propanoic acid) | H | 495 | 90 |
| 200 | (3-phenylpropyl methyl ether) | H | 449 | 90 |
| 201 | (2-methoxyethyl) | H | 373 | 90 |
| 202 | (2-phenoxyethyl) | H | 421 | 90 |
| 203 | (N-Cbz-ethylamine) | H | 492 | 90 |
| 204 | (tetrahydrofuran-2-ylmethyl) | H | 385 | 90 |
| 205 | (1-benzylpiperidin-4-yl) | H | 474 | 90 |

-continued
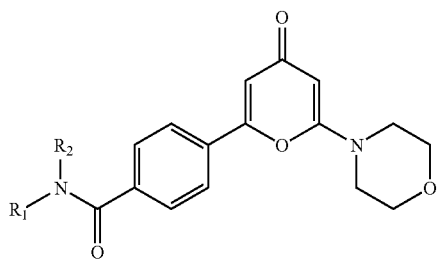
| Compound No. | R₁ | R₂ | Mw LC-MS | Purity |
|---|---|---|---|---|
| 206 | (1-azabicyclo[2.2.1]heptane) | H | 410 | 90 |
| 207 | (1-methylpyrrolidin-2-yl)methyl | H | 412 | 90 |
| 208 | piperidin-1-ylmethyl | H | 412 | 90 |
| 209 | (4-benzylpiperazin-1-yl)methyl | H | 503 | 90 |
| 210 | 2-thienyl | H | 397 | 90 |
| 211 | 2-furyl | H | 381 | 90 |
| 212 | 1H-imidazol-4-ylmethyl | H | 394 | 90 |
| 213 | pyridin-2-ylmethyl | H | 406 | 85 |
| 214 | pyridin-2-yl | H | 392 TFA salt | 90 |

-continued
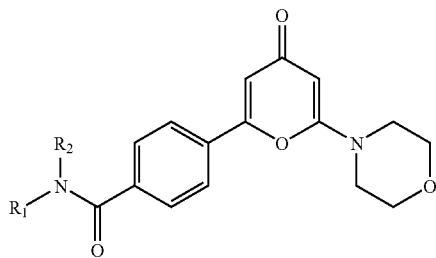
| Compound No. | R₁ | R₂ | Mw LC-MS | Purity |
|---|---|---|---|---|
| 215 | *-CH₂CH₂-CH(*)-C(O)OEt | | 441 | 90 |
| 216 | 1,8-naphthyl (*,*) | | 453 | 90 |
| 217 | 4,5-dimethoxy-benzyl bridge (*,*) | | 477 | 90 |
| 218 | o-xylylene (*,*) | | 417 | 90 |
| 219 | *-CH₂CH₂CH₂CH₂-* | | 367 | 90 |
| 220 | *-CH₂-S-CH₂-* | | 387 | 90 |
| 221 | *-CH₂-CH(OH)-CH₂-* | | 385 | 90 |
| 222 | *-CH(CH₃)-CH(OH)-... * | | 371 | 90 |

Route 4c(i)

Examples of compounds synthesised according to synthetic route 4c(i) are listed in the following tables.

| Compound No. | R₁ | R₂ | Mw LC-MS | Purity |
|---|---|---|---|---|
| 223 | (*CH(Et)CH₂OMe) | * | 414 TFA salt | 90 |

| Compound No. | R₁ | R₂ | Mw LC-MS | Purity |
|---|---|---|---|---|
| 224 | cyclooctyl | H | 397 | 90 |
| 225 | *—C≡N | H | 326 | 90 |
| 226 | *CH₂CH₂SMe | H | 361 | 90 |
| 227 | *C(O)OC(CH₃)₃ | H | 401 | 90 |
| 228 | 2-(CF₃)phenyl | H | 445 | 90 |
| 229 | 2,4-difluorophenyl | H | 413 | 90 |
| 230 | 2-methylphenyl (o-tolyl) | H | 391 | 90 |
| 231 | indanyl | H | 403 | 90 |
| 232 | *CH₂C(O)OMe-(4-NO₂-phenyl) | H | 491 | 85 |
| 233 | 2-thienyl | H | 383 | 90 |
| 234 | 2-thienylmethyl | H | 397 | 90 |
| 235 | *CH₂CH₂CH₂* | * | 341 | 90 |
| 236 | *CH(CH₂CH₃)C(O)OEt, * | | 427 | 90 |

-continued

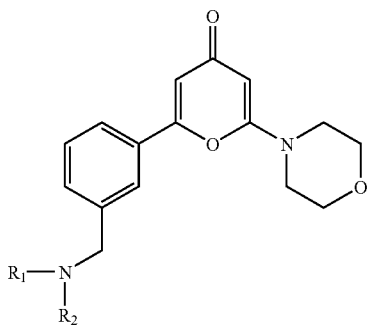

| Compound No. | R₁ | R₂ | Mw LC-MS | Purity |
|---|---|---|---|---|
| 237 | (naphthalene-1,8-diyl, both *) | | 439 | 90 |

Route 4c(ii)

Examples of compounds synthesised according to synthetic route 4c(ii) are listed in the following tables.

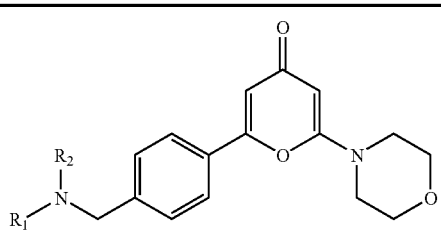

| Compound No. | R₁ | R₂ | Mw LC-MS | Purity |
|---|---|---|---|---|
| 238 | isobutyl | H | 357 | 85 |
| 239 | cyclohexyl | H | 383 | 85 |
| 240 | 4-methylcyclohexyl | H | 383 | 85 |
| 241 | neopentyl | H | 371 | 85 |

-continued

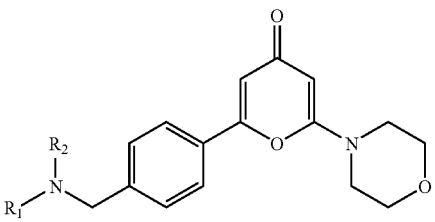

| Compound No. | R₁ | R₂ | Mw LC-MS | Purity |
|---|---|---|---|---|
| 242 | 2-(trifluoromethyl)phenyl | H | 445 | 85 |
| 243 | diphenylmethyl | H | 453 | 85 |
| 244 | 2,4-dimethoxyphenyl | H | 437 | 85 |
| 245 | 4-(trifluoromethyl)phenyl | H | 445 | 85 |
| 246 | phenyl | Me | 391 | 85 |
| 247 | methyl phenylacetate | H | 435 | 85 |
| 248 | 2-methoxyphenyl | H | 407 | 85 |
| 249 | 3-fluorophenyl | H | 395 | 85 |

-continued
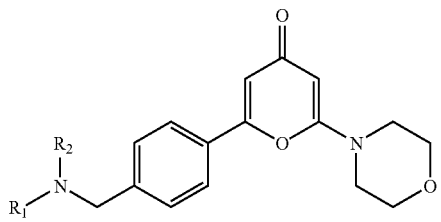
| Compound No. | R₁ | R₂ | Mw LC-MS | Purity |
|---|---|---|---|---|
| 250 | 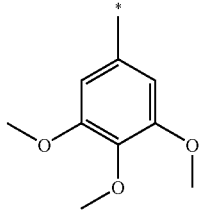 | H | 467 | 85 |
| 251 | 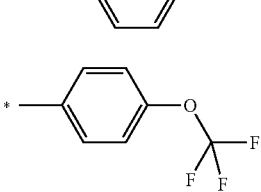 | H | 395 | 85 |
| 252 | 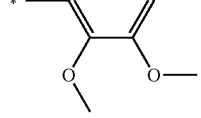 | H | 461 | 85 |
| 253 | 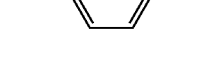 | H | 437 | 85 |
| 254 | 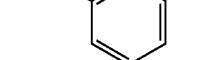 | H | 391 | 85 |
| 255 | 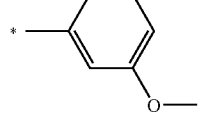 | H | 392 | 85 |
| 256 | | H | 437 | 85 |
| 257 | 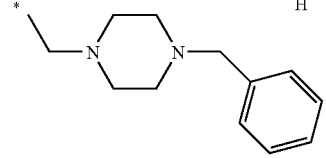 | H | 489 | 85 |
-continued
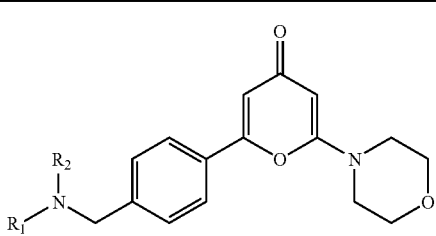
| Compound No. | R₁ | R₂ | Mw LC-MS | Purity |
|---|---|---|---|---|
| 258 | 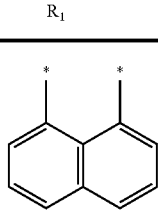 | | 439 | 85 |
| 259 | 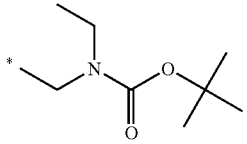 | | 456 | 85 |
| 260 | 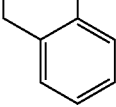 | | 403 | 85 |
| 261 | 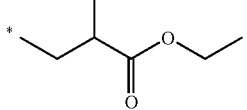 | | 427 | 85 |
| 262 | 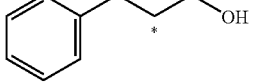 | H | 449 | 85 |
| 263 | | H | 384 | 85 |
Route 4d(iii)
Examples of compounds synthesised according to synthetic method 4d(iii) (from a precursor synthesised according to route 4d(ii)) are listed in the following tables.

| Compound No. | R | Mw LC-MS | Purity |
|---|---|---|---|
| 265 | methyl acetate-O-CH2-* | 373.03 | 90 |
| 266 | isopropyl acetate-* | 401.09 | 90 |
| 267 | *-CH2CH2-O-C(O)CH3 | 387.06 | 90 |
| 268 | *-CH2CH2-OH | 345 | 90 |
| 269 | *-CH2-C(O)-O-CH2CH3 | 387.06 | 90 |
| 270 | phenyl-S-CH2-* | 423 | 90 |
| 271 | 2-thienyl-* | 397 | 90 |
| 272 | 2-furyl-* | 367 | 90 |
| 273 | 4-Cl, 3-OMe phenyl-* | 441.54 | 90 |
| 274 | phenyl-O-CH2CH2-* | 421.12 | 90 |
| 275 | 3-Cl, 2-OMe phenyl-* | 441.54 | 90 |
| 276 | 2-NO2 phenyl-* | 422 | 90 |
| 277 | 2-methyl, 6-OC(O)CH3 phenyl-* | 449.13 | 85 |
| 278 | 2-OCF3 phenyl-* | 461.07 | 85 |
| 279 | pyrrolidine-N-C(O)-CF3 * | 466.09 | 90 |

| Compound No. | R | Mw LC-MS | Purity |
|---|---|---|---|
| 280 | phenyl-* | 420 | 90 |

-continued

| Compound No. | R | Mw LC-MS | Purity |
|---|---|---|---|
| 281 | (ethyl benzoate group, *-substituted) | 480 | 90 |

Route 4d(iv)

Examples of compounds made according to synthetic route 4d(iv) (from a precursor synthesised according to route 4d(i)) are listed in the tables below.

| Compound No. | R₁ | R₂ | Mw LC-MS | Purity |
|---|---|---|---|---|
| 282 | (phenyl acetate group, *-substituted) | H | 435 | 85 |

Route 4d(v)

Examples of compounds synthesised according to route 4d(v) (from a precursor synthesised according to route 4d(i)) are listed in the tables below.

| Compound No. | R | Mw LC-MS | Purity |
|---|---|---|---|
| 264 | (1-(4-chlorophenyl)-cyanomethyl group, *-substituted) | 436 | 85 |

Route 5

Compound 283

(a) Methyl 3(4-chlorophenyl)-3-oxo-triphenylphosphanyl-propionate

Purification by column chromatography (ethyl acetate:petroleum ether 40-60°, 3:2) yielded to a white solid (3.41 g, 77.2%); mp 136° C.; IR (KBr/cm⁻¹): 3074, 3056, 2940, 1662, 1314, 1247, 1105, 1077, 752, 695; ¹H NMR (CDCl₃) δ=3.07 (3H, s), 7.18-7.72 (19H, m); hMS m/z (EI): 472.0993 (M⁺, Calcd 472.0995 for $C_{28}H_{22}O_3PCl$), 472, 361, 277, 201, 163.

(b) Methyl 3-(4-chlorophenyl) propiolate

Purification by column chromatography (ethyl acetate:petroleum ether 40-60°, 15:85) yielded to a white solid (1.17 g, 88.5%); mp 90° C.; ¹H NMR (CDCl₃) δ=3.77 (s, 3H), 7.27-7.65 (4H, m); IR (KBr/cm⁻¹): 3049, 3035, 2964, 2226, 1718, 1489, 1293, 1170, 823, 721; HRMS m/z (EI): 194.0130 (M⁺, Calcd 194.0135 for $C_{10}H_7O_2Cl$), 194, 163, 136, 99, 74.

(c) 4-[(4-chlorophenyl)-2-oxo-3-butynyl) carbonyl] morpholine lithium salt yielded to a white solid (0.42 g, 50%); mp>320° C.; ¹H NMR (d⁶-DMSO) δ=3.46 (4H, m), 3.61 (4H, m), 5.06 (1H, m), 7.56 (4H, s); IR (KBr/cm⁻¹): 3407, 3091, 2961, 2200, 1571, 1506, 1230, 1116, 961, 755; HRMS m/z (EI): 291.0445 (M⁺, Calcd 291.0662 $C_{15}H_{14}ClNO_3$), 291, 263, 163, 136, 86.

(d) 6-(4-chlorophenyl)-2-(4-morpholinyl)-4H-pyran-4-one (Compound 284)

Purification by column chromatography (ethyl acetate:petroleum ether 40-60°, 15:85) yielded to a white solid (0.15 g, 50%); mp 250° C.; IR (KBr/cm⁻¹): 3071, 2965, 1643, 1559, 1410, 1124, 899, 854; ¹H NMR (CDCl₃) δ=3.41 (4H, t), 3.83 (4H, t), 5.45 (1H, d), 6.51 (1H, d), 7.42 (2H, d); 7.58 (2H, d); HRMS m/z (EI): 291.0666 (M⁺, Calcd 291.0662 for $C_{15}H_{14}O_3NCl$), 291-293, 263-265, 205-207, 136-138; UV: λ$_{max}$(MeOH)=354.0 nm; Anal. Calcd for $C_{15}H_{14}O_3NCl$.

0.1H$_2$O: C, 61.38; H, 4.88; N, 4.77; Cl, 12.08. Found: C, 61.58; H, 4.99; N, 4.34; Cl, 12.40.

2-(4-Morpholinyl)-6-phenyl-4H-pyran-4-one (Compound 285)

Pale green solid (0.38 g, 63%); mp 148-150° C.; IR (KBr/cm$^{-1}$): 1648, 1561, 1230, 1108, 1030, 896, 775. $^1$H NMR: δ (d$_6$-DMSO): 3.55 (4H, m, CH$_2$N), 3.85 (4H, m, CH$_2$O), 5.54 (1H, d), 6.75 (1H, d), 7.63 (3H, m, Ar—H), 8.00 (2H, m, Ar—H); HRMS m/z (EI): 257.1047 (M$^+$, Calcd 257.1052 for C$_{15}$H$_{15}$NO$_3$), 257, 229, 200, 171, 131, 111, 102, 86, 77; Anal. Calcd for C$_{15}$H$_{15}$NO$_3$.H$_2$O: C, 68.53; H, 5.71; N, 5.33. Found: C, 68.53; H, 5.90; N, 5.14.

6-(2-methoxyphenyl)-2-(4-morpholinyl)-4H-pyran-4-one (Compound 286)

White solid (0.297 g, 23%); mp 125-127° C.; IR (KBr/cm$^{-1}$): 3077, 3001, 2968, 1641, 1604, 1562, 1404, 1241, 1121, 1019, 862, 761; $^1$H NMR (CDCl$_3$) δ=3.34 (4H, t), 3.75 (4H, t), 3.83 (3H, s), 5.39 (1H, d), 6.72 (1H, d), 6.93-7.01 (2H, m), 7.33-7.52 (2H, m); HRMS m/z (EI): 287.1171 (M$^+$, Calcd 287.1158 for C$_{16}$H$_{17}$O$_4$N), 287, 259, 244, 131, 111; UV: λ$_{max}$(MeOH)=358 nm; Anal. Calcd for C$_{16}$H$_{17}$O$_4$N. 0.2H$_2$O: C, 66.06; H, 6.03; N, 4.81. Found: C, 66.13; H, 5.90; N, 4.73.

6-(3-methoxyphenyl)-2-(4-morpholinyl)-4H-pyran-4-one (Compound 287)

White solid (1.33 g, 99%); mp 115-117° C.; IR (KBr/cm$^{-1}$): 3078, 2975, 1647, 1536, 1420, 1239, 1123, 879, 793; $^1$H NMR (CDCl$_3$) δ=3.41 (4H, t), 3.84 (7H, m), 5.45 (1H, d), 6.53 (1H, d), 6.97-7.41 (4H, m); HRMS m/z (EI): 287.1154 (M$^+$, Calcd 287.1158 for C$_{16}$H$_{17}$O$_4$N), 287, 259, 200, 173, 135, 102; UV: λ$_{max}$(MeOH)=356 nm; Anal. Calcd for C$_{16}$H$_{17}$O$_4$N: C, 66.67; H, 5.93; N, 4.62. Found: C, 66.9; H, 5.93; N, 4.62.

6-(4-methoxyphenyl)-2-(4-morpholinyl)-4H-pyran-4-one (Compound 288)

White solid (1.29 g, 96%); mp 220° C.; IR (KBr/cm$^{-1}$): 3085, 2968, 1649, 1600, 1513, 1405, 1259, 1190, 835; $^1$H NMR (CDCl$_3$) δ=3.40 (4H, t), 3.82 (4H, t), 3.84 (3H, s), 5.41 (1H, d), 6.43 (1H, d), 6.95 (d, 2H), 7.59 (d, 2H); HRMS m/z (EI): 287.1158 (M$^+$, Calcd 287.1158 for C$_{16}$H$_{17}$O$_4$N), 287, 287, 259, 201, 132; UV: λ$_{max}$(MeOH)=358 nm; Anal. Calcd for C$_{16}$H$_{17}$O$_4$N: C, 66.67; H, 5.93; N, 4.62. Found: C, 66.58; H, 5.90; N, 4.84.

6-(4-tert-butylphenyl)-2-(4-morpholinyl)-4H-pyran-4-one (Compound 289)

White solid (0.94 g, 75.5%); mp 156° C.; IR (KBr/cm$^{-1}$): 3071, 3058, 2960, 1648, 1571, 1404, 1362, 1121, 900, 826; $^1$H NMR (CDCl$_3$) δ=1.28 (9H, s), 3.37 (4H, t), 3.78 (4H, t), 5.39 (1H, d), 6.47 (1H, d), 7.42 (2H, d), 7.54 (2H, d); HRMS m/z (EI): 313.1684 (M$^+$, Calcd 313.1678 for C$_{19}$H$_{23}$O$_3$N), 313, 285, 270, 256, 213, 143; UV: λ$_{max}$(MeOH)=358 nm; Anal. Calcd for C$_{19}$H$_{23}$O$_3$N. 0.2H$_2$O: C, 71.99; H, 7.44; N, 4.42. Found: C, 72.14; H, 7.35; N, 4.44.

6-(2-fluorophenyl)-2-(4-morpholinyl)-4H-pyran-4-one (Compound 290)

White solid (0.67 g, 76%); mp 137-138° C.; IR: (KBr)/(cm$^{-1}$): 3059, 3028, 2928, 1640, 1570, 1405, 1119, 756; $^1$H NMR (CDCl$_3$) δ=3.38 (4H, t), 3.76 (4H, t), 5.40 (1H, d), 6.54 (1H, d), 7.07-7.23 (2H, m), 7.34-7.57 (2H, m); HRMS (EI) m/z 275.0950 [M$^+$ calcd 275.0958 for C$_{15}$H$_{14}$O$_3$NF], 275, 247, 189, 161, 134, 120, 86; UV: λ$_{max}$(MeOH)=244.5 nm; Anal. Calcd for C$_{10}$H$_7$O$_2$F. 0.2CH$_2$Cl$_2$: C, 64.6; H, 5.2; N, 5.0. Found: C, 64.8; H, 5.0; N, 4.9.

6-(3-fluorophenyl)-2-(4-morpholinyl)-4H-pyran-4-one (Compound 291)

White solid (0.10 g, 11%); mp 169-170° C.; IR: (KBr)/(cm$^{-1}$): 3055, 2929, 1650, 1564, 1403, 1245, 1114, 877; $^1$H NMR (CDCl$_3$) δ=3.39 (4H, t), 3.76 (4H, t), 5.40 (1H, d), 6.49 (1H, d), 7.08-7.45 (4H, m); HRMS (EI) m/z 275.0946 [M$^+$ calcd 275.0958 for C$_{15}$H$_{14}$O$_3$NF], 275, 247, 189, 161, 120, 95; UV: λ$_{max}$(MeOH)=247 nm; Anal. Calcd for C$_{10}$H$_7$O$_2$F. 0.5CH$_2$Cl$_2$: C, 58.6; H, 4.8; N, 4.4. Found: C, 58.8; H, 4.6; N, 4.3.

6-(4-fluorophenyl)-2-(4-morpholinyl)-4H-pyran-4-one (Compound 292)

White solid (0.319 g, 82%); mp 216-217° C.; IR (KBr/cm$^{-1}$): 3065, 3010, 2969, 2910, 1641, 1560, 1411, 1239, 1123, 856, 784; $^1$H NMR (CDCl$_3$) δ=3.36 (4H, t), 3.78 (4H, t), 5.39 (1H, d), 6.43 (1H, d), 7.04-7.16 (2H, m), 7.55-7.65 (2H, m); HRMS (EI) m/z 275.0946 [M$^+$ calcd 275.0958 for C$_{15}$H$_{14}$O$_3$NF], 275, 247, 210, 182, 120, 86; UV: max(MeOH)=247 nm; Calcd for C$_{10}$H$_7$O$_2$F. 0.3CH$_2$Cl$_2$: C, 61.1; H, 4.9; N, 4.7. Found: C, 61.4; H, 4.4; N, 4.7.

Route 6

Compound 293

(a) Methyl 1-hydroxy-2-naphthoate

Prepared from 1-hydroxy-2-naphthoic acid (9.4 g, 50 mmol), affording 2.85 g (14 mmol, 28% yield) as an off white solid: mp 78-79° C. IR (KBr): 3051; 2953; 1662; 1635; 1438; 1336; 772 cm$^{-1}$. $^1$H NMR (200 MHz., CDCl$_3$) δ 3.91 (3H, s); 7.19 (1H, d, J=9 Hz.); 7.48 (2H, m); 7.68 (2H, d, J=9 Hz.); 8.33 (1H, d, J=8 Hz.); 11.88 (1H, s). EIMS m/z=202 (M+); 170; 114.

(b) 1-(1-Hydroxynaphth-2-yl)-3-(morpholin-4-yl)-propan-1,3-dione

Prepared from methyl 1-hydroxy-2-naphthoate (2.28 g, 11.3 mmol), affording 2.49 g (8.3 mmol, 74% yield) of the title compound as an off-white powder. mp 128-130° C. IR (KBr) 1658; 1620; 1223; 1114; 804 cm$^{-1}$. $^1$H NMR (200 MHz., d$_6$-DMSO) δ 3.61 (4H, m); 3.72 (4H, m); 4.50 (2H, s); 7.49 (1H, d, 8.9 Hz.); 7.72 (1H, dt, J=1.2 Hz., 7.5 Hz.); 7.85 (1H, dt, J=1.2 Hz., 8.2 Hz.); 7.92 (1H, d, J=8.9 Hz.); 8.03 (1H, d, 8.0 Hz.); 8.46 (1H, d, 8.2 Hz.); 13.72 (1H, bs). EIMS m/z=299 (M+); 212; 170; 87.

(c) 7,8-Benzo-2-(morpholin-4-yl)-chromen-4-one (Compound 293)

Prepared from 1-(1-hydroxynaphth-2-yl)-3-(morpholin-4-yl)-propan-1,3-dione (2.4 g, 8.0 mmol), affording 1.43 g (5.1 mmol, 63% yield) of the desired compound as white crystals. mp 267-269° C. IR (KBr) 1641; 1626; 1605; 1509; 1562; 1420; 1240; 117; 920 cm$^{-1}$. $^1$H NMR (200 MHz., d$_6$-DMSO) δ 3.74 (4H, m); 3.91 (4H, m); 5.79 (2H, s); 7.88 (1H, d, 8.9 Hz.); 8.02 (2H, m); 8.16 (1H, m); 8.56 (1H, m). EIMS m/z=281 (M+); 224; 196; 170.

8-Phenyl-2-(morpholin-4-yl)-chromen-4-one (Compound 294)

Off-white powder (0.770 g, 2.51 mmol, 74% yield): mp 183-185° C. IR (KBr): 3419; 1621; 1563; 1414; 1252; 1119;

990; 755; 700 cm$^{-1}$. $^1$H NMR (200 MHz., d$_6$-DMSO) δ 3.45 (4H, m, morpholine); 3.74 (4H, m, morpholine); 5.66 (1H, s, chromenone 3-H); 7.57 (4H, m); 7.73 (3H, m); 8.06 (1H, m). $^{13}$C NMR (50 MHz., d$^6$-DMSO) δ 44.8; 65.5; 86.4; 123.5; 124.4; 125.1; 128.4; 128.8; 129.7; 130.2; 133.5; 136.0; 150.4; 162.5; 175.4. EIMS m/z=307 (M+); 292; 250; 222; 196; 168; 139. Anal. Calcd for C$_{19}$H$_{17}$NO$_3$.0.2H$_2$O: C, 73.39; H, 5.64; N, 4.50. Found: C, 73.36; H, 5.21; N, 4.22.

2-piperidin-1-yl-benzo[h]chromen-4-one
(Compound 295)

Pale brown solid. (0.034 g, 0.12 mmol, 32% yield) mp 205-207° C. $^1$H NMR (200 MHz, d$_6$-DMSO) δ 1.69 (6H, s); 3.56 (4H, s); 5.59 (1H, s); 7.55 (2H, m); 7.83 (2H, q); 8.21 (1H, d); 8.24 (1H, m). EIMS m/z=279 (M$^+$), 224, 170, 127, 114, 87. Anal. Calcd for C$_{18}$H$_{17}$NO$_2$. 0.1 CH$_2$Cl$_2$: C, 75.53; H, 6.02; N, 4.87. Found: C, 75.81; H, 5.80; N, 4.82.

2-(Thiomorpholin-4-yl)-benzo[h]chromen-4-one
(Compound 296)

Orange solid. (0.39 g, 1.31 mmol, 46% yield), mp 171-173° C. FT-IR 3087, 2963, 1642, 1604, 1562 cm$^{-1}$. $^1$H NMR (200 MHz, d$_6$-DMSO) δ 2.86 (4H, m); 4.06 (4H, m); 5.80 (1H, s); 7.84 (2H, m); 8.00 (2H, q); 8.12 (1H, m); 8.46 (1H, m); EIMS m/z=297 (M$^+$), 224, 170, 127, 114, 87. Anal. Calcd for C$_{17}$H$_{15}$NO$_2$S 0.3 CH$_3$COOC$_2$H$_5$: C, 67.39; H, 5.45; N, 4.29. Found: C, 67.22; H, 5.14; N, 4.14.

Compound 297

Synthesis of Starting Material 5,6,7,8-Tetrahydro-1-hydroxy-2-naphthoic acid

A mixture of 5,6,7,8-tetrahydro-1-naphthol (7.42 g, 50 mmol) and potassium carbonate (25.5 g, 185 mmol) were placed in a glass tube inside a stainless steel pressure reactor. The reactor was charged with CO$_2$ at 40 bar and then heated to 145° C. The pressure rose to 60 bar and then slowly dropped to 20 bar over the 3 day reaction period. The bomb was cooled and the solid product was taken up in water (~500 ml) and acetone (~500 ml). The mixture was evaporated in vacuo to remove the acetone and then washed with DCM (3×150 ml). The aqueous was acidified with 2M hydrochloric acid to give a white suspension. This was extracted with DCM (4×250 ml), which was then dried over sodium sulphate and evaporated in vacuo to give the crude product. This was recrystallised from aqueous ethanol and dried under high vacuum to provide 8.64 g (45 mmol, 90% yield) of the title compound as a pale brown powder. $^1$H NMR (200 MHz., d$^6$-DMSO) δ 1.81 (4H, m); 2.67 (2H, m); 2.81 (2H, m); 6.73 (1H, d); 7.61 (1H, d); 11.78 (1H, bs). EIMS m/z=192 (M+); 174; 146

7,8,9,10-Tetrahydrobenzo[h]-2-(morpholin-4-yl)-chromen-4-one (Compound 297)

Off-white powder: mp 220-222° C. IR (KBr): 1628; 1592; 1561; 1246; 1116; 790 cm$^{-1}$. $^1$H NMR (200 MHz., d$_6$-DMSO) δ 1.87 (4H, m); 2.90 (4H, m); 3.59 (4H, m); 3.82 (4H, m); 5.56 (1H, s); 7.17 (1H, d); 7.72 (1H, d). EIMS m/z=285 (M+); 270; 228; 200; 175; 146. Anal. Calcd for C$_{17}$H$_{19}$NO$_3$: C, 71.56; H, 6.71; N, 4.91. Found: C, 71.49; H, 6.76; N, 4.83.

Compound 298

Alternative Step (a) for this Compound

Methyl 5-bromo-2-hydroxybenzoate

Prepared from 5-bromo-2-hydroxybenzoic acid (3.26 g, 15 mmol) according to general method A, affording 2.45 g (10.6 mmol, 71% yield) as an off-white powder. $^1$H NMR (200 MHz., CDCl$_3$) δ 3.89 (3H, s, CH$_3$); 6.81 (1H, d, J=8.8 Hz., 3-H); 7.46 (1H, dd, J=8.8, 2.5 Hz., 4-H); 7.89 (1H, d, J=2.5 Hz., 6-H); 10.62 (1H, s, OH).

Methyl 2-hydroxy-5-phenylbenzoate

A solution of phenylboronic acid (1.34 g, 11.0 mmol) and methyl 5-bromo-2-hydroxybenzoate (2.42 g, 10.5 mmol) in acetone (25 ml) was treated with water (30 ml), followed by potassium carbonate (3.77 g, 27.3 mmol) and finally, palladium (II) acetate (0.16 g, 0.7 mmol). Upon addition of the palladium, the reaction mixture rapidly darkened. The reaction mixture was heated to reflux and stirred for 6 h. After cooling the dark mixture, ether (40 ml) was added, stirred vigorously and decanted. This extraction process was repeated an additional four times. The ethereal extracts were dried over sodium sulphate and evaporated in vacuo to give a yellow liquid. The crude product was dissolved in petrol and loaded onto a silica flash column. The column was eluted with petrol, followed by 5-10% ethyl acetate in petrol. The second product collected was evaporated in vacuo and then recrystallised from petrol to provide a white crystalline solid (1.35 g, 5.90 mmol, 56% yield). $^1$H NMR (200 MHz., d$^6$-DMSO) δ 4.05 (3H, s); 7.20 (1H, m); 7.50-7.58 (3H, m); 7.74 (2H, m); 7.97 (1H, m); 8.13 (1H, m); 10.67 (1H, s, OH).

2-(Morpholin-4-yl)-6-phenylchromen-4-one (Compound 298)

Off-white powder: mp 218-220° C. $^1$H NMR (200 MHz., d$^6$-DMSO) δ 3.66 (4H, m); 3.85 (4H, m); 5.68 (1H, s, 3-H); 7.57 (3H, m); 7.72 (1H, d, 8-H); 7.83 (2H, m); 8.08 (1H, dd, 7-H); 8.24 (1H, d, 5-H). EIMS m/z=307 (M+); 196; 168. IR (KBr): 1611; 1558; 1428; 1245; 1119; 768 cm$^{-1}$. Anal. Calcd. for C$_{19}$H$_{17}$NO$_3$.0.2H$_2$O: C, 73.39; H, 5.64; N, 4.50. Found: C, 73.41; H, 5.45; N, 4.28.

7-(2,6-Dichlorobenzyloxy)-2-(morpholin-4-yl)-chromen-4-one (Compound 299)

Off-white powder. $^1$H NMR (200 Mhz, d$_6$-DMSO) δ 3.62 (4H, m); 3.82 (4H, m); 5.44 (2H, s); 5.55 (1H, s); 7.13 (1H, dd, J=2.4, 8.8 Hz.); 7.43 (1H, d, J=2.4 Hz.); 7.57-7.73 (3H, m); 7.94 (1H, d, J=8.8 Hz.)

2-morpholin-4-yl-chromen-4-one (Compound 300)

White powder. mp 143° C. IR: (KBr)/(cm$^{-1}$): 3067, 3035, 2960, 1620, 1555, 1410, 1252, 1122, 1068, 770. $^1$H NMR: δ(d$_6$-DMSO): 3.19 (4H, t, J=4.5, CH$_2$N); 3.87 (4H, t, J=4.5, CH$_2$O); 5.67 (1H, s, H-4); 7.26 (2H, m, Ar—H); 7.49 (2H, m, Ar—H). HRMS m/z (EI): 231.0890 (M$^+$, Calcd 231.0895 for C$_{13}$H$_{13}$NO$_3$), 214, 202, 172, 145, 118, 101, 89, 77. Anal. Calcd for C$_{13}$H$_{13}$NO$_3$: C, 67.52; H, 5.67; N, 6.06. Found: C, 67.28; H, 5.43; N, 5.81.

2-morpholin-benzo<g>-chromen-4-one (Compound 301)

Pale brown solid. mp 219° C. IR (KBr)/(cm$^{-1}$): 3048, 2906, 2869, 1598, 1569, 1464, 1424, 1356, 1252, 1118, 791.

¹H NMR: δ(d₆-DMSO): 3.60 (4H, t, J=4.5, CH₂N); 3.88 (4H, t, J=4.5, CH₂O); 5.54 (1H, s, H-4); 7.55 (1H, m, Ar—H); 7.74 (1H, m, Ar—H); 8.04 (1H, m, Ar—H); 8.74 (1H, m, Ar—H). HRMS m/z (EI): 281.1038 (M⁺, Calcd 281.1052 for C₁₇H₁₅NO₃), 224, 196, 170, 142, 127, 114, 98. Anal. Calcd for C₁₇H₁₅NO₃.0.25H₂O: C, 71.43; H, 5.25; N, 4.90. Found: C, 71.37; H, 5.04; N, 4.85.

8-Methyl-2-morpholin-4-yl-chromen-4-one (Compound 302)

Orange solid. mp 148° C. IR: (KBr)/(cm⁻¹): 3069, 2963, 2860, 1629, 1570, 1411, 1251, 1118, 778. ¹H NMR: δ(d₆-DMSO): 2.51 (3H, s, Me); 3.60 (4H, t, J=5, CH₂N); 3.85 (4H, t, J=5, CH₂O); 5.62 (1H, s, H-4); 7.37 (1H, m, Ar—H); 7.61 (1H, m, Ar—H); 7.86 (1H, m, Ar—H). HRMS m/z (EI): 245.1052 (M⁺, Calcd 245.1052 for C₁₄H₁₅NO₃), 230, 188, 160, 134, 114, 106, 86, 77. Anal. Calcd for C₁₄H₁₅NO₃.0.2H₂O: C, 67.55; H, 6.03; N, 5.63. Found: C, 67.65; H, 6.06; N, 5.16.

8-Methoxy-2-morpholin-4-yl-chromen-4-one (Compound 303)

Yellow solid. mp 165° C. IR: (KBr)/(cm⁻¹): 3085, 2949, 2857, 1638, 1599, 1571, 1411, 1245, 1116, 773. ¹H NMR: δ (d₆-DMSO): 3.51 (4H, t, J=4.5, CH₂N); 3.81 (4H, t, J=4.5, CH₂O); 3.91 (3H, s, MeO); 5.48 (1H, s, H-4); 7.06 (1H, m, Ar—H); 7.22 (1H, m, Ar—H); 7.6 (1H, m, Ar—H). HRMS m/z (EI): 261.0991 (M⁺, Calcd 261.1001 for C₁₄H₁₅NO₄), 204, 151, 122, 114, 107, 92.

7-Methoxy-2-(morpholin-4-yl)-chromen-4-one (Compound 304)

Off-white powder: mp 174-175° C. ¹H NMR (200 MHz., d⁶-DMSO) δ 3.57 (4H, m); 3.81 (4H, m); 3.94 (3H, s); 5.50 (1H, s); 7.03 (1H, dd); 7.16 (1H, dd); 7.90 (1H, d). ¹³C NMR (50 MHz., d⁶-DMSO) δ 56.17; 65.66; 86.07; 100.65; 113.36; 116.39; 126.15; 155.15; 162.63; 162.95; 175.39 ESMS m/z=261 (M+), 204

Compound 305 and 306

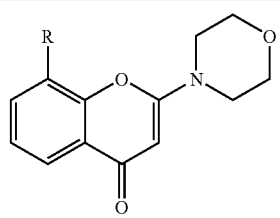

| Compound | Substituent | Mw |
|---|---|---|
| 305 | (OSO₂CF₃) | 380.16 |

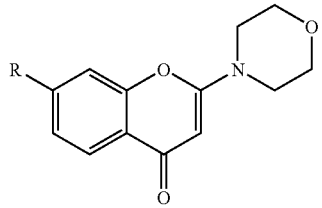

| Compound | Substituent | Mw |
|---|---|---|
| 306 | (OSO₂CF₃) | 380.21 |

Synthesis of Starting Material

Methyl 2,3-dihydroxybenzoate

Prepared from 2,3-Dihydroxybenzoic acid (1 g, 7.25 mmol), affording a pale brown solid (0.29 g, 1.73 mmol, 23% yield); mp 81.1-81.9° C.; Rf=0.78 (solvent 95% DCM: 5% methanol); ¹H NMR (300 MHz, CDCl₃) δ 7.35 (1H, d, Ar4), 7.15 (1H, d, Ar6), 6.85 (1H, dd, Ar5), 4.00 (3H, d, CH₃).

Preparation of 2-Hydroxy-3-trifluoromethanesulfonyloxy-benzoic acid methyl ester To a sample of methyl 2,3-dihydroxybenzoate (4.00 g, 23.80 mmol) dissolved in dichloromethane (25 ml), pyridine (0.96 ml, 11.9 mmol) was added and dimethylaminopyridine (0.07 g, 0.58 mmol). The mixture was cooled to 0° C. and trifluoromethane sulfonic anhydride (4.40 ml, 26.18 mmol) was added dropwise by syringe. The reaction mixture was warmed to room temperature and left to stir for 60 h. The organic layer washed with 1M HCl (40 ml), dried (Na₂SO₄) and concentrated to dryness in vacuo. The solid was recrystallized from ethyl acetate to yield white crystals. (2.62 g, 8.73 mmol, 37% yield), mp 91.8-92.3° C.; Rf=0.89 (solvent; 95% DCM: 5% methanol); ES+(m/e) 300.00 (M+1); HPLC retention time=7.47 min (long); ¹H NMR (300 MHz, CDCl₃) δ7.85 (1H, d, Ar4), 7.45 (1H, d, Ar6), 6.95 (1H, t, Ar5), 4.00 (3H, d, CH₃)

Preparation of 2-Hydroxy-4-trifluoromethanesulfonyloxy-benzoic acid methyl ester Prepared as for 2-Hydroxy-3-trifluoromethanesulfonyloxy-benzoic acid methyl ester, from methyl 2,4-dihydroxybenzoate affording a white crystalline solid. ES+(m/e) 300.00 (M+1)

(b) Trifluoro-methanesulfonic acid 2-hydroxy-3-(3-morpholin-4-yl-3-oxo-propionyl)-phenyl ester Prepared from 2-Hydroxy-3-trifluoromethanesulfonyloxy-benzoic acid methyl ester (2.10 g, 7 mmol), affording a pale brown solid (1.10 g, 2.54 mmol, 36% yield). ES+(m/e)

398.25; ¹H NMR (300 MHz, CDCl₃) δ7.85 (1H, d, Ar4), 7.35 (1H, d, Ar6), 6.90 (1H, dd, Ar5), 4.05 (2H, s, CH₂O), 3.50 (8H, m, CH₂N, CH₂O).

(c) Trifluoro-methanesulfonic acid 2-morpholin-4-yl-4-oxo-4H-chromen-8-yl ester (Compound 305)

Prepared from Trifluoromethanesulfonic acid 2-hydroxy-3-(3-morpholin-4-yl-3-oxo-propionyl)-phenyl ester (0.91 g, 2.3 mmol), affording a white solid (0.25 g, 0.662 mmol, 28.79% yield) mp 177.8-178.9° C. Rf=0.30 (5% MeOH: 95% DCM). ES+(m/e) 380.16 (M+1). ¹H NMR (300 MHz, CDCl₃) δ3.50 (4H, m, CH₂N); 3.78 (4H, m, CH₂O); 5.46 (1H, s, Ar3); 7.40 (2H, m, Ar6, 7); 8.09 (1H, m, Ar5).

Trifluoro-methanesulfonic acid 2-morpholin-4-yl-4-oxo-4H-chromen-7-yl ester (Compound 306)

Prepared from Trifluoromethanesulfonic acid 3-hydroxy-4-(3-morpholin-4-yl-3-oxo-propionyl)-phenyl ester (1.50 g, 3.80 mmol), affording a white solid (0.69 g, 1.83 mmol, 48% yield) mp 143-145° C.; ES+(m/e)=380.21 (M+1); ¹H NMR (300 MHz, CDCl₃) δ3.45 (4H, m, CH₂N); 63.77 (4H, m, CH₂O); 65.36 (1H, s, CH); δ7.32 (2H, m); δ8.01 (1H, m).

Further Derivatisation 7-Hydroxy-2-(morpholin-4-yl)-chromen-4-one (Compound 307)

To a mixture of 7-(2,6-dichlorobenzyloxy)-2-(morpholin-4-yl)-chromen-4-one (6.60 g, 16.2 mmol) (299) and 10% Pd/C (150 mg) was added methanol (150 ml), under nitrogen. The suspension was stirred under an atmosphere of hydrogen for 40 h. The catalyst was removed by filtration through Celite, washing with methanol. The solvent was removed by evaporation in vacuo to provide an off-white solid. This was treated with fresh catalyst, re-suspended in methanol under nitrogen and stirred under an atmosphere of hydrogen for a further 72 h. The catalyst was removed by filtration through Celite, washing with methanol. The filtrate was evaporated in vacuo and the crude product re-crystallised from methanol to provide 2.26 g (9.1 mmol, 57%) of the desired compound as a white solid. mp>250° C. (decomp). ¹H NMR (200 Mhz, d₆-DMSO) δ 3.78 (4H, m); 3.86 (4H, m); 6.15 (1H, s); 7.05-7.13 (2H, m); 7.93 (1H, d); 11.3 (1H, bs). ESMS m/z=247 (M+), 190, 105.

Route 7a

Examples of compounds synthesised using synthetic route 7a are listed in the following table. All examples of compounds synthesised by this route were isolated with a purity of at least 99%.

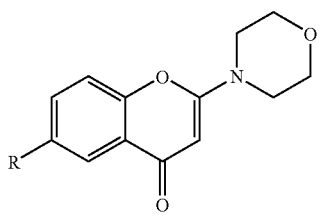

| Compound | Substituent | Mw LC-MS |
|---|---|---|
| 308 | •—Br | 310.24 |

| Compound | Structure | Mw LC-MS |
|---|---|---|
| 309 | 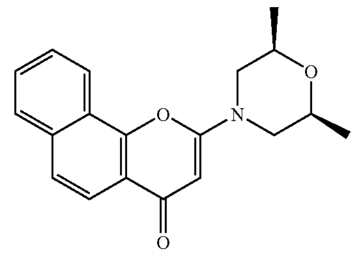 | |
| 310 | | |

(a) 4-Hydroxy-benzo[f]-chromen-2-thione

Prepared from 2-hydroxy-1-acetonaphthone (3.72 g, 20.0 mmol) affording 1.96 g (8.6 mmol, 13% yield) as a yellow solid. ¹H NMR (200 MHz., d⁶-DMSO) δ 6.97 (1H, s); 7.73-7.90 (3H, m); 8.20 (1H, d); 8.40 (1H, d); 9.43 (1H, d). EIMS m/z=228 (M+); 209; 170; 142; 69.

4-Hydroxy-benzo-[h]-chromen-2-thione

Prepared from 1-hydroxy-2-acetonaphthone (3.72 g, 20 mmol) affording 1.09 g (5.32 mmol, 29% yield) as orange crystals. mp 221-223° C. ¹H NMR (200 MHz, d⁶-DMSO) δ 4.21 (1H, bs); 6.89 (1H, s); 7.91 (2H, m); 7.99 (2H, m); 8.18 (1H, m); 8.56 (1H, m)

6-Bromo-4-hydroxy-chromene-2-thione

Prepared from 5-Bromo-2-hydroxyacetophenone (4.30 g, 20 mmol), affording a yellow powder (1.85 g 7.20 mmol, 36%); ES+(m/e)=258 (M⁺+1)

(b) 2-(Ethylthio)-benzo[f]-chromen-4-one

Yellow crystalline solid: mp 126-127° C. IR (KBr) 1632; 1437; 815 cm⁻¹. ¹H NMR (200 MHz., d⁶-DMSO) δ 1.48 (3H, t, CH₂CH₃); 3.32 (2H, q, CH₂CH₃); 6.62 (1H, s, 3-H); 7.73-7.91 (3H, m); 8.19 (1H, d); 8.41 (1H, d); 10.01 (1H, d). EIMS m/z=256 (M+); 170; 142. Anal. Calcd for C₁₅H₁₂O₂S.0.1H₂O: C, 69.80; H, 4.76. Found: C, 69.77; H, 4.53.

2-Ethylsulphanyl-benzo-[h]-chromen-4-one

Pale brown crystals (0.42 g, 2.85 mmol, 62% yield). mp 116-117° C. ¹H NMR (200 Mhz, d⁶-DMSO) δ1.45 (3H, t, J=7.4 Hz); 3.13 (2H, q, J=7.4 Hz); 6.36 (1H, s); 7.65 (4H, m); 8.06 (1H, m); 8.41 (1H, m)

6-Bromo-2-ethylsulfanyl-chromen-4-one

Prepared from 6-Bromo-4-hydroxy-chromene-2-thione (0.57 g, 2.21 mmol), ethyl iodide (0.65 ml, 8 mmol) and potassium carbonate (0.35 g, 2.5 mmol) affording a yellow solid (0.40 g, 1.40 mmol, 63%); ES+(m/e)=287 (M⁺+1)

(c) 2-(Morpholin-4-yl)-benzo[f]-chromen-4-one (Compound 310)

Prepared from 2-(ethylthio)-benzo[f]-chromen-4-one (0.512 g, 2.0 mmol). Recrystallisation from methanol provided 0.238 g (0.84 mmol, 42% yield) of an off-white crystalline solid: mp 213-214° C. IR (KBr): 2956; 2861; 1639;

1601; 1590; 1567; 1512; 1420; 1252; 1246; 1115; 821 cm$^{-1}$. $^1$H NMR (200 MHz., d$^6$-DMSO) δ 3.64 (4H, m); 3.86 (4H, m); 5.78 (1H, s, chromenone 3-H); 7.67-7.84 (3H, m); 8.14 (1H, d); 8.32 (1H, d); 10.16 (1H, d). EIMS m/z=281 (M+); 253; 224; 196; 170.

6-Bromo-2-morpholin-4-yl-chromen-4-one (Compound 308)

Prepared from 6-Bromo-2-ethylsulfanyl-chromen-4-one (0.375 g, 1.35 mmol) and morpholine (0.54 ml, 6.25 mmol), affording a pale yellow solid. (0.0354 g, 1.14 mmol, 84%); m.p. 147-149° C.; ES+(m/e)=310.24 (M$^+$+1); (200 MHz, CDCl$_3$) δ3.44 (4H, m); 3.77 (4H, m); 5.42 (1H, s); 7.11 (1H, d); 7.57 (1H, dd); 8.20 (1H, d)

2-(2,6-cis-dimethyl-morpholin-4-yl)-benzo[h]chromen-4-one (Compound 309)

Off white solid (0.174 g, 0.56 mmol, 56%): m.p. 211-212.5° C.; ES+(m/e) 310 (M+1); R$_f$=0.30 (5% Methanol/DCM); $^1$H NMR (200 MHz, CDCl$_3$) δ1.27 (6H, d); 2.74 (2H, t); 3.72 (2H, m); 3.86 (2H, d); 5.56 (1H, s); 7.58 (2H, m); 7.67 (1H, d); 7.86 (1H, m); 8.08 (1H, d); 8.19 (1H, m)

(d) 2-piperazin-1-yl-benzo[h]chromen-4-one (Compound 311)

Prepared from 2-ethylsulphanyl-benzo[h]chromen-4-one (0.384 g, 1.5 mmol) and piperazine (1.29 g, 15 mmol). Recrystallisation from ethyl acetate provided an off white solid. (0.121 g, 0.43 mmol, 28% yield) mp 208-209° C. UV λ$_{max}$=317.0, 273.0, 255.0, 216.5 nm (Methanol). $^1$H NMR (200 MHz, CDCl$_3$) δ 3.01 (4H, m); 3.55 (4H, m); 5.57 (1H, s); 7.56 (2H, m); 7.66 (1H, d); 7.85 (1H, m); 8.08 (1H, d); 8.21 (1H, m). EIMS m/z (EI$^+$): 280 (M$^+$), 261, 238, 225, 170, 139. Anal. Calcd for C$_{17}$H$_{16}$N$_2$O$_2$.0.3H$_2$O: C, 71.46; H, 5.81; N, 9.80. Found: C, 71.88; H, 5.91; N, 9.33.

2-(Pyrrolidinyl)-benzo[h]chromen-4-one (Compound 312)

Off white solid. (0.104 g, 0.39 mmol, 26% yield) mp 234-236° C. $^1$H NMR (200 MHz, CDCl$_3$) δ 2.05 (4H, m); 3.55 (4H, m); 5.36 (1H, s); 7.55 (2H, m); 7.65 (1H, d); 7.83 (1H, m); 8.10 (1H, d); 8.19 (1H, m). EIMS m/z (EI$^+$): 265 (M$^+$), 210, 196, 170, 114, 95. Anal. Calcd for C$_{17}$H$_{15}$NO$_2$.0.28CH$_2$Cl$_2$: C, 71.70; H, 5.42; N, 4.84. Found: C, 71.43; H, 5.76; N, 4.75.

2-(3-Hydroxymethyl-piperidin-1-yl)-benzo[h]chromen-4-one (Compound 313)

Off white solid. (0.131 g, 0.42 mmol, 43% yield) mp 209-210° C. UV λ$_{max}$=319.0, 284.0, 274.0, 254.0, 217.0 nm (Methanol). FT-IR 3300, 2924, 2854, 1640, 1609, 1559, 1439 cm$^-$1. $^1$H NMR (200 MHz, CDCl$_3$) δ 1.30 (1H, m); 1.79 (4H, m); 3.14 (2H, m); 3.51 (1H, m); 3.65 (1H, m); 3.98 (1H, m); 4.14 (1H, m); 5.64 (1H, s); 7.49 (2H, m); 7.60 (1H, d); 7.77 (1H, m); 8.02 (1H, d); 8.17 (1H, m). EIMS m/z (EI$^+$): 309 (M$^+$), 292, 278, 224, 196, 170, 138, 82, 55. Anal. Calcd for C$_{19}$H$_{19}$NO$_3$.0.1H$_2$O: C, 73.34; H, 6.32; N, 4.50. Found: C, 73.28; H, 6.19; N, 4.13

2-(4-Methyl-piperazin-1-yl)-benzo[h]chromen-4-one (Compound 314)

White solid. (0.194 g, 0.66 mmol, 67% yield) mp 184-185° C. UV λ$_{max}$=316.0, 272.0, 254.5, 218.0 nm (Methanol). $^1$H NMR (200 MHz, CDCl$_3$) δ 2.32 (3H, s); 2.54 (4H, t); 3.60 (4H, t); 5.59 (1H, s); 7.56 (2H, m); 7.67 (1H, d); 7.83 (1H, m); 8.08 (1H, d); 8.21 (1H, m). EIMS m/z (EI$^+$): 294 (M$^+$), 237, 224, 210, 196, 170, 139, 123, 70. Anal. Calcd for C$_{18}$H$_{18}$N$_2$O$_2$.1H$_2$O. 0.1CH$_3$OH: C, 68.85; H, 6.52; N, 8.88. Found: C, 68.63; H, 6.45; N, 8.57.

2-(3-Hydroxy-pyrollidin-1-yl)-benzo[h]chromen-4-one (Compound 315)

White solid. (0.201 g, 0.72 mmol, 72% yield) mp 256-257° C. UV λ$_{max}$=318, 283.5, 273.0, 253.0, 215.0 nm (Methanol). $^1$H NMR (200 MHz, DMSO) 62.18 (2H, m); 3.45 (4H, m); 4.58 (1H, m); 5.32 (1H, m) 5.41 (1H, s); 7.83 (2H, m); 7.93 (1H, d); 8.05 (1H, d); 8.16 (1H, m); 8.45 (1H, m). EIMS m/z (EI$^+$): 281 (M$^+$), 264, 236, 224, 210, 196, 181, 170, 139, 114, 67. Anal. Calcd for C$_{17}$H$_{15}$NO$_3$.0.2H$_2$O: C, 71.67; H, 5.45; N, 4.92 Found: C, 71.65; H, 5.34; N, 4.49

2-[(Tetrahydrofuran-2-ylmethyl)-amino]-benzo[h]chromen-4-one (Compound 316)

Off white crystalline solid. (0.107 g, 0.36 mmol, 37% yield) mp 139-140° C. UV %=314.0, 280.5, 270.5, 252.5, 216.5 nm (Methanol). $^1$H NMR (200 MHz, CDCl$_3$) δ 1.65 (1H, m); 1.91 (3H, m); 3.14 (2H, m); 3.21 (1H, m); 3.38 (1H, M); 3.81 (2H, m); 4.11 (1H, m); 5.40 (1H, t); 5.47 (1H, s); 7.54 (2H, m); 7.65 (1H, d); 7.82 (1H, m); 8.08 (1H, d); 8.24 (1H, m). EIMS m/z (EI$^+$): 295 (M$^+$), 272, 225, 211, 196, 186, 171, 158, 84, 71. Anal. Calcd for C$_{16}$H$_{17}$NO$_3$.0.3H$_2$O: C, 71.85; H, 5.90; N, 4.66. Found: C, 72.12; H, 5.80; N, 4.33

2-(2-Methyl-morpholin-4-yl)-benzo[h]chromen-4-one (Compound 317)

Synthesis of 2-Methyl morpholine

Ref: Bettoni et al. Tetrahedron, 1980, 36, 409-415

(i) 1-(2-Hydroxy-ethylamino)-propan-2-ol

Propylene oxide (2.32 g, 0.04 mmol) was added dropwise to a solution of ethanolamine (10.0 g, 0.16 mmol) in water (50 ml) at 0° C., and the solution stirred at room temperature for 5 h. Water was removed by evaporation in vaccuo resulting in a colourless oil which was then distilled under reduced pressure to yield the title compound as a colourless oil. (3.61 g, 30.34 mmol, 76%) $^1$H NMR (200 MHz, CDCl$_3$) δ1.15 (3H, d); 2.46 (2H, m); 2.71 (2H, t,); 3.62 (2H, t); 3.90 (1H, m,); 4.10 (3H, s.).

(ii) Toluene-4-sulfonic acid 2-[(2-hydroxy-propyl)-(toluene-4-sulfonyl)-amino]-ethyl ester Tosyl chloride (11.60 g, 60.80 mmol) was added in small portions to a stirred solution of 1-(2-Hydroxy-ethylamino)-propan-2-ol (3.60 g, 30.25 mmol) in anhydrous pyridine at 0° C. The reaction was stirred at room temperature for 24 h and then poured onto ice-water (200 ml). The mixture was extracted into DCM (100 ml). The organic extract washed with 2N HCl, water, and was evaporated in vaccuo to give a brown residue which was used without further purification.

(iii) 2-Methyl-4-(toluene-4-sulfonyl)-morpholine

Sodium hydroxide (0.91 g, 0.02 mol) suspended in methanol (15 ml) was added to a stirred solution of Toluene-4-sulfonic acid 2-[(2-hydroxy-propyl)-(toluene-4-sulfonyl)-amino]-ethyl ester (9.69 g, 0.02 mol) in DCM (15 ml). After 1 h, water (50 ml) was added to the solution. The organic layer was collected, dried over sodium sulphate and evaporated in vaccuo to yield a green oily residue. This was purified by chromatographic separation (20% Ethyl acetate:petrol) to yield the title compound as a white solid. (1.70 g, 6.66 mmol, 33%).

(iv) 2-Methyl Morpholine

2-Methyl-4-(toluene-4-sulfonyl)-morpholine (1.65 g, 6.51 mmol) was dissolved in warm pentanol (30 ml). The solution was cooled to room temperature and sodium (1.49 g, 65 mmol) was added in small portions. The reaction mixture was stirred vigorously and heated to reflux for 3 h. Upon cooling, water (50 ml) was added. The two layers were separated, the aqueous layer was extracted with ether, and this in turn was extracted with 2N HCl. The alcoholic solution was extracted with 2N HCl. The combined acidic solutions were then made alkaline by addition of sodium hydrogen carbonate, and continuously extracted with ether. The ether was evaporated in vaccuo to yield the title compound as a colourless oil. (0.517 g, 5.11 mmol, 79%) $^1$H NMR (200 MHz, CDCl$_3$) δ1.15 (3H, d); 2.74 (5H, m); 3.81 (4H, m).

Final Compound (Compound 317)

Off white crystalline solid. (0.085 g, 0.29 mmol, 20% yield). mp 181-183° C. UV λ=214.4, 217.4 (λ$_{max}$), 255.0, 272.8, 281.8, 300.8, 315.2 nm (Methanol). FT-IR (cm$^{-1}$)= 3174, 2976, 2860, 1614, 1557, 1388, 1245, 1086, 795, 747. $^1$H NMR (200 MHz, CDCl$_3$) δ1.25 (3H, d); 2.81 (1H, t); 3.16 (1H, dt); 3.71 (2H, m); 3.83 (2H, t); 4.02 (1H, m); 5.55 (1H, s); 7.55 (2H, m); 7.66 (1H, d); 7.83 (1H, d); 8.06 (1H, d); 8.17 (1H, d). ESMS m/e=296 (M+1). Anal. Calcd. For C$_{18}$H$_{17}$NO$_3$. 0.1H$_2$O: C, 72.76; H, 5.83; N, 4.71. Found: C, 72.74; H, 5.77; N, 4.60.

(f) 2-(4-Hydroxymethyl-piperidin-1-yl)-benzo[h]chromen-4-one (Compound 318)

Prepared from (Benzo-[h]-4-oxo-4H-chromen-2-yl)-thiomethylpolystyrene-divinylbenzene resin and 4-piperidine methanol (0.0027 g, 0.036 mmol). Product obtained=0.0039 g. m/z (ES$^+$): 310 (M+1) 5% Methanol/DCM, R$_f$=0.21

2-[(2-Hydroxy-2-phenyl-ethyl)-methyl-amino]benzo[h]chromen-4-one (Compound 319)

m/z (ES$^+$): 346 (M+1); 5% Methanol/DCM, R$_f$=0.30

2-(3-Diethylamino-propylamino)-benzo[h]chromen-4-one (Compound 320)

m/z (ES$^+$): 325 (M+1); 5% Methanol/DCM, R$_f$=0.19

2-((S)-2-Hydroxymethyl-pyrrolidin-1-yl)-benzo[h]chromen-4-one (Compound 321)

m/z (ES$^+$): 296 (M+1); 5% Methanol/DCM, R$_f$=0.29

2-(3-Methoxy-propylamino)-benzo[h]chromen-4-one (Compound 322)

m/z (ES$^+$): 284 (M+1); 5% Methanol/DCM, R$_f$=0.32

2-(1-Benzyl-piperidin-4-ylamino)-benzo[h]chromen-4-one (Compound 323)

m/z (ES$^+$): 385 (M+1); 5% Methanol/DCM, R$_f$=0.17

2-(Cyclopentylamino)-benzo[h]chromen-4-one (Compound 324)

m/z (ES$^+$): 280 (M+1); 5% Methanol/DCM, R$_f$=0.33

2-(2,2-Dimethoxy-ethylamino)benzo[h]chromen-4-one (Compound 325)

m/z (ES$^+$): 300 (M+1); 5% Methanol/DCM, R$_f$=0.29

2-Butylamino-benzo[h]chromen-4-one (Compound 326)

m/z (ES$^+$): 268 (M+1); 5% Methanol/DCM, R$_f$=0.30

2-(2-Trifluoromethyl-benzylamino)-benzo[h]chromen-4-one (Compound 327)

m/z (ES$^+$): 370 (M+1); 5% Methanol/DCM, R$_f$=0.31

2-(3-Hydroxy-propylamino)-benzo[h]chromen-4-one (Compound 328)

m/z (ES$^+$): 270 (M+1); 5% Methanol/DCM, R$_f$=0.12

2-(2-Hydroxy-2-phenyl-ethylamino)-benzo[h]chromen-4-one (Compound 329)

m/z (ES$^+$): 332 (M+1); 5% Methanol/DCM, R$_f$=0.22

2-(Thiazolidin-3-yl)-benzo[h]chromen-4-one (Compound 330)

m/z (ES$^+$): 284 (M+1); 5% Methanol/DCM, R$_f$=0.35

2-(2-Hydroxy-propylamino)-benzo[h]chromen-4-one (Compound 331)

m/z (ES$^+$): 270 (M+1); 5% Methanol/DCM, R$_f$=0.15

2-[(2-Hydroxy-ethyl)methyl-amino]-benzo[h]chromen-4-one (Compound 332)

m/z (ES$^+$): 270 (M+1); 5% Methanol/DCM, R$_f$=0.19

2-(Ethyl-hyroxymethyl-amino)benzo[h]chromen-4-one (Compound 333)

m/z (ES$^+$): 284 (M+1); 5% Methanol/DCM, R$_f$=0.25

2-(Dibutylamino)-benzo[h]chromen-4-one (Compound 334)

m/z (ES$^+$): 324 (M+1); 5% Methanol/DCM, R$_f$=0.26

2-(2-Methoxy-ethylamino)-benzo[h]chromen-4-one (Compound 335)

m/z (ES$^+$): 270 (M+1); 5% Methanol/DCM, R$_f$=0.10

2-(Isopropylamino)-benzo[h]chromen-4-one (Compound 336)

m/z (ES$^+$): 254 (M+1); 5% Methanol/DCM, R$_f$=0.27

Route 7b

2-Hydroxy-4-(4-methoxybenzyloxy)-acetophenone

A mixture of 2,4-dihydroxyacetophenone (7.30 g, 48 mmol), potassium carbonate (7.30 g, 53 mmol) and sodium iodide (0.75 g, 5.0 mmol) in anhydrous acetonitrile (60 ml) was treated with 4-methoxybenzyl chloride (6.5 ml, 48 mmol). The mixture was heated to 65° C. and stirred for 16 h. The mixture was treated with 1M hydrochloric acid (120 ml) and extracted into ethyl acetate (120 ml). The ethyl acetate extract washed with 1M hydrochloric acid (100 ml) and brine (100 ml), dried over sodium sulphate and evaporated in vacuo. The crude product was stirred vigorously in ether and filtered to provide 6.31 g (23.4 mmol, 49% yield) of the title compound as a beige powder.

(a) 4-Hydroxy-7-(4-methoxybenzyloxy)-chromen-2-thione

Prepared from 2-hydroxy-4-(4-methoxybenzyloxy)-acetophenone (5.44 g, 20 mmol) affording 2.04 g (6.5 mmol, 32% yield) as a yellow powder.

(e) S-(7-(Hydroxy)-4-oxo-4H-chromen-2-yl)-thiomethylpolystyrene-divinylbenzene resin Prepared from Merrifield resin (1% cross-linked, 1.2 mmol/g) (0.70 g, 0.84 mmol) and a solution of 4-hydroxy-7-(4-methoxybenzyloxy)-chromen-2-thione (0.70 g, 2.2 mmol) in DMF (3 ml).

(g, followed by f(i)(ii)) 7-(Benzyloxy)-2-(morpholin-4-yl)-chromen-4-one (Compound 337)

Prepared from S-(7-(Hydroxy)-4-oxo-4H-chromen-2-yl)-thiomethylpolystyrene-divinylbenzene resin (0.030 g) affording 0.0014 g (0.004 mmol) as a crude residue.

7-(4-Cyanobenzyloxy)-2-(morpholin-4-yl)-chromen-4-one (Compound 338)

Estimated 88% pure by LC-MS; ESMS m/z=363 (M+1)$^+$.

Methyl 4-(2-(morpholin-4-yl)-4-oxo-4H-chromen-7-yloxymethyl)-benzoate (Compound 339)

Estimated 74% pure by LC-MS; ESMS m/z=396 (M+1)$^+$.

Methyl 3-(2-(morpholin-4-yl)-4-oxo-4H-chromen-7-yloxymethyl)-benzoate (Compound 340)

Estimated 82% pure by LC-MS; ESMS m/z=396 (M+1)$^+$.

7-(3-Chlorobenzyloxy)-2-(morpholin-4-yl)-chromen-4-one (Compound 341)

Estimated 90% pure by LC-MS; ESMS m/z=374, 372 (M+1)$^+$.

7-(3-Methylbenzyloxy)-2-(morpholin-4-yl)-chromen-4-one (Compound 342)

Estimated 86% pure by LC-MS; ESMS m/z=352 (M+1)$^+$.
Examples of compounds synthesised using a variant of route 7b in which a 2,5-dihydroxyacetophenone starting material was used in place of 2,4-dihydroxyacetophenone include the following:

6-Hydroxy-2-(morpholin-4-yl)-chromen-4-one (Compound 343)

S-(6-(Hydroxy)-4-oxo-4H-chromen-2-yl)-thiomethylpolystyrene-divinylbenzene resin (0.030 g, <0.036 mmol) was swelled in DCM (2 ml). After shaking for 10 minutes the mixture was treated with m-chloroperbenzoic acid (0.2 g, 1.1 mmol). The mixture was shaken at room temperature for 3 h and then filtered. The resin washed in order with DCM, methanol, DCM and re-suspended in DCM (2 ml). After shaking for 15 minutes the mixture was treated with a solution of morpholine (0.005 ml, 0.05 mmol) in DCM (2 ml). The mixture was shaken at room temperature for 16 h and filtered, washing the resin with DCM and methanol. The filtrate was evaporated in vacuo to provide the crude title compound. The product was submitted for analysis for LC-MS without further purification. Estimated >95% pure by LC-MS; ESMS m/z=248 (M+1)$^+$.

((g) followed by (f) (i) (ii)) 6-(4-Cyanobenzyloxy)-2-(morpholin-4-yl)-chromen-4-one (Compound 344)

Prepared from S-(6-(Hydroxy)-4-oxo-4H-chromen-2-yl)-thiomethylpolystyrene-divinylbenzene resin (0.030 g) affording a crude residue. Estimated 80% pure by LC-MS; ESMS m/z=363 (M+1)$^+$.

N-[3-(2-(morpholin-4-yl)-4-oxo-4H-chromen-6-yloxy)-propyl]-phthalimide (Compound 345)

Estimated 66% pure by LC-MS; ESMS m/z=435 (M+1)$^+$.

Route 7b(i)

Examples of compounds formed using synthetic route 7b(i) are listed in the following tables.

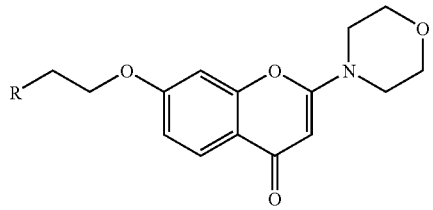

| Compound | R | R Substituent | Mw LC-MS |
|---|---|---|---|
| 346 | Phenyl | 4-Br | 432 |
| 347 | Phenyl | 4-t-Bu | 394 |
| 348 | Phenyl | 4-OMe | 382 |
| 349 | Phenyl | — | 352 |
| 350 | Pyridin-4-yl | N—O$^-$ | 369 |
| 351 | Pyridin-2-yl | N—O$^-$ | 355 |

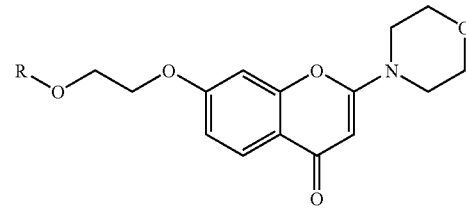

| Compound | R | R Substituent | Mw LC-MS |
|---|---|---|---|
| 352 | Phenyl | 2-Cl | 404 |
| 353 | Phenyl | 4-Cl | 404 |
| 354 | Napth-2-yl | — | 418 |
| 355 | Phenyl | — | 368 |
| 356 | Ethyl | — | 320 |

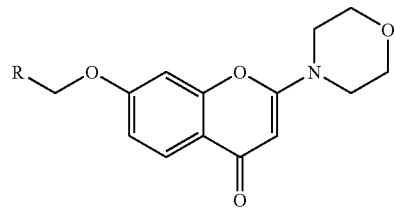

| Compound | R | R Substituent | Mw LC-MS |
|---|---|---|---|
| 357 | Phenyl | 3-OMe | 368 |
| 358 | Phenyl | 3-N(=O)O⁻ | 383 |
| 359 | Phenyl | 3-F | 356 |
| 360 | Phenyl | 3,4-di-F | 374 |
| 361 | Phenyl | 4-Me | 352 |
| 362 | Phenyl | 4-t-Bu | 394 |
| 363 | Phenyl | 3-Br | 417 |
| 364 | Pyridin-3-yl | N—O⁻ | 355 |
| 365 | Pyridin-4-yl | N—O⁻ | 355 |

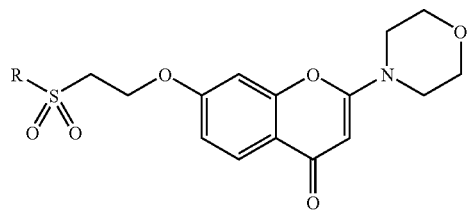

| Compound | R | R Substituent | Mw LC-MS |
|---|---|---|---|
| 366 | Phenyl | — | 416 |
| 367 | Ethyl | — | 368 |
| 368 | Methyl | Phenyl | 430 |

Route 7c

Examples of compounds formed using synthetic route 7c are listed in the tables below.

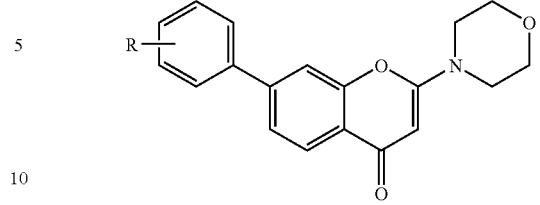

| Compound | Substituent position | Substituent | Mw LC-MS |
|---|---|---|---|
| 369 | 2 | *-O-CH₂-phenyl | 414 |
| 370 | 2 | phenyl | 384 |
| 371 | 4 | *-O-CF₃ | 392 |
| 372 | 3 | phenyl | 384 |
| 373 | 2 | *-CH₂-OH | 338 |
| 374 | 2 | *-NH-C(=O)-CH₃ | 365 |
| 375 | 3 | *-CH₂-phthalimide | 467 |
| 376 | — | benzothiophen-3-yl | 364 |
| 377 | — | thiophen-2-yl | 314 |

-continued

[Structure: 7-R-2-morpholino-chromen-4-one]

| Compound | Substituent | Mw LC-MS |
|---|---|---|
| 378 | 4-fluoro styryl | 352 |
| 379 | thianthrenyl | 446 |

-continued

[Structure: 8-(R-phenyl)-2-morpholino-chromen-4-one]

| Compound | Substituent position | Substituent | Mw LC-MS |
|---|---|---|---|
| 380 | 4 | *-C(O)O-CH2-C6H5 | 442 |
| 381 | 3 | *-O-CH2-C6H5 | 414 |
| 382 | 4 | *-O-CH2-C6H5 | 414 |
| 383 | 4 | *—C≡N | 333 |
| 384 | 4 | *-C(O)CH3 | 350 |
| 385 | 4 | *-OCH3 | 338 |
| 386 | 2 | *-C6H5 | 384 |
| 387 | 4 | *-OCF3 | 392 |
| 388 | 3 | *-OCF3 | 392 |
| 389 | 3 | *-C6H5 | 384 |
| 390 | 3 | *-C(O)OEt | 380 |
| 391 | 4 | *—Cl | 342 |
| 392 | 2 | *-CH2OH | 338 |
| 393 | 3 | *-CH2OH | 338 |
| 394 | 4 | *-CH2OH | 338 |
| 395 | 3 | *—OH | 324 |
| 396 | 4 | *—OH | 324 |
| 397 | 4 | *-NHC(O)CH3 | 365 |
| 398 | 2 | *-CF3 | 376 |

-continued

[Structure: 8-aryl-2-morpholino-4H-chromen-4-one with R on phenyl]

| Compound | Substituent position | Substituent | Mw LC-MS |
|---|---|---|---|
| 399 | 3 | *-CH2-N(phthalimide) | 467 |

-continued

[Structure: 8-R-2-morpholino-4H-chromen-4-one]

| Compound | Substituent | Mw LC-MS |
|---|---|---|
| 400 | 4-methyl-naphthalen-1-yl | 372 |
| 401 | styryl (trans-PhCH=CH-) | 334 |
| 402 | benzothiophen-3-yl | 364 |
| 403 | thiophen-3-yl | 314 |
| 404 | thiophen-2-yl | 314 |
| 405 | naphthalen-2-yl | 358 |
| 406 | furan-2-yl | 298 |
| 407 | 4-fluorostyryl | 352 |
| 408 | benzothiophen-2-yl | 364 |
| 409 | 5-acetylthiophen-2-yl | 356 |

-continued

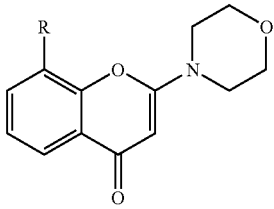

| Compound | Substituent | Mw LC-MS |
|---|---|---|
| 410 | dibenzofuran-yl | 398 |
| 411 | indol-yl | 347 |
| 412 | phenoxathiin-yl | 430 |
| 413 | dibenzothiophen-yl | 414 |

Route 8

7-(Benzyloxy)-2-(morpholin-4-yl)-chromen-4-one (Compound 337)

Prepared from benzyl bromide (0.25 ml, 2.0 mmol). Recrystallisation from methanol provided 0.098 g (0.29 mmol, 58% yield) as white crystals: mp 170-172° C. UV $\lambda_{max}$=258.0, 310.5 nm (methanol). $^1$H NMR (200 MHz., d$^6$-DMSO) δ 3.59 (4H, m); 3.82 (4H, m); 5.31 (2H, s, CH$_2$); 5.52 (1H, s, 3-H); 7.13 (1H, dd, J=2.3, 8.7 Hz., 6-H); 7.28 (1H, d, J=2.3 Hz., 8-H); 7.45-7.60 (5H, m); 7.91 (1H, d, J=8.7 Hz., 5-H). ESMS m/z=338 (M+), 179. Anal. Calcd for C$_{20}$H$_{19}$NO$_4$: C, 71.20; H, 5.68; N, 4.15. Found: C, 71.15; H, 5.63; N, 3.85.

7-(4-Fluorobenzyloxy)-2-morpholin-4-yl-chromen-4-one (Compound 414)

White crystals: mp 201-203° C. $^1$H NMR (200 MHz., d$^6$-DMSO) δ 3.60 (4H, m); 3.82 (4H, m); 5.29 (2H, s, CH$_2$); 5.52 (1H, s, 3-H); 7.13 (1H, m, 6-H); 7.29 (1H, m); 7.34 (2H, m); 7.64 (2H, m, 8-H); 7.92 (1H, m, 5-H). ESMS m/z=344 (M+)

7-(4-Chlorobenzyloxy)-2-morpholin-4-yl-chromen-4-one (Compound 415)

White crystals: decomp. >185° C. $^1$H NMR (200 MHz., d$^6$-DMSO) δ 3.60 (4H, m); 3.82 (4H, m); 5.31 (2H, s, CH$_2$); 5.52 (1H, s, 3-H); 7.13 (1H, dd, J=2.2, 8.7 Hz., 6-H); 7.28 (1H, d, J=2.2 Hz., 8-H); 7.59-7.71 (4H, m); 7.92 (1H, d, J=8.7 Hz., 5-H). ESMS m/z=371, 373 (M+)

7-(4-Bromobenzyloxy)-2-morpholin-4-yl-chromen-4-one (Compound 416)

White crystals: mp 221-222° C. $^1$H NMR (200 MHz., d$^6$-DMSO) δ 3.60 (4H, m); 3.82 (4H, m); 5.30 (2H, s, CH$_2$); 5.52 (1H, s, 3-H); 7.13 (1H, dd, J=2.0, 8.7 Hz., 6-H); 7.27 (1H, d, J=2.0 Hz., 8-H); 7.53 (2H, d, J=8.3 Hz.); 7.72 (2H, d, J=8.3 Hz.); 7.92 (1H, d, J=8.7 Hz., 5-H). ESMS m/z=419, 417 (M+)

7-(2-Chlorobenzyloxy)-2-morpholin-4-yl-chromen-4-one (Compound 417)

White crystals: mp 167-168° C. $^1$H NMR (200 MHz., d$^6$-DMSO) δ 3.61 (4H, m); 3.81 (4H, m); 5.36 (2H, s, CH$_2$); 5.54 (1H, s, 3-H); 7.15 (1H, dd, J=2.3, 8.7 Hz., 6-H); 7.35 (1H, d, J=2.3 Hz., 8-H); 7.50-7.76 (4H, m); 7.93 (1H, d, J=8.7 Hz., 5-H). ESMS m/z=373, 371 (M+)

7-(Naphthalen-2-ylmethoxy)-2-morpholin-4-yl-chromen-4-one (Compound 418)

White crystals: mp 263-264° C. $^1$H NMR (200 MHz., d$^6$-DMSO) δ 3.60 (4H, m); 3.81 (4H, m); 5.49 (2H, s, CH$_2$); 5.53 (1H, s, 3-H); 7.19 (1H, dd, J=2.2, 8.7 Hz., 6-H); 7.34 (1H, d, J=2.2 Hz., 8-H); 7.62-7.73 (3H, m); 7.92 (1H, d, J=8.7 Hz., 5-H); 8.02-8.11 (4H, m). ESMS m/z=387 (M+)

7-Cyclohexylmethoxy-2-(morpholin-4-yl)-chromen-4-one (Compound 419)

White crystals: mp 187-188° C. $^1$H NMR (200 MHz., d$^6$-DMSO) δ 1.16 (5H, m, cyclohexyl); 1.87 (6H, m, cyclohexyl); 3.60 (4H, m, morpholine); 3.80 (4H, m, morpholine); 3.97 (2H, s, CH$_2$); 5.50 (1H, s, 3-H); 7.12 (1H, dd, J=2.1, 8.7 Hz., 6-H); 7.18 (1H, d, J=2.1 Hz., 8-H); 7.88 (1H, d, J=8.7 Hz., 5-H). MS (ES+) m/z=344 (M+)

7-Propoxy-2-(morpholin-4-yl)-chromen-4-one (Compound 420)

White crystals: decomp. >115° C. $^1$H NMR (200 MHz., d$^6$-DMSO) δ 1.08 (3H, t, CH$_2$CH$_2$CH$_3$); 1.86 (2H, m, CH$_2$CH$_2$CH$_3$); 3.60 (4H, m); 3.81 (4H, m); 4.12 (2H, t, CH$_2$CH$_2$CH$_3$); 5.51 (1H, s, 3-H); 7.04 (1H, dd, J=2.0, 8.7 Hz., 6-H); 7.18 (1H, d, J=2.0 Hz., 8-H); 7.89 (1H, d, J=8.7 Hz., 5-H). ESMS m/z=290 (M+)

N-[2-(2-(Morpholin-4-yl)-4-oxo-4H-chromen-7-yloxy)-ethyl]-phthalimide (Compound 421)

White crystals: decomp. >230° C. ESMS m/z=421 (M+)

N-[3-(2-(Morpholin-4-yl)-4-oxo-4H-chromen-7-yloxy)-propyl]-phthalimide (Compound 422)

White crystals: mp 210-211° C. $^1$H NMR (200 MHz., d$^6$-DMSO) δ 2.60 (2H, m, NCH$_2$CH$_2$CH$_2$O); 3.58 (4H, m, morpholine); 3.81 (4H, m, morpholine); 3.89 (2H, m, NCH$_2$CH$_2$CH$_2$O); 4.22 (2H, m, NCH$_2$CH$_2$CH$_2$O); 5.50 (1H, s, 3-H); 6.86 (1H, dd, J=2.0, 8.6 Hz., 6-H); 7.03 (1H, d, J=2.0 Hz., 8-H); 7.83 (1H, d, J=8.6 Hz., 5-H); 7.95 (4H, m, phth-H$_4$). ESMS m/z=435 (M+).

Route 9

7-Benzoyloxy-2-(morpholin-4-yl)-chromen-4-one (Compound 423)

Prepared from benzoyl chloride (0.13 ml, 1.1 ml). Recrystallisation from ethyl acetate provided 0.19 g (0.55 mmol, 55%) as white crystals: mp 204-206° C. Anal. Calcd for C$_{20}$H$_{17}$NO$_5$: C, 68.37; H, 4.88; N, 3.99. Found: C, 68.14; H, 4.87; N, 3.73. UV$_{max}$=258.0, 311.0 nm (methanol). $^1$H NMR (200 MHz., d$^6$-DMSO) δ 3.64 (4H, m); 3.83 (4H, m); 5.65 (1H, s, 3-H); 7.45 (1H, m); 7.74 (3H, m); 8.87 (1H, m); 8.09 (1H, m); 8.26 (2H, m). MS (ES) m/z=352 (M$^+$); 179.

Further Synthesis Details 2-(2,3-dihydro-benzo[1,4]oxazin-4-yl)-benzo[h]chromen-4-one (Compound 424)

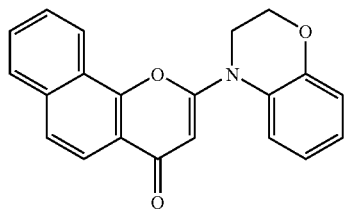

Synthesis of 3,4-dihydro-2H-benzo[1,4]oxazine

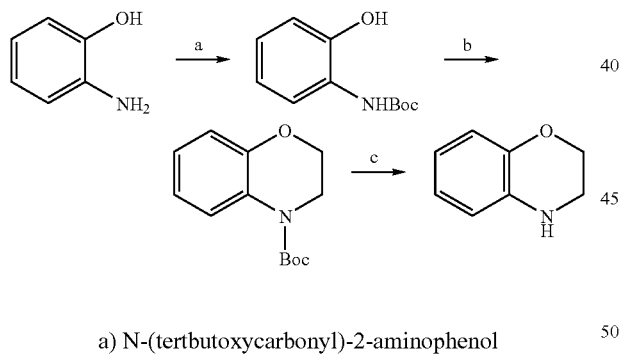

a) N-(tertbutoxycarbonyl)-2-aminophenol

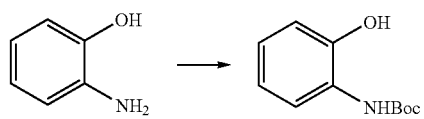

A mixture of 2-aminophenol (0.545 g, 5 mmol) and di-tert-butyldicarbonate (1.86 g, 10 mmol) in anhydrous THF (20 ml) was stirred at room temperature for 12 h. After concentration and hydrolysis, the aqueous layer were extracted with EtOAc (3×30 mL). The organic layer were combined and dried over MgSO$_4$ and the solvent was removed under reduce pressure. The crude product was purified by crystallisation (petrol/ether 8/2).

The pure compound is obtained as a white solid (0.839 g, 86% yield). m.p=145° C.; R$_f$=0.28 (petrol/ether 8/2); LCMS m/z 196 ([M+1]$^+$); $^1$H NMR (200 MHz, CDCl$_3$): δ 1.61 (9H, s); 6.65 (1H, bs); 6.48-7.08 (4H, m); 8.16 (1H, bs); $^{13}$C NMR (75 MHz, CDCl$_3$): (29.9 (3C); 83.7; 120.3; 122.5; 122.9; 127.1; 127.3; 148.9; 156.7. IR (film): 3280; 1688; 1146 cm$^{-1}$.

b) N-(tertbutoxycarbonyl)-2,3-dihydro-benzo[1,4]oxazine

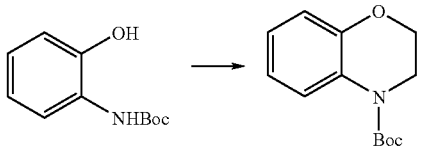

A solution of dry acetone (100 mL) containing N-(tertbutoxycarbonyl)-2-aminophenol (0.722 g, 3.69 mmol), potassium carbonate (10.2 g, 73.8 mmol) and 1,2-dibromobutane (2.54 mL, 29.6 mmol) was refluxed for 18 h. The reaction was monitored by TLC (petrol/ether 8/2). After cooling, the mixture was filtered through celite. After concentration and hydrolysis, the aqueous layer was extracted with EtOAc (3×40 mL), dried over MgSO$_4$ and the solvent was removed under reduce pressure. The crude product was purified by flash chromatography on silica gel (petrol/EtOAc 95/5) to yield the title compound as a white solid (0.70 g, 82%). m.p=78-79° C.; R$_f$=0.44 (petrol/ether 8/2); LCMS m/z 236 ([M+1]$^+$); $^1$H NMR (300 MHz, CDCl$_3$): δ 1.59 (9H, s); 3.87 (4H, m); 4.26 (4H, m); 6.86-7.02 (4H, m); $^{13}$C NMR (75 MHz, CDCl$_3$): δ 27.4 (3C); 41.1; 64.6 (2C); 80.6 (2C); 116.0; 119.2; 122.6; 123.4; 125.2; 144.9; 151.6. IR (film): 2975; 1696; 1494; 1143 cm$^{-1}$.

Ref: Kubick et al. Eur. J. Org. Chem. 2001, 311-312 c) 3,4-dihydro-2H-benzo[1,4]oxazine

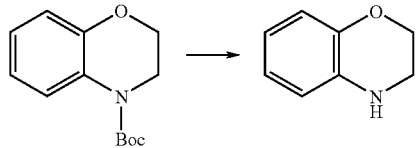

To a solution of dichloromethane (10 mL) containing N-(tertbutoxycarbonyl)-2,3-dihydro-benzo[1,4]oxazine (0.438, 1.86 mmol) at 0° C. was added slowly trifluoroacetic acid (1.0 mL, 7.44 mmol). The reaction mixture was stirred at this temperature during 5 h, then the solvent was removed in vaccuo. The crude product was dissolved in EtOAc (15 mL) and washed successively with 10% Na$_2$CO$_3$ solution and water. The organic layer was dried over MgSO$_4$ and the solvent was removed under reduce pressure. The title compound was obtained pure as brown oil (0.245 g, 98%). R$_f$=0.31 (petrol/ether 5/5); LCMS m/z 136 ([M+1]$^+$); $^1$H NMR (300 MHz, CDCl$_3$): δ 3.43 (4H, m); 3.54 (1H, s); 4.27 (4H, m); 6.60-6.82 (4H, m); $^{13}$C NMR (75 MHz, CDCl$_3$) δ 43.4; 67.7; 118.1; 119.2; 121.3; 123.7; 136.1; 146.6. IR (film): 3375; 1498; 741 cm$^{-1}$.

2-(2,3-dihydro-benzo[1,4]oxazin-4-yl)-benzo[h]chromen-4-one

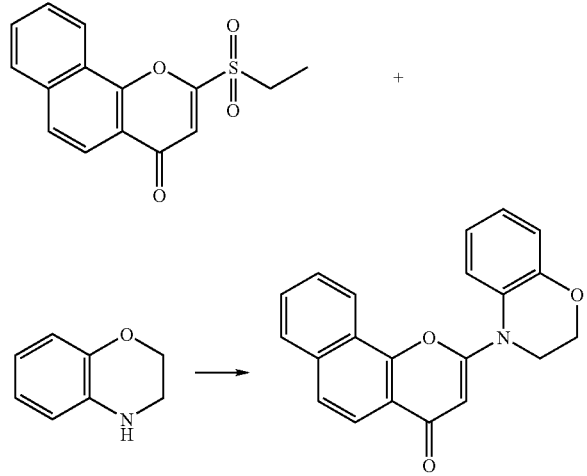

To a solution of anhydrous THF (5 mL) containing 3,4-dihydro-2H-benzo[1,4]oxazine (0.324 g, 1.6 mmol), at 0° C., was added dropwise n-BuLi (1.24 mL, 3.12 mmol, 2.5 N) while the temperature of 0-10° C. was maintained. After stirring for 30 min at 0° C., the sulfone (0.436 g, 1.6 mmol) was added in THF solution (10 mL). The reaction mixture was warmed slowly at rt and stirred for 20 h (TLC ether). The mixture was poured into 10 mL of 2N HCl (10 mL) and extracted with dichloromethane (3×20 mL). The organic layers were combined, dried over $MgSO_4$ and concentrated under reduce pressure. The crude product was purified by preparative HPLC to yield the title compound as a yellow solid (2 mg).

LCMS m/z 330 ([M+1]$^+$); $^1$H NMR (300 MHz, CDCl$_3$): δ 4.01 (2H, m, CH$_2$N), 4.35 (2H, m, CH$_2$O), 6.06 (1H, s), 6.85-7.05 (4H, m, ArH), 7.44-8.28 (6H, m, ArH).

Ref: Wynberg et al. *J. Org. Chem.* 1993, 58, 5101-5106

Biological Examples

DNA-PK Inhibition

In order to assess the inhibitory action of the compounds against DNA-PK in vitro, the following assay was used to determine IC$_{50}$ values.

Mammalian DNA-PK, isolated from Hela cell nuclear extract (Gell, D. and Jackson S. P., *Nucleic Acids Res.* 27:3494-3502 (1999)), was incubated with Z buffer (25 mM Hepes (Sigma); 12.5 mM MgCl$_2$ (Sigma); 50 mM KCl (Sigma); 1 mM DTT (Sigma); 10% Glycerol (Sigma); 0.1% NP-40 (Sigma); pH 7.4) in polypropylene 96 well plates and varying concentrations of inhibitor added. All compounds were diluted in DMSO to give a final assay concentration of between 10 and 0.001 μM, with DMSO being at a final concentration of 1% per well. The total assay volume per well was 40 μl.

After 10 minutes of incubation at 30° C. the reactions were initiated by the addition of Na-ATP (50 μM final), $^{33}$p-γATP and a 30mer double stranded DNA oligonucleotide (10 ng/μl) in a volume of 10 μl. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 μl 30% acetic acid to each well. The plates were then shaken for 5 minutes and the contents of each plate (80 μl from each well) transferred over to a 96 well Polyfiltronics filtration plate, containing P81-phosphocellulose membrane (TRADE MARK)(Whatman, UK). The solutions were vacuum pumped through the membrane and each well membrane washed four times using 300 μl of 15% acetic acid. The well membranes were then air dried and 20 μl of scintillant was added to each well.

The plates were transferred to a TopCount NXT (TRADE MARK) (Packard, UK) for scintillation counting. Values recorded are counts per minute (cpm) following a 1 minute counting time for each well.

The enzyme activity for each compound is then calculated using the following equation:

$$\% \text{ Inhibition} = 100 - \left( \frac{(\text{cpm of unknown} - \text{mean negative cpm}) \times 100}{(\text{mean positive cpm} - \text{mean negative cpm})} \right)$$

The results are detailed below in Table 1 as IC$_{50}$ values (the concentration at which 50% of the enzyme activity is inhibited). These are determined over a range of different concentrations, normally from 10 μM down to 0.01 μM. Such IC$_{50}$ values are used as comparative values to identify increased compound potencies. LY294002 exhibited an IC$_{50}$ of 1.5 μM.

Enhancement Ratio

The Enhancement Ratio (ER) is a ratio of the enhancement of cell growth inhibition elicited by the DNA-PK inhibitor after 2 Grays of irradiation compared to untreated control cells. DNA-PK inhibitors were used at a fixed concentration of 25 micromolar. Radiation was delivered by a Faxitron 43855D X-ray system at a dose rate of 1Gy per minute The Enhancement ratio at 2 Gy irradiation was calculated from the formula:

$$ER = \frac{\text{Cell growth in presence of } DNA\text{-}PK \text{ inhibitor} \times \text{Cell growth after } IR}{\text{Cell growth of untreated cells} \times \text{Cell growth after } IR \text{ in presence of } DNA\text{-}PK \text{ inhibitor}}$$

Cell growth was assessed using the sulforhodamine B (SRB) assay (Skehan, P., Storung, R., Scudiero, R., Monks, A., McMahon, J., Vistica, D., Warren, J. T., Bokesch, H., Kenny, S. and Boyd, M. R. (1990) New calorimetric cytotoxicity assay for anticancer-drug screening. J. Natl. Cancer Inst. 82:1107-1112). 400 HeLa cells were seeded into each well of a flat-bottomed 48-well microtiter plate in a volume of 200 μl and incubated for 6 h at 37° C. Cells were either replaced with media alone or with media containing DNA-PK inhibitor at a final concentration of 25 μM. Cells were allowed to grow for a further 1 h before irradiation or mock irradiation. Cells untreated with DNA-PK inhibitor or unirradiated were used as a control. Cells treated with DNA-PK inhibitor alone were used to assess the growth inhibition by the DNA-PK inhibitor.

Cells were left for a further 16 h before replacing the media and allowing the cells to grow for a further 6 days at 37° C. The media was then removed and the cells fixed with 200 μl of ice cold 10% (w/v) trichloroacetic acid. The plates were incubated at 4° C. for 20 minutes and then washed four times with water. Each well of cells was then stained with 200 µl of 0.4% (w/v) SRB in 1% acetic acid for 20 minutes before washing four times with 1% acetic acid. Plates were then dried for 2 h at room temperature. The dye from the stained cells was solubilized by the addition of 100 µl of 10 mM Tris Base into each well. Plates were gently shaken and left at room temperature for 30 minutes before measuring the optical density at 564 nM on a Microquant microtiter plate reader.

The results are detailed below in table 2. LY294002 exhibited an Enhancement Ration of 1.09.

PI 3-Kinase Inhibition

In order to assess the inhibitory action of the compounds against PI 3-kinase in vitro, the following assay was used to determine $IC_{50}$ values.

Baculoviral recombinant GST-fused PI 3-kinase (p110α/p85α) was purified from Sf9 insect cells using GSH-sepharose affinity chromatography as described (Wymann, M. T et al., (1996) Wortmannin inactivates phosphoinositide 3-kinase by covalent modification of Lys-802, a residue involved in the phosphate transfer reaction. Mol. Cell Biol. 16:1722-1733). PI 3-kinase (1 µl) was diluted in reaction buffer (89 µl of 50 mM Hepes pH 7.5, 150 mM NaCl, 0.1 mM Sodium Orthovanadate, containing 20 µg of phosphatidylinositol) and varying concentrations of inhibitor compound added. All compounds were diluted in DMSO to give a final assay concentration of between 100 and 0.1 µM, with DMSO being at a final concentration of 1%. After 10 minutes of incubation at 37° C. the reactions were initiated by the addition of 10 µl of 50 µM Na-ATP, 20 mM $MgCl_2$ and 2.5 µCi $^{33}$p-γATP. Reactions were incubated for a further 20 minutes at 37° C., before quenching with the addition of 400 µl of chloroform/methanol (1:1). Reactions were acidified by the addition of 200 µl of 1M HCl, before separation of the organic and aqueous phases by centrifugation at 10,000 g for 30 seconds. The organic phase was transferred to a fresh tube and washed twice with 150 µl of 1M hydrochloric acid/methanol (1:1), discarding the aqueous phase. The washed reaction product was then placed in a white 96-well plate with 100 µl of scintillation fluid and transferred to a TopCount NXT for scintillation counting. Counts per minute, following a one minute counting time, were recorded for each reaction. The inhibition of PI 3-kinase activity by compounds was calculated as described above for the DNA-PK assay.

The selectivity was determined by the following equation:

$$\Delta(DNA - PK/PI3 - K) = \frac{IC_{50}(PI3 - K)}{IC_{50}(DNA - PK)}$$

The results are detailed below in table 3. 294 exhibited an $IC_{50}$ of 1.5 µM, and a Δ(DNA-PK/PI 3-K) of 1.

ATM inhibition

In order to assess the inhibitory action of the compounds against ATM in vitro, the following assay was used to determine $IC_{50}$ values.

ATM protein was immunoprecipitated from HeLa cell nuclear extract using rabbit polyclonal antisera raised to the C-terminal ~500 amino-acid residues of the human ATM protein. The immunoprecipitation was performed according to the methodology described by Banin, S. et al. (1998) Enhanced phosphorylation of p53 by ATM in response to DNA damage. Science 281:1674-1677. 10 µl of immunoprecipitated ATM in Buffer C (50 mM Hepes, pH 7.4, 6 mM MgCl2, 150 mM NaCl, 0.1 mM sodium orthovanadate, 4 mM MnCl2, 0.1 mM dithiothreitol, 10% glycerol) was added to 32.5 µl of buffer C containing 1 µg of the ATM substrate GSTp53N66 in a V-bottomed 96 well polypropylene plate. The GSTp53N66 substrate is the amino terminal 66 amino acid residues of human wild type p53 fused to glutathione S-transferase. ATM phosphorylates p53 on the residue serine 15 (Banin, S. et al. (1998) Enhanced phosphorylation of p53 by ATM in response to DNA damage. Science 281:1674-1677). Varying concentrations of inhibitor were then added. All compounds were diluted in DMSO to give a final assay concentration of between 100 and 1 µM, with DMSO being at a final concentration of 1%. After 10 minutes of incubation at 37° C., the reactions were initiated by the addition of 5 µl of 50 µM Na-ATP. After 1 h with shaking at 37° C., 150 µl of phosphate buffered saline (PBS) was added to the reaction and the plate centrifuged at 1500 rpm for 10 minutes. 5 µl of the reaction was then transferred to a 96 well opaque white plate containing 45 µl of PBS to allow the GSTp53N66 substrate to bind to the plate wells. The plate was covered and incubated at room temperature for 1 h with shaking before discarding the contents. The plate wells were washed twice by the addition of PBS prior to the addition of 3% (w/v) bovine serum albumin (BSA) in PBS. The plate was incubated at room temperature for 1 h with shaking before discarding the contents and washing twice with PBS. To the wells, 50 µl of a 1:10,000 dilution of primary phosphoserine-15 antibody (Cell Signaling Technology, #9284L) in 3% BSA/PBS was added to detect the phosphorylation event on the serine 15 residue of p53 elicited by the ATM kinase. After 1 h of incubation at room temperature with shaking, the wells were washed four times with PBS prior to the addition of an anti-rabbit HRP conjugated secondary antibody (Pierce, 31462) with shaking for 1 h at room temperature. The wells were then washed four times with PBS before the addition of chemiluminescence reagent (NEN Renaissance, NEL105). The plate was then shaken briefly, covered with a transparent plate seal and transferred to a TopCount NXT for chemiluminescent counting. Counts per second, following a one second counting time, were recorded for each reaction. The inhibition of ATM activity by compounds was calculated as described above for the DNA-PK assay.

The selectivity was determined by the following equation:

$$\Delta(DNA - PK/ATM) = \frac{IC_{50}(ATM)}{IC_{50}(DNA - PK)}$$

The results are detailed below in table 4. 294 exhibited an $IC_{50}$ of >100 µM, and a Δ(DNA-PK/ATM) of >67.

All the compounds showed activity in DNA-PK inhibition, exhibiting an $IC_{50}$ of less than about 12 µM and/or % inhibition at 1 µM of more than about 22%.

Selected compounds and their $IC_{50}$ values are listed in table 1.

Compounds which exhibited particular efficacy in DNA-PK inhibition, having an $IC_{50}$ of less than about 1 µM and/or % inhibition of more than about 50 at 1 µM, include 270, 271, 272, 279, 267, 269, 268, 59, 60, 73, 131, 123, 139, 74, 125, 126, 127, 99, 124, 140, 143, 118, 105, 106, 104, 146, 107, 114, 163, 215, 194, 166, 187, 167, 157, 200, 169, 170, 202, 211, 173, 175, 176, 178, 179, 190, 192, 212, 182, 214, 203, 198, 205, 206, 264, 242, 258, 260, 247, 249, 252, 253, 255, 37, 31, 64, 65, 32, 68, 35, 36, 72, 293, 301, 297, 283, 287, 289, 288, 304, 5, 1, 292, 291, 290, 3, 4, 337, 418, 416, 422, 415, 6, 318, 338, 339, 340, 341, 426, 317, 366, 375, 385, 403, 404, 408, 409, 410, 389, 394 and 413.

TABLE 1

DNA-PK Inhibition

| Compound Number | $IC_{50}$ (μM) |
|---|---|
| 1 | 1.0 |
| 3 | 0.5 |
| 4 | 0.45 |
| 2 | 2.5 |
| 5 | 0.35 |
| 12 | 10.5 |
| 13 | 8 |
| 6 | 5 |
| 285 | 0.8 |
| 284 | 0.35 |
| 287 | 0.4 |
| 289 | 0.45 |
| 286 | 0.3 |
| 288 | 0.35 |
| 292 | 0.25 |
| 291 | 0.3 |
| 290 | 0.4 |
| 304 | 0.8 |
| 307 | 0.9 |
| 425 | 2.0 |
| 337 | 0.65 |
| 423 | 3.0 |
| 418 | 0.45 |
| 414 | 1.5 |
| 416 | 0.6 |
| 419 | 1.0 |
| 422 | 0.5 |
| 415 | 0.5 |
| 343 | 0.7 |
| 338 | 0.95 |
| 341 | 0.65 |
| 342 | 0.8 |
| 293 | 0.4 |
| 301 | 0.4 |
| 297 | 0.5 |
| 296 | 1.2 |
| 312 | 10 |
| 310 | 0.1 |
| 330 | 20 |
| 317 | 0.3 |

TABLE 2

Enhancement Ratio

| Compound Number | ER |
|---|---|
| 3 | 1.5 |
| 4 | 2.0 |
| 5 | 1.63 |
| 285 | 1.62 |
| 284 | 1.72 |
| 287 | 1.61 |
| 289 | 1.87 |
| 286 | 1.5 |
| 288 | 1.69 |
| 292 | 1.16 |
| 291 | 1.26 |
| 337 | 1.12 |
| 414 | 1.69 |
| 416 | 1.32 |
| 422 | 1.68 |
| 415 | 1.86 |
| 293 | 1.7 |
| 297 | 2.12 |
| 310 | 1.73 |
| 317 | 3.62 |

TABLE 3

PI 3-kinase Inhibition

| Compound Number | $IC_{50}$ (μM) | Δ(DNA-PK/PI 3-K) |
|---|---|---|
| 3 | 10 | 20 |
| 4 | 7 | 16 |
| 5 | 750 | >143 |
| 285 | 30 | 38 |
| 283 | 10 | 29 |
| 289 | 37 | 82 |
| 288 | 15 | 43 |
| 292 | 13 | 52 |
| 414 | 95 | 63 |
| 422 | 6 | 12 |
| 415 | >100 | >200 |
| 293 | 20 | 50 |
| 301 | 16 | 40 |
| 297 | 18 | 36 |
| 296 | 6 | 5 |
| 310 | 11 | 110 |
| 317 | 2.5 | 8 |

TABLE 4

ATM Inhibition

| Compound Number | $IC_{50}$ (μM) | Δ(DNA-PK/ATM) |
|---|---|---|
| 3 | >50 | >100 |
| 4 | >100 | >222 |
| 2 | >50 | >20 |
| 5 | >100 | >286 |
| 285 | >50 | >63 |
| 284 | >100 | >286 |
| 287 | >50 | >125 |
| 289 | >50 | >111 |
| 286 | 24 | 80 |
| 288 | >100 | >286 |
| 292 | >100 | >400 |
| 291 | >50 | >167 |
| 290 | 35 | 88 |
| 304 | >100 | >125 |
| 307 | >100 | >111 |
| 337 | >100 | >154 |
| 423 | >100 | >33 |
| 418 | >100 | >222 |
| 414 | >100 | >67 |
| 416 | >100 | >167 |
| 422 | >100 | >200 |
| 415 | >100 | >200 |
| 293 | >100 | >250 |
| 301 | >50 | >125 |
| 297 | 45 | 90 |
| 296 | >100 | >83 |
| 310 | >100 | >1000 |
| 317 | >100 | >333 |

The invention claimed is:

1. A method for the treatment of tumours comprising administering to a subject suffering from tumour growth a therapeutically-effective amount of a compound of formula Ia or Ib:

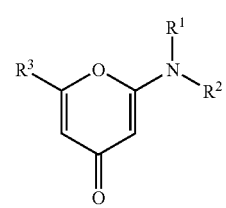

-continued

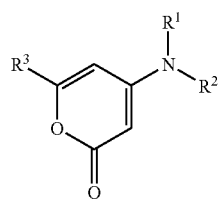

Ib and isomers, salts, and solvates, thereof, in combination with ionising radiation or one or more chemotherapeutic agents, wherein:

$R^1$ and $R^2$ are independently hydrogen, an optionally substituted $C_{1-7}$ alkyl group, $C_{3-20}$ heterocyclyl group, or $C_{5-20}$ aryl group, or may together form, along with the nitrogen atom to which they are attached, an optionally substituted heterocyclic ring having from 4 to 8 ring atoms; and $R^3$ is an optionally substituted $C_{5-20}$ aryl group.

2. The method according to claim 1, wherein $R^1$ and $R^2$ together with the nitrogen atom to which they are attached form a morpholino group.

3. The method according to claim 1, wherein $R^3$ is optionally substituted phenyl.

4. The method according to claim 3, wherein $R^3$ is phenyl substituted with a substituent selected from halo, $C_{1-7}$ alkyl, ether, alkoxy, nitro, cyano, acyl, formyl, ester, acyloxy, hydroxy, carboxy, $C_{5-20}$ aryl, $C_{3-20}$ heterocyclyl, acylamido, acylureido, thioureido, carbamate, carbazoyl, amido and amino.

5. The method according to claim 3, wherein $R^3$ is a monosubstituted phenyl.

6. The method according to claim 5, wherein $R^3$ is a 4-substituted phenyl.

7. The method according to claim 3, wherein the phenyl substituent is further substituted by halo, nitro, cyano, hydroxy, ester, ether, acyloxy, acyloxy, acyl, thioether, carboxy, amino $C_{5-20}$ aryl, $C_{1-7}$ alkyl or $C_{3-20}$ heterocyclyl.

* * * * *